(12) United States Patent
Brander et al.

(10) Patent No.: US 10,815,278 B2
(45) Date of Patent: *Oct. 27, 2020

(54) IMMUNOGENS FOR HIV VACCINATION

(71) Applicants: LABORATORIOS DEL DR. ESTEVE S.A., Barcelona (ES); FUNDACIÓ PRIVADA INSTITUT DE RECERCA DE LA SIDA—CAIXA, Badalona (ES)

(72) Inventors: Christian Brander, Tiana (ES); Beatriz Mothe Pujadas, Barcelona (ES); Anuska Llano, Castellar del Valles (ES)

(73) Assignees: Laboratorios del Dr. Esteve S.A., Barcelona (ES); Fundació Privada Institut de Recerca de La Sida—Caixa, Badalona (ES)

( * ) Notice: Subject to any disclaimer, the term of this patent is extended or adjusted under 35 U.S.C. 154(b) by 111 days.

This patent is subject to a terminal disclaimer.

(21) Appl. No.: 15/718,635

(22) Filed: Sep. 28, 2017

(65) Prior Publication Data

US 2018/0170971 A1 Jun. 21, 2018

Related U.S. Application Data

(63) Continuation of application No. 14/374,334, filed as application No. PCT/EP2013/051596 on Jan. 28, 2013, now Pat. No. 9,988,425.

(30) Foreign Application Priority Data

Jan. 27, 2012 (EP) .................................... 12382031

(51) Int. Cl.
*C07K 14/005* (2006.01)
*A61K 39/12* (2006.01)
(Continued)

(52) U.S. Cl.
CPC ............ *C07K 14/005* (2013.01); *A61K 39/12* (2013.01); *A61K 39/21* (2013.01); *C12N 7/00* (2013.01);
(Continued)

(58) Field of Classification Search
None
See application file for complete search history.

(56) References Cited

U.S. PATENT DOCUMENTS 5,081,226 A 1/1992 Berzofsky et al.
5,128,319 A 7/1992 Arlinghaus
(Continued)

FOREIGN PATENT DOCUMENTS

CH 568392 10/1975
EP 1312678 A1 5/2003
(Continued)

OTHER PUBLICATIONS

Adler, M., et al., Brit. Med. J., 1987,294:1145-1147.
(Continued)

*Primary Examiner* — Michelle S Horning
(74) *Attorney, Agent, or Firm* — Sterne, Kessler, Goldstein & Fox P.L.L.C.

(57) ABSTRACT

The present invention relates to novel immunogens based on overlapping peptides (OLPs) and peptides derived therefrom useful for the prevention and treatment of AIDS and its related opportunistic diseases. The invention also relates to isolated nucleic acids, vectors and host cells expressing these immunogens as well as vaccines including said immunogens.

31 Claims, 12 Drawing Sheets

Specification includes a Sequence Listing.

(51) Int. Cl.
*A61K 39/21* (2006.01)
*C12N 7/00* (2006.01)
*A61K 39/00* (2006.01)

(52) U.S. Cl.
CPC .. *A61K 2039/5256* (2013.01); *A61K 2039/53* (2013.01); *A61K 2039/545* (2013.01); *A61K 2039/57* (2013.01); *A61K 2039/575* (2013.01); *C07K 2319/35* (2013.01); *C12N 2740/16022* (2013.01); *C12N 2740/16034* (2013.01); *C12N 2740/16122* (2013.01); *C12N 2740/16134* (2013.01)

(56) References Cited

U.S. PATENT DOCUMENTS

| | | |
|---|---|---|
| 5,554,372 A | 9/1996 | Hunter |
| 5,639,854 A | 6/1997 | Sia et al. |
| 5,700,635 A | 12/1997 | McMichael et al. |
| 5,759,769 A | 6/1998 | Sia et al. |
| 5,795,955 A | 8/1998 | Sia et al. |
| 5,800,822 A | 9/1998 | Sia et al. |
| 5,817,754 A | 10/1998 | Sia et al. |
| 5,876,731 A | 3/1999 | Sia et al. |
| 5,951,986 A | 9/1999 | Sia et al. |
| 5,972,339 A | 10/1999 | Walker |
| 5,976,541 A | 11/1999 | Berzofsky et al. |
| 6,093,400 A | 7/2000 | Zimmerman et al. |
| 6,111,068 A | 8/2000 | Zimmerman et al. |
| 6,174,666 B1 | 1/2001 | Pavlakis et al. |
| 6,210,873 B1 | 4/2001 | Sastry et al. |
| 6,265,539 B1 | 7/2001 | Arlinghaus et al. |
| 6,268,472 B1 | 7/2001 | Zimmerman et al. |
| 6,268,945 B1 | 7/2001 | Zimmermann et al. |
| 6,294,322 B1 | 9/2001 | Berzofsky et al. |
| 6,440,422 B1 | 8/2002 | Sutter et al. |
| 7,094,405 B1 | 8/2006 | Berzofsky et al. |
| 7,094,408 B2 | 8/2006 | Franchini et al. |
| 7,319,000 B1 | 1/2008 | Sastry et al. |
| 7,569,228 B2 | 8/2009 | Howley et al. |
| 7,612,173 B2 | 11/2009 | Abrecht et al. |
| 7,815,916 B1 | 10/2010 | Chang et al. |
| 7,820,786 B2 | 10/2010 | Thomson et al. |
| 7,981,430 B2 | 7/2011 | Hanke et al. |
| 7,993,651 B2 | 8/2011 | Hanke et al. |
| 8,000,900 B2 | 8/2011 | Heckerman et al. |
| 8,021,669 B2 | 9/2011 | Howley et al. |
| 8,143,054 B2 | 3/2012 | Howley et al. |
| 8,198,082 B2 | 8/2012 | Hitchman et al. |
| 8,309,098 B2 | 11/2012 | Howley et al. |
| 8,478,535 B2 | 7/2013 | Jojic et al. |
| 9,017,691 B2 | 4/2015 | Barouch et al. |
| 9,133,478 B2 | 9/2015 | Moss et al. |
| 9,133,480 B2 | 9/2015 | Moss et al. |
| 9,988,425 B2 | 6/2018 | Brander et al. |
| 2002/0151678 A1 | 10/2002 | Arlinghaus |
| 2003/0108562 A1 | 6/2003 | Hanke et al. |
| 2003/0138409 A1 | 7/2003 | Pancre et al. |
| 2004/0073008 A1 | 4/2004 | Iglesias et al. |
| 2004/0105871 A1 | 6/2004 | Robinson et al. |
| 2004/0106136 A1 | 6/2004 | Dong |
| 2005/0249742 A1 | 11/2005 | Ruprecht et al. |
| 2006/0095241 A1 | 5/2006 | Jojic et al. |
| 2006/0160070 A1 | 7/2006 | Mallal et al. |
| 2006/0190226 A1 | 8/2006 | Jojic et al. |
| 2006/0257865 A1 | 11/2006 | Mallal |
| 2007/0015721 A1 | 1/2007 | Beaton et al. |
| 2007/0048861 A1 | 3/2007 | Robinson et al. |
| 2007/0248584 A1 | 10/2007 | Kent |
| 2008/0306244 A1 | 12/2008 | Hanke et al. |
| 2009/0060947 A1 | 3/2009 | Tartaglia et al. |
| 2009/0203144 A1 | 8/2009 | Beaton et al. |
| 2009/0252754 A1 | 10/2009 | Caputo et al. |
| 2010/0055119 A1 | 3/2010 | Stoloff et al. |
| 2010/0088037 A1 | 4/2010 | Mallal |
| 2010/0291061 A1 | 11/2010 | Jiang |
| 2011/0008417 A1 | 1/2011 | Peut et al. |
| 2011/0217307 A1 | 9/2011 | Hovenessian et al. |
| 2011/0277046 A1 | 11/2011 | Barton et al. |
| 2012/0082643 A1 | 4/2012 | Ruprecht et al. |
| 2012/0227120 A1 | 9/2012 | Hitchman et al. |
| 2012/0258126 A1 | 10/2012 | Scholler et al. |
| 2012/0308593 A1 | 12/2012 | Tartaglia et al. |
| 2013/0195904 A1 | 8/2013 | August et al. |
| 2013/0302364 A1 | 11/2013 | Mothe Pujadas et al. |
| 2015/0182618 A1 | 7/2015 | Stoloff et al. |

FOREIGN PATENT DOCUMENTS

| | | |
|---|---|---|
| EP | 1506223 B1 | 11/2005 |
| EP | 1773999 B1 | 9/2009 |
| EP | 2130921 A2 | 12/2009 |
| EP | 2292642 A1 | 3/2011 |
| EP | 2322626 A1 | 5/2011 |
| EP | 2358757 A1 | 8/2011 |
| EP | 2397489 A1 | 12/2011 |
| EP | 2402451 A2 | 1/2012 |
| EP | 1789438 B1 | 4/2015 |
| RU | 2 238 946 C2 | 10/2004 |
| WO | WO-9320212 A1 | 10/1993 |
| WO | WO 1996020013 | 7/1996 |
| WO | WO-9702355 A1 | 1/1997 |
| WO | WO 1997028816 | 8/1997 |
| WO | WO-2001049821 A2 | 7/2001 |
| WO | WO-0188141 A2 | 11/2001 |
| WO | WO-0232943 A2 | 4/2002 |
| WO | WO 2002042480 | 5/2002 |
| WO | WO-02068654 A2 | 9/2002 |
| WO | WO-03080112 A2 | 10/2003 |
| WO | WO-03097845 A1 | 11/2003 |
| WO | WO-2005028625 A2 | 3/2005 |
| WO | WO-2005030964 A1 | 4/2005 |
| WO | WO 2006010106 | 1/2006 |
| WO | WO-2006013106 A2 | 2/2006 |
| WO | WO-2006123256 A2 | 11/2006 |
| WO | WO-2007104932 A2 | 9/2007 |
| WO | WO-2008134068 A2 | 11/2008 |
| WO | WO-2008142479 A2 | 11/2008 |
| WO | WO-2009009743 A2 | 1/2009 |
| WO | WO-2010009346 A2 | 1/2010 |
| WO | WO 2010037402 | 4/2010 |
| WO | WO-2011042180 A1 | 4/2011 |
| WO | WO-2011047324 A1 | 4/2011 |
| WO | WO-2012062873 A2 | 5/2012 |

OTHER PUBLICATIONS

Altman, J., et al., Proc. Natl. Acad. Sci. USA, 1993, 90:10330-10334.
Altman, J., et al., Science, 1996, 274:94-96.
Altschul, S., et al., J. Mol. Biol., 1990, 215:403-410.
Altschul, S., et al., Nuc. Acids Res., 1997, 25:3389-3402.
Andre, S., et al., J. Virol., 1998, 72:1497-1503.
Auer, H., Nature Biotechnol., 2006, 24:41-43.
Betts, M., et al., J. Immunol. Methods, 2003, 281:65-78.
Brander, C., et al., Current Opinion Immunol., 2006, 18:430-437.
Brockman, M., et al., J. Virol., 2007,81:12608-12618.
Burke, S., et al., J. Inf. Dis., 1994, 170:1110-1119.
Chattopadhyay, P., et al., Nat. Med., 2005, 11:1113-1117.
Claverie, J.M., et al., Eur. J. Immunol., 1988, 18(10):1547-1553.
Davis, H., et al., Hum. Mol. Gen., 1993, 2:1847-1851.
Davis, H., et al., Vaccine, 1994, 12:1503-1509.
Extended European Search Report for EP12382031.8 dated Dec. 12, 2012.
Feng, L., et al., Biochemistry, 2000, 39(50):15399-15409.
Frahm, N., et al., J. Virol., 2004, 78:2187-2200.
Frahm, N., et al., Nat. Immunol., 2006, 7:173-178.
Frentsch, M., et al., Nat. Med., 2005, 11:1118-1124.
Friedrich, T., et al., J. Virol., 2007,81:3465-3476.
Hoffman, S., et al., Vaccine, 1994, 12(16):1529-1533.
Honeyborne, I., et al., J. Virol., 2007, 51:3667-3672.

(56) References Cited

OTHER PUBLICATIONS

Humphreys, D., et al., Protein Expr. Purif., 2000, 20(2):252-2.
International Search Report for PCT/EP2013/051596 dated Sep. 20, 2013.
Johnson, V., et al., ISA-USA Topics Antiviral Med., 2011; 19(4):153-164.
Johnston, S., et al., Meth. Cell Biol., 1994, 43:353-364.
Kiepiela, P., et al., Nature, 2004, 432:769-775.
Kiepiela, P., et al., Nat. Med., 2007, 13:46-53.
Leslie, A., et al., Nat. Med., 2004, 10:282-289.
Mannering, S., et al., J. Immunol. Methods, 2003, 283:173-183.
Mayr, A., et al., Infection, 1975, 3:6-14.
Mothe, B., et al., J. Trans. Med., 2011, 9(1):1-20.
Mothe, B., et al., Retrovirology, 2012, 9(2):P305.
Narum, D., et al., Infect. Immun., 2001, 9(12):7250-7253.
Ngumbela, K., et al., AIDS Res. Hum. Retroviruses, 2008, 24:72-82.
Nickle, D., et al., Science, 2003,299:1515-1517.
Novak, E., et al., J. Clin. Invest., 1999, 104:R63-R67.
Outchkourov, N., et al., Protein Expr. Purif., 2002, 24(1):18-24.
Robinson, H., et al., Vaccine, 1993, 11:957-960.
Rosati, M., et al., Proc. Natl. Acad. Sci., USA, 2009, 106:15831-15836.
Schneidewind, A., et al., J. Virol., 2007, 81:12382-12393.
Schwartz, S., et al., J. Virol., 1992, 66(12), 7176-7182.
Shafer, R., Assay for antiretroviral resistance, HIV insite knowledge base chapter (http://hivinsite.ucsf.edu/InSite?page=kb-02-02-03, Jan. 2012).
Shafer, R.,et al., AIDS Rev., 2008, 10(2):67-84.
Terpe, K., et al., Appl. Microbial. Biotechnol., 2003, 60:523-525.
Tigges, M., et al., J. Immunol., 1996, 156:3901-3910.
Watanabe, M., et al., Mol. Reprod. Dev., 1994, 38:268-274.
Webster, R., et al., Vaccine, 1994, 12:1495-1498.
Xiang, Z., et al., Virology, 1994, 199:132-140.
Yerly, D., et al., J. Birol., 2008,22:3147-3153.
Zuniga, R., et al., J. Viral., 2006, 80:3122-3125.
Arnold, P., et al., "The Majority of Immunogenic Epitopes Generate CD4+T Cells That Are Dependent on MHC Class II-Bound Peptide-Flanking Residues," *The Journal of Immunology 169*: 739-749, The American Association of Immunologists, United States (2002).
Correia, B.E., et al., "Proof of principle for epitope-focused vaccine design," *Nature* 507(7491): 201-206, Nature Publishing Group, England (2014).
Desai, D., and Kulkarni-Kale, U., "T-Cell Epitope Prediction Methods: An Overview," in *Immunoinformatics, Methods in Molecular Biology*, vol. 1184, De, Rajat K., and Tomar, Namrata (Eds.), Springer Science+Business Media, United States (2014).
French, S., and Robson, B., "What is a Conservative Substitution," *Journal of Molecular Evolution 19*:171-175, Springer-Verlag, Germany (1983).
Huarte, E., "Enhancing Immunogenicity of a CTL Epitope from Carcinoembryonic Antigen by Selective Amino Acid Replacements," *Clinical Cancer Research 8*, 2336-2344, American Association for Cancer Research, United States (2002).

Masemola, A., "Novel and Promiscuous CTL Epitopes in Conserved Regions of Gag Targeted by Individuals with Early Subtype C HIV Type 1 Infection from Southern Africa," *Journal of Immunology, 173*: 4607-4617 (2004).
Shang, X., et al., "Rational optimization of tumor epitopes using in silico analysis-assisted substitution of TCR contact residues," *European Journal of Immunology 39*: 2248-2258, WILEY-VCH Verlag GmbH & Co. KGaA, Germany (2009).
Salvat, R., et al., "Computationally driven deletion of broadly distributed T cell epitopes in a biotherapeutic candidate," *Cellular and Molecular Life Sciences 71*:4869-4880, Springer, Switzerland (2014).
Boggiano, C., et al., "Discovery and characterization of highly immunogenic and broadly recognized mimics of the HIV-1 CTL epitope Gag$_{77-85}$," *European Journal of Immunology 35*:1428-1437, WILEY-VCH Verlag GmbH & Co. KGaA, Germany (2005).
Ondondo, B., et al.,"Novel Conserved-region T-cell Mosaic Vaccine With High Global HIV-1 Coverage is Recognized by Protective Responses in Untreated Infection," *Molecular therapy: The American Society of Gene& Cell Therapy 24*:832-842, United States (2016).
Ebner, C., et al.,"Identification of Multiple T Cell Epitopes on Bet v I, the Major Birch Pollen Allergen, Using Specific T Cell Clones and Overlapping Peptides," The Journal of Immunology 150:1047-1057, American Association of Immunologists, United States (1993).
Bazhan, S.I., et al., "Rational design based synthetic polyepitope DNA vaccine for eliciting HIV-specific CD8+ T cell responses," Molecular Immunology 47:1507-1515, Elsevier, Netherlands (2010).
Robbins et al. Molecular Analysis in Support of an Investigation of a Cluster of HIV-1-Infected Women. Aids Res. Human Retro. 2002; 18(15): 1157-1161.
McGettigan et al. Functional Human Immunodeficiency Virus Type 1 (HIV-1) Gag-Pol or HIV-1 Gag-Pol and Env Expressed from a Single Rhabdovirus-Based Vaccine Vector Genome. J. Virol. 2003; 77(20): 10889-10899.
Mamadou et al. NCBI GenBank Accession Nos. CAD48448 and CAD48441; 2005.
Brennan et al. NCBI GenBank ABO61580.1, 2006.
Kusk et al. NCBI GenBank Accession No. AAB24615; 1993.
Morellet et al. NCBI GenBank Accession No. 1U57_A; 2005.
Zhang et al. NCBI GenBank Accession No. AAB83205.1; 1997.
Masquelier et al. NCBI GenBank Accession No. CAB51523; 1999.
Ntemgwa et al. NCBI GenBank Accession No. ABU62725.1, 2007.
Gatanaga et al. NCBI GenBank Accession No. BAO17739.1; 2007.
John et al. NCBI GenBank Accession No. ADF87031, 2010.
Powell et al. NCBI GenBank Accession No. ADF35429.1; 2009.
Saurya,S. NCBI GenBank Accession No. CAD23386; 2005.
Duque et al. NCBI GenBank Accession No. AAQ17444.1; 2003.
JK Wong, NCB I GenBank Accession No. AAB08224.1; 1996.
Sette et al. The Development of Multi-epitope Vaccines: Epitope Identification, Vaccine Design and Clinical Evaluation. Biologicals, 2001; 29: 271-276.
Brumme, Z.L. NCBI GenBank Accension No. ABY78164 (2010).
Frankel, A.D., "HIV-1: Fifteen Proteins and an RNA," Annual Rev. Biochem. 67:1-25, Annual Reviews, United States (1998).
Hancock, G., et al., "Identification of effective Subdominant Anti-Hiv-1 CD8+ T Cells within Entire Post-infection and Post-Vaccination Immune Responses," Public Library of Science Pathogens:1004658, Public Library of Science, United States (2015).

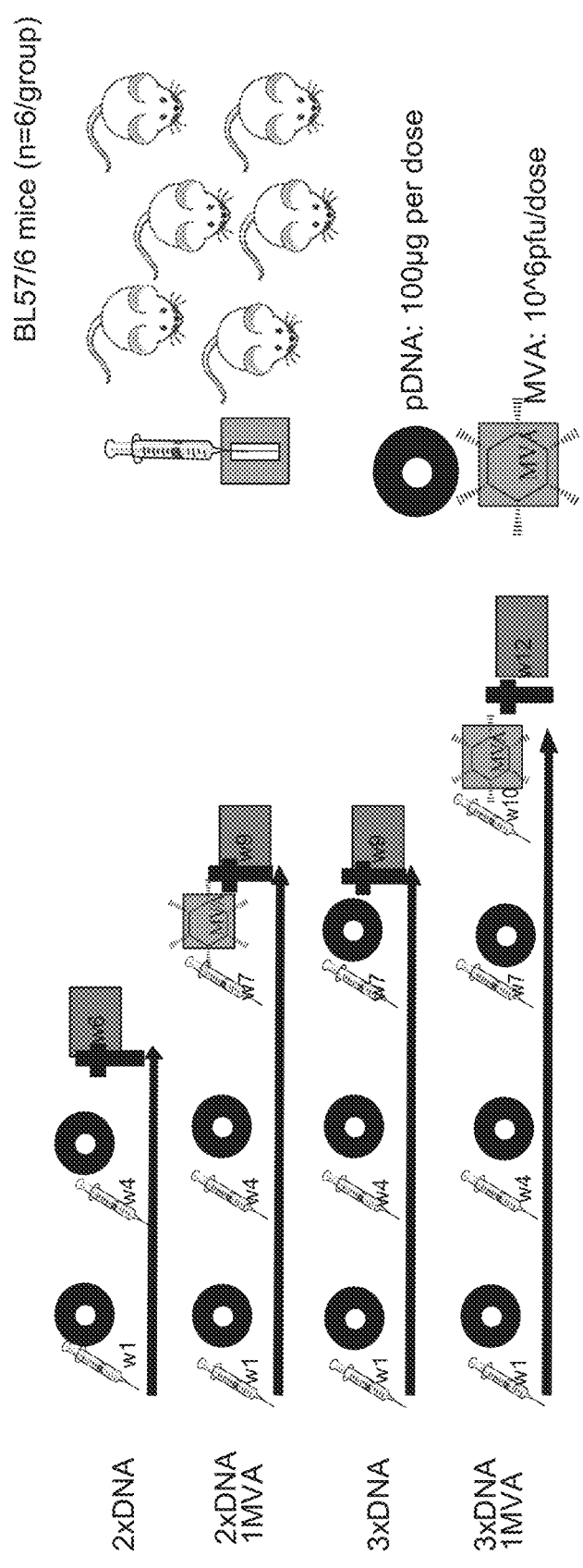

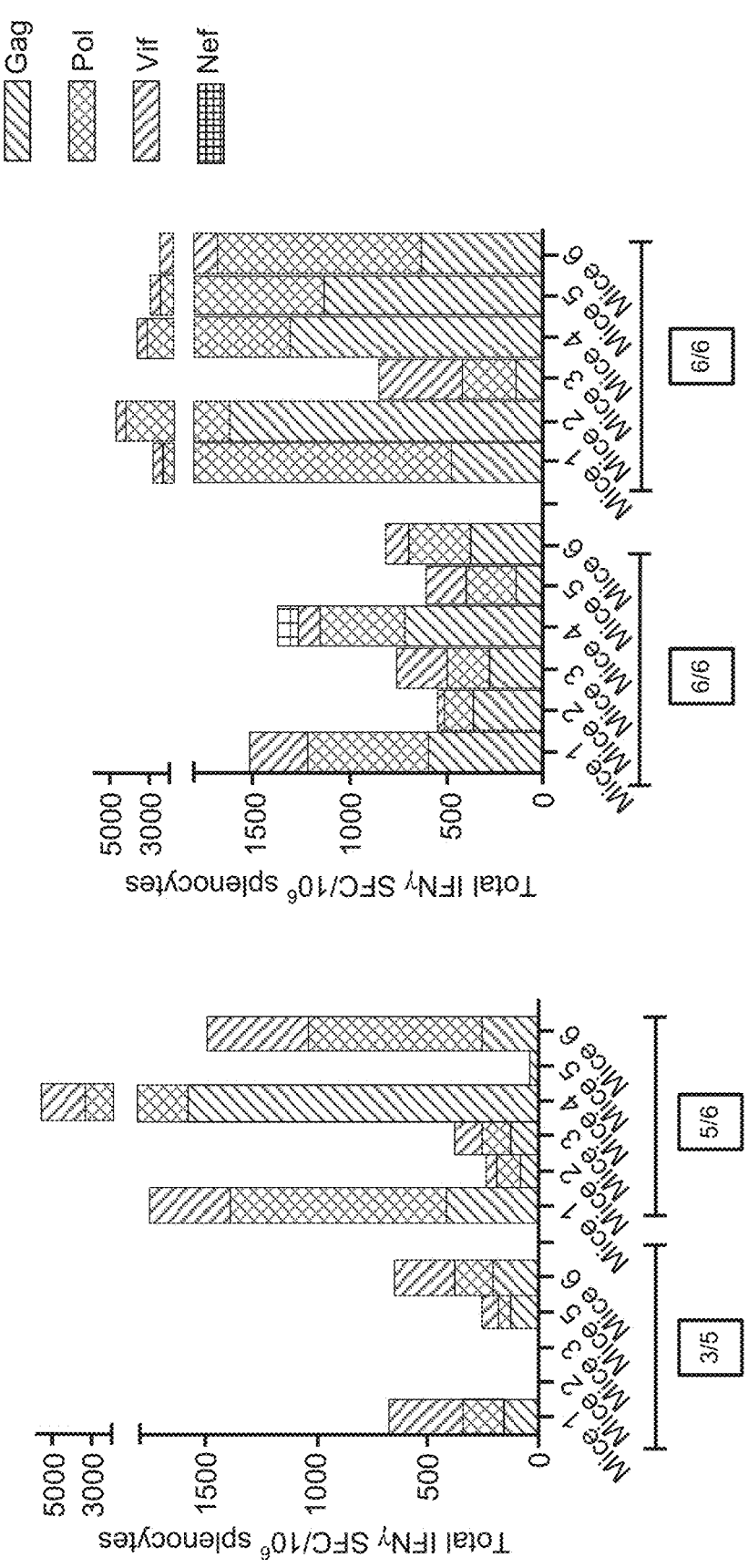

IMMUNOGENS FOR HIV VACCINATION

CROSS-REFERENCE TO RELATED APPLICATIONS

This application is a continuation of U.S. application Ser. No. 14/374,334, with a 35 U.S.C. § 371(c) date of Jul. 24, 2014, which is a national phase entry of International Application No. PCT/EP2013/051596, filed Jan. 28, 2013, which claims foreign priority to EP Application No. 12382031.8, filed Jan. 27, 2012, each of which is hereby incorporated by reference herein in its entirety.

REFERENCE TO SEQUENCE LISTING SUBMITTED ELECTRONICALLY

The content of the electronically submitted Sequence Listing (3834_0010001_Substitute_SL.txt; Size: 43,569 bytes; and Date of Creation: Dec. 20, 2017) filed with the application is incorporated herein by reference in its entirety.

FIELD OF THE INVENTION

The present invention relates to novel immunogens based on overlapping peptides (OLPs) and peptides derived therefrom. It also relates to isolated nucleic acids expressing these immunogens as well as vectors and cells comprising such nucleic acids. The compounds of the present invention are useful as vaccines, particularly for the prevention and treatment of AIDS and opportunistic diseases.

BACKGROUND OF THE INVENTION

HIV infection induces strong and broadly directed, HLA class I restricted T cell responses for which specific epitopes and restricting HLA alleles have been implicated in the relative in vivo control. See Brander C, et al., Current Opinion Immunol. 2006; 18:1-8. While the bulk of the anti-viral CTL response appears to be HLA-B restricted, the relative contribution of targeted viral regions and restricting HLA molecules on the effectiveness of these responses remains obscure. See Kiepiela P, et al., Nature 2004; 432:769-775 and Ngumbela K, et al., AIDS Res. Hum. Retroviruses 2008; 24:72-82.

In addition, the role that HIV sequence diversity plays in the in vivo relevance of virus-specific T cell immunity is unclear, as functional constraints of escape variants, codon-usage at individual protein positions, T cell receptor (TCR) plasticity and functional avidity and cross-reactivity potential may all contribute to the overall effectiveness of a specific T cell response. See Brockman M, et al., J. Virol. 2007; 81:12608-12618 and Yerly D, et al., J. Virol. 2008; 82:3147-3153. Of note, T cell responses to HIV Gag have most consistently been associated with reduced viral loads in both, HIV clade B and clade C infected cohorts. See Zuñiga R, et al., J. Virol. 2006; 80:3122-3125 and Kiepiela P, et al., Nat. Med. 2007; 13:46-53.

However, none of these analyses assessed the role of responses to shorter regions of the targeted protein(s) that may induce particularly effective responses. In addition, it is unclear whether the relative benefit of Gag is due to any other specific characteristic of this protein, such as expression levels, amino acid composition and inherently greater immunogenicity. It is thus feasible that protein subunits outside of Gag and within these, specific short epitope-rich regions could be identified that: i) induce responses predominantly seen in HIV controllers and ii) which would be detectable in individuals of diverse HLA types, not limited to individuals expressing alleles previously associated with effective viral control.

While some of the earlier studies have indeed controlled for a potential over-representation of Gag-derived epitopes presented on "good" HLA class I alleles, concerns remain that a purely Gag-based HIV vaccine might mainly benefit those people with an advantageous HLA genotype and will not take advantage of potentially beneficial targets outside of Gag. See Kiepiela, 2007, supra and Honeyborne I, et al., J. Virol. 2007; 81:3667-3672. In addition, CTL escape and viral fitness studies have largely been limited to Gag-derived epitopes presented in the context of relatively protective HLA alleles such as HLA-B57 and -B27. See Schneidewind A, et al., J. Virol. 2007; 81:12382-12393 and Leslie A, et al., Nat. Med. 2004; 10:282-289. The available information may thus not provide relevant information for immunogen sequences designed to protect the genetically diverse majority of the human host population.

Furthermore, many studies have focused on immunodominant targets only, despite some recent studies in HIV and SIV infection demonstrating a crucial contribution of sub-dominant responses in in vivo viral control, among them targets located outside of Gag. See Frahm N, et al., Nat. Immunol. 2006; 7:173-178 and Friedrich T, et al., J. Virol. 2007; 81:3465-3476. Together, the current view on what may constitute a protective cellular immune response to HIV is thus quite likely biased towards a focus on immunodominant responses and on responses restricted by frequent HLA class I alleles and HLA alleles associated with superior disease outcome. Therefore, the development of HIV vaccines is limited in part by the lack of immunogens capable of inducing a broad immune response. The present invention addresses the design of such immunogens.

SUMMARY OF THE INVENTION

In a first aspect, the invention relates to an immunogenic polypeptide having an amino acid sequence comprising the sequences SEQ ID NOs 1-16 or variants of said SEQ ID NO:1-16, wherein each of said variants has a length of at least 8 amino acids, with the provisos that said amino acid sequence does not comprise any sequence stretches derived from the HIV genome of a length of 8 or more amino acids other than an amino acid sequence according to any of SEQ ID NOs 1-16 or the variants thereof.

In a second aspect, the invention relates to an immunogenic polypeptide having an amino acid sequence comprising at least one sequence selected from the group consisting of the SEQ ID NOs 1-16 or variants thereof wherein said variant has a length of at least 8 amino acids, with the provisos that:
  i) said immunogen amino acid sequence does not comprise any sequence stretches derived from the HIV genome of a length of 8 or more amino acids other than an amino acid sequence according to any of SEQ ID NOs 1-16 or a variant or a fragment thereof, and
  ii) when the immunogen comprises only one sequence selected from the group consisting of SEQ ID NOs 1-16, then this sequence is not selected from the group consisting of SEQ ID NO: 3, 5, 6 and 16.

In further aspects, the invention relates to nucleic acids encoding for the immunogens of the first aspect and second aspects, and to expression cassettes, vectors, a viruses and cells comprising said nucleic acids.

In another aspect, the present invention relates to a vaccine comprising an immunogenic polypeptide according to any of claims 1 to 11 and one or more adjuvants.

In another aspect, the present invention relates to the immunogenic polypeptide, the nucleic acid, the expression cassette, the expression vector, the virus or the cell of the third aspect, or the composition vaccine for use in medicine.

In another aspect, the present invention relates to the immunogenic polypeptide, the nucleic acid, the expression cassette, the expression vector, the virus or the cell of the third aspect, or the composition vaccine for use in the prevention or treatment of an HIV infection or a disease associated with an HIV infection.

In another aspect, the present invention relates to a kit comprising the immunogen of the first and/or second aspects, the nucleic acid, the expression cassette, the expression vector, the virus or the cell of the third aspect, or the composition of the fourth aspect.

Deposit of Microorganisms

The plasmid 298H GMCSF-HIVACAT DNA was deposited on Jan. 13, 2012, under accession number DSM 25555 at the DSMZ-Deutsche Sammlung von Mikroorganismen and Zellkulturen, Inhoffenstraße 7 B, D-38124 Braunschweig, Federal Republic of Germany.

DETAILED DESCRIPTION OF THE INVENTION

Figure 1:
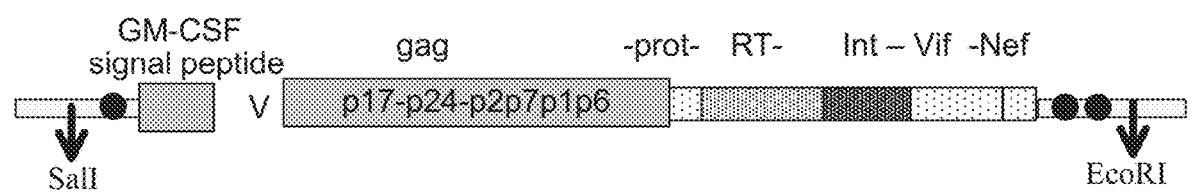
FIG. 1. Schematic representation of the gene included in the expression plasmid. Dots identify start and stop codons.

The invention discloses several immunogenic compounds effective for inducing a high immune response against HIV in a broad range of subjects. In particular, HIV-specific $CD4^+$ and $CD8^+$ T cell responses to key HIV-encoded epitopes have been obtained with these compounds.

1. Definitions of General Terms and Expressions

The term "adjuvant", as used herein, refers to an immunological agent that modifies the effect of an immunogen, while having few if any direct effects when administered by itself. It is often included in vaccines to enhance the recipient's immune response to a supplied antigen, while keeping the injected foreign material to a minimum. Adjuvants are added to vaccines to stimulate the immune system's response to the target antigen, but do not in themselves confer immunity. Non-limiting examples of useful adjuvants include mineral salts, polynucleotides, polyarginines, ISCOMs, saponins, monophosphoryl lipid A, imiquimod, CCR-5 inhibitors, toxins, polyphosphazenes, cytokines, immunoregulatory proteins, immunostimulatory fusion proteins, co-stimulatory molecules, and combinations thereof. Mineral salts include, but are not limited to, $AlK(SO_4)_2$, $AlNa(SO_4)_2$, $AlNH(SO_4)_2$, silica, alum, $Al(OH)_3$, $Ca_3(PO_4)_2$, kaolin, or carbon. Useful immunostimulatory polynucleotides include, but are not limited to, CpG oligonucleotides with or without immune stimulating complexes (ISCOMs), CpG oligonucleotides with or without polyarginine, poly IC or poly AU acids. Toxins include cholera toxin. Saponins include, but are not limited to, QS21, QS17 or QS7. An example of a useful immunostimulatory fusion protein is the fusion protein of IL-2 with the Fc fragment of immunoglobulin. Useful immunoregulatory molecules include, but are not limited to, CD40L and CD1a ligand. Cytokines useful as adjuvants include, but are not limited to, IL-1, IL-2, IL-4, GMCSF, IL-12, IL-15, IGF-1, IFNα, IFN-β, and interferon gamma. Also, examples of are muramyl dipeptides, N-acetyl-muramyl-L-threonyl-D-isoglutamine (thr-DMP), N-acetyl-nornuramyl-L-alanyl-D-isoglutamine (CGP 11687, also referred to as nor-MDP), N-acetylmuramyul-L-alanyl-D-isoglutaminyl-L-alanine-2-(1'2'-dipalmitoyl-sn-glycero-3-hydroxphosphoryloxy)-ethylamine (CGP 19835A, also referred to as MTP-PE), RIBI (MPL+TDM+CWS) in a 2 percent squalene/TWEEN® 80 emulsion, lipopolysaccharides and its various derivatives, including lipid A, Freund's Complete Adjuvant (FCA), Freund's Incomplete Adjuvants, Merck Adjuvant 65, polynucleotides (e.g. poly IC and poly AU acids), wax D from *Mycobacterium tuberculosis*, substances found in *Corynebacterium parvum, Bordetella pertussis*, and members of the genus *Brucella*, Titermax, Quil A, ALUN, Lipid A derivatives, choleratoxin derivatives, HSP derivatives, LPS derivatives, synthetic peptide matrixes or GMDP, Montanide ISA-51 and QS-21, CpG oligonucleotide, poly I:C, and GMCSF. See Osol A., Ed., Remington's Pharmaceutical Sciences (Mack Publishing Co., Easton, Pa., US, 1980, pp. 1324-1341), Hunter R, U.S. Pat. No. 5,554,372, and Jager E, Knuth A, WO1997028816. Combinations of adjuvants can also be used.

The term "AIDS", as used herein, refers to the symptomatic phase of HIV infection, and includes both Acquired Immune Deficiency Syndrome (commonly known as AIDS) and "ARC," or AIDS-Related Complex. See Adler M, et al., Brit. Med. J. 1987; 294: 1145-1147. The immunological and clinical manifestations of AIDS are well known in the art and include, for example, opportunistic infections and cancers resulting from immune deficiency.

The term "amino acid linker", as used herein, refers to an amino acid sequence other than that appearing at a particular position in the natural protein and is generally designed to be flexible or to interpose a structure, such as an α-helix, between two protein moieties. A linker is also referred to as a spacer. The linker is typically non-antigenic and can be of essentially any length (e.g. 2, 3, 4, 5, 6, 7, 8, 9, 10, 11, 12, 13, 14, 15, 16, 17, 18, 19, 20, or more amino acids). The linker may also be a location or sequence where the cellular antigen processing machinery can initiate the degradation of the immunogenic polypeptide without destroying potent T cell epitopes).

The term "antiretroviral resistance mutation site", as used herein, relates to a site that, when mutated, confers resistance to an antiretroviral agent. Such sites can be identified by mining known databases such as the Stanford University HIV Drug Resistance Database, where, for example, sequences and treatments from viruses with specific mutations or drug susceptibility data for isolates with selected mutations can be retrieved. Assays for testing drug resistance of HIV are known in the art. See Dong J, US 20040106136 and Shafer R, Assay for Antiretroviral Resistance, HIV InSite Knowledge Base Chapter (http://hivinsite.ucsf.edu/InSite?page=kb-02-02-03, January 2012). Already known antiretroviral resistance mutation sites in HIV are regularly published by the World Health Organization or the by the International Antiviral Society-USA (e.g. Johnson V, et al., ISA-USA Topics Antiviral Med. 2011; 19(4): 153-164.

The expression "cellular immune response", as used herein, describes an immune response against foreign antigen(s) that is mediated by T cells and their secretion products.

The term "center-of-tree sequence" or "COT", as used herein, refers to a sequence from which the average evolutionary distance to each tip of a phylogenetic diagram of related variant sequences has been minimized. See Nickle D, et al., Science 2003; 299, 1515-1517.

The term "codon optimized", as used herein, relates to the alteration of codons in nucleic acid molecules to reflect the typical codon usage of the host organism without altering the polypeptide encoded by the DNA, to improve expression. A plethora of methods and software tools for codon optimization have been reported previously. See Narum D, et al., Infect. Immun. 2001; 69(12):7250-7253, Outchkourov N, et al., Protein Expr. Purif 2002; 24(1):18-24, Feng L, et al., Biochemistry 2000; 39(50):15399-15409, and Humphreys D, et al., Protein Expr. Purif. 2000; 20(2):252-2.

The term "comprising" or "comprises", as used herein, discloses also "consisting of" according to the generally accepted patent practice.

The expression "disease associated with a HIV infection", as used herein, includes a state in which the subject has developed AIDS, but also includes a state in which the subject infected with HIV has not shown any sign or symptom of the disease. Thus, the vaccine of the invention when administered to a subject that has no clinical signs of the infection can have a preventive activity, since they can prevent the onset of the disease. The immunogenic compositions are capable of preventing or slowing the infection and destruction of healthy CD4+ T cells in such a subject. It also refers to the prevention and slowing the onset of symptoms of the acquired immunodeficiency disease such as extreme low CD4+ T cell count and repeated infections by opportunistic pathogens such as *Mycobacteria* spp *Pneumocystis carinii*, and *Pneumocystis cryptococcus*. Beneficial or desired clinical results include, but are not limited to, an increase in absolute naive CD4+ T cell count (range 10-3520), an increase in the percentage of CD4+ T cell over total circulating immune cells (range 1-50 percent), and/or an increase in CD4+ T cell count as a percentage of normal CD4+ T cell count in an uninfected subject (range 1-161 percent).

The terms "variant" or "fragment", as used herein, refer to a polypeptide derived from any of SEQ ID NOs 1-16 by deletion of one or more terminal amino acids at the N-terminus or at the C-terminus of an individual SEQ ID NO. Variant or fragments preferably have a length of at least 8 amino acids or up to 10%, up to 20%, up to 30%, up to 40%, up to 50%, up to 60%, up to 70%, up to 80%, up to 90%, or up to 99% of its respective SEQ ID NO.

The term "HIV genome", as used herein, refers to a RNA sequence approximately 8749 nucleotide long enclosed by the HIV capsid and encoding the genes gag, pol, env, tat, rev, vif, nef, vpr, vpu, vpx, and optionally, tev. The HIV genome sequence underlies high variability, for this reason, the HIV genome referred to in the invention is not limited to any specific sequence. Preferred sequences are those of the HIV types and subtypes recited herein.

The term "human immunodeficiency virus" or "HIV", as used herein, refer human immunodeficiency viruses generically and includes HIV type 1 ("HIV-1"), HIV type 2 ("HIV-2") or other HIV viruses, including, for example, the HIV-1, HIV-2, emerging HIV and other HIV subtypes and HIV variants, such as widely dispersed or geographically isolated variants and simian immunodeficiency virus ("SIV"). For example, an ancestral viral gene sequence can be determined for the env and gag genes of HIV-1, such as for HIV-1 subtypes A, B, C, D, E, F, G, H, J, and K, and intersubtype recombinants such as AG, AGI, and for groups M, N, O or for HIV-2 viruses or HIV-2 subtypes A or B. HIV-1, HIV-2 and SIV include, but are not limited to, extracellular virus particles and the forms of the viruses associated with their respective infected cells.

The "humoral immune response", as used herein, describes an immune response against foreign antigen(s) that is mediated by antibodies produced by B cells.

The term "immunogenic composition", as used herein, refers to a composition that elicits an immune response that produces antibodies or cell-mediated immune responses against a specific immunogen.

The term "immunogenic polypeptide" or "immunogen", as used herein, refers to a polypeptide antigen that is able to induce an adaptive immune response (i.e. a humoral or cell-mediated immune response), if injected on its own or with an adjuvant.

The term "kit", as used herein, refers to a combination of articles that facilitate a process, method or application. These kits provide the materials necessary for carrying out the application described in the present invention.

The term "operably linked", as used herein, is intended to mean that the nucleotide sequence of interest is linked to the regulatory sequence(s) in a manner that allows for expression of the nucleotide sequence (e.g. in an in vitro transcription/translation system or in a host cell when the vector is introduced into the host cell). See Auer H, Nature Biotechnol. 2006; 24: 41-43.

The term "peptide tag" or "tag", as use herein, refers to a peptide or amino acid sequence, which can be used in the isolation or purification of said immunogen. Thus, said tag is capable of binding to one or more ligands, for example, one or more ligands of an affinity matrix such as a chromatography support or bead with high affinity. Illustrative, non-limitative, examples of tags useful for isolating or purifying a protein include Arg-tag, FLAG-tag, His-tag, or Strep-tag; an epitope capable of being recognized by an antibody, such as c-myc-tag (recognized by an anti-c-myc antibody), SBP-tag, S-tag, calmodulin binding peptide, cellulose binding domain, chitin binding domain, glutathione S-transferase-tag, maltose binding protein, NusA, TrxA, DsbA or Avi-tag; an amino acid sequence, such as AHGHRP (SEQ ID NO:53), PIHDHDHPHLVIHS (SEQ ID NO:54), or GMTCXXC (SEQ ID NO:55); or β-galactosidase. See Terpe K, et al., Appl. Microbiol. Biotechnol. 2003; 60:523-525.

The terms "pharmaceutically acceptable carrier," "pharmaceutically acceptable diluent," or "pharmaceutically acceptable excipient", or "pharmaceutically acceptable vehicle," as used interchangeably herein, refer to a non-toxic solid, semisolid or liquid filler, diluent, encapsulating material or formulation auxiliary of any conventional type. A pharmaceutically acceptable carrier is essentially non-toxic to recipients at the employed dosages and concentrations and is compatible with other ingredients of the formulation. For example, the carrier for a formulation containing polypeptides would not include normally oxidizing agents and other compounds known to be deleterious to polypeptides. Suitable carriers include, but are not limited to, water, dextrose, glycerol, saline, ethanol, and combinations thereof. The carrier can contain additional agents such as wetting or emulsifying agents, pH buffering agents, or adjuvants that enhance the effectiveness of the formulation.

The terms "prevent," "preventing," and "prevention", as used herein, refer to inhibiting the inception or decreasing the occurrence of a disease in an animal. Prevention may be complete (e.g. the total absence of pathological cells in a subject). The prevention may also be partial, such that for example the occurrence of pathological cells in a subject is less than that which would have occurred without the present invention. Prevention also refers to reduced susceptibility to a clinical condition.

The term "secretion signal peptide" refers to a highly hydrophobic amino acid sequence (e.g. preferably 15 to 60 amino acids long) of proteins that must cross through membranes to arrive at their functioning cellular location. By binding to signal recognition particles, these sequences direct nascent protein-ribosome complexes to a membrane where the protein is inserted during translation. Signal peptides direct translational uptake of the protein by various membranes (e.g. endoplasmic reticulum, mitochondria, chloroplast, peroxisome). Leader signal sequences on non-membrane proteins are ultimately removed by specific peptidases. Some signal peptides used include MCP-3 chemokine, for promoting secretion and attraction of antigen presenting cells; a catenin (CATE)-derived peptide for increased proteasomal degradation; and the lysosomal associated protein, LAMP1 for targeting the MHC II compartment. See Rosati M, et al., Proc. Natl. Acad. Sci. USA 2009; 106:15831-15836.

The expression "sequential administration", as used herein, means that the administration is not simultaneous, but a first administration is performed, followed by one or more successive administrations.

The expression "substantially preserves the immunological capabilities of the immunogenic polypeptide", as used herein, means that the variant shows at least 10%, at least 20%, at least 30%, at least 40%, at least 50%, at least 60%, at least 70%, at least 80%, at least 90%, at least 95% or 100% of the ability of the immunogenic polypeptide for inducing an adaptive immune response (i.e. a humoral or cell-mediated immune response), if injected on its own or with adjuvants.

The term "treat" or "treatment", as used herein, refers to the administration of an immunogenic composition of the invention or of a medicament containing it to control the progression of the disease before or after clinical signs have appeared. Control of the disease progression is understood to mean the beneficial or desired clinical results that include, but are not limited to, reduction of the symptoms, reduction of the duration of the disease, stabilization of pathological states (specifically to avoid additional deterioration), delaying the progression of the disease, improving the pathological state and remission (both partial and total). The control of progression of the disease also involves an extension of survival, compared with the expected survival if treatment was not applied.

The term "vaccine", as used herein, refers to a substance or composition that establishes or improves immunity to a particular disease by inducing an adaptive immune response including an immunological memory. A vaccine typically contains an agent that resembles a disease-causing microorganism or a part thereof (e.g. a polypeptide). Vaccines can be prophylactic or therapeutic.

The term "variant", as used herein, refers to all those amino acid sequences derived from any of SEQ ID NOs 1-16 by means of modifications or mutations, including substitutions, preferably conservative substitutions, insertions or non-terminal deletions, affecting one or more amino acids and which substantially preserves the immunogenic capabilities of the immunogenic polypeptide.

The term "vector", as used herein, refers to a nucleic acid molecule, linear or circular, that comprises a segment according to the nucleic acid of interest operably linked to additional segments that provide for its autonomous replication in a host cell of interest or according to the expression cassette of interest.

2. Immunogenic Polypeptides of the Invention

In a first aspect, the invention relates to an immunogenic polypeptide having an amino acid sequence comprising the sequences SEQ ID NOs 1-16 or variants of said SEQ ID NO:1-16, wherein each of said variants has a length of at least 8 amino acids, with the provisos that said amino acid sequence does not comprise any sequence stretches derived from the HIV genome of a length of 8 or more amino acids other than an amino acid sequence according to any of SEQ ID NOs 1-16 or the variants thereof.

In a particular embodiment, the immunogenic polypeptide of the first aspect has an amino acid sequence comprising SEQ ID NO: 49.

In a second aspect, the invention relates to an immunogenic polypeptide having an amino acid sequence comprising at least one sequence selected from the group consisting of the SEQ ID NOs 1-16 or variants thereof or a fragment thereof, wherein said fragment has a length of at least 8 amino acids, with the provisos that:
  i) said amino acid sequence does not comprise any sequence stretches derived from the HIV genome of a length of 8 or more amino acids other than an amino acid sequence according to any of SEQ ID NOs 1-16 or a variant or a fragment thereof, and
  ii) when the immunogen comprises only one sequence selected from the group consisting of SEQ ID NOs 1-16, then this sequence is not selected from the group consisting of SEQ ID NO: 3, 5, 6 and 16.

Preferably, the variant according to the first and second aspects is equivalent to its related sequence and derives from a different HIV strain or is an artificial HIV sequence. Equivalent in this respect means different in one or more amino acid residues, but corresponding to the same sequence (e.g. determined by the position in the genome or sequence similarity). In other words, in a preferred embodiment, the variant is a "naturally occurring variant", which refers to nucleic acid sequences derived from an HIV genome of a presently or formerly circulating virus and can be identified from existing databases (e.g. GenBank and Los Alamos sequence databases). The sequence of circulating viruses can also be determined by molecular biology methodologies. See Brown T, "Gene Cloning" (Chapman & Hall, London, GB, 1995); Watson R, et al., "Recombinant DNA", 2nd Ed. (Scientific American Books, New York, N.Y., US, 1992); Sambrook J, et al., "Molecular Cloning. A Laboratory Manual" (Cold Spring Harbor Laboratory Press, Cold Spring Harbor, N.Y., US, 1989). Preferably, a variant of any of SEQ ID NOs 1-16 has an amino acid sequence identity of at least 70%, at least 80%, at least 90%, at least 95%, at least 98%, or at least 99% to its corresponding (i.e. SEQ ID NOs 1-16). Examples of algorithms suitable for determining percent sequence identity and sequence similarity are BLAST and BLAST 2.0 algorithms. See Altschul S, et al., Nuc. Acids Res. 1977; 25:3389-3402 and Altschul S, et al., J. Mol. Biol. 1990; 215:403-410. The BLAST and BLAST 2.0 programs can be used to determine percent sequence identity for the nucleic acids and proteins of the invention. Software for performing BLAST analyses is publicly available through the National Center for Biotechnology Information. See http://blast.ncbi.nlm.nih.gov/blast.cgi, January 2012.

Variants may also contain one or more modified amino acid residues (e.g. residues that are modified by the attachment of substituent groups), or one or more unnatural amino acids such as beta amino acids.

Methods for determining the extent of the cellular response are known in the art. Any method suitable for assessing the stimulation of T cells in response to an Ag can be used. The procedures described below provide a few examples of suitable methods:

1) Enzyme-linked immunospot (ELISpot): non-adherent cells from pre-culture wells are transferred to a plate, which has been coated with the desired anti-cytokine capture antibodies (Abs; e.g. anti-IFN, -IL-10, -IL-2, -IL-4). Revelation is carried out with biotinylated secondary Abs and standard colorimetric or fluorimetric detection methods such as streptavidin-alkaline phosphatase and NBT-BCIP and the spots counted. ELISpot readouts are then expressed as spot-forming cells (SFC)/$10^6$ input cells.
2) Supernatant cytokine assay: cytokines released in the culture supernatant are measured by different techniques, such as enzyme-linked immunosorbent assays (ELISA), BD cytometric bead array, Biorad Bio-Plex assay and others.
3) HLA Class I tetramers: with this procedure, Ag-reactive T cells recognizing specific peptide epitopes are detected, using either commercially available reagents (e.g. MHC Class I Dexamers, Immudex, Copenhagen, DK) or in-house generated ones (e.g. Novak E, et al., J. Clin. Invest. 1999; 104:R63-R67).
4) HLA Class II tetramers: with this procedure, Ag-reactive T cells recognizing specific peptide epitopes are detected, using either commercially available reagents (e.g. MHC Class II Ultimers™, ProImmune Ltd, Oxford, GB) or in-house generated ones (e.g. Novak, 1991, supra).
5) Upregulation of activation markers (e.g. CD69, CD25, CD137): with this procedure, Ag-specific T cell responses are detected by their differential expression of activation markers exposed on the membrane following Ag-recognition.
6) Cytokine capture assays: this system is a valid alternative to the ELISpot to visualize Ag-specific T cells according to their cytokine response (Miltenyi Biotec GmbH, Bergisch Gladbach, DE). In addition, it allows the direct sorting and cloning of the T cells of interest.
7) CD154 assay: this procedure is limited to detection of Ag-specific CD4+ T cells. See Chattopadhyay P, et al., Nat. Med. 2005; 11:1113-11117 and Frentsch M, et al., Nat. Med. 2005; 11:1118-1124.
8) CD107 assay: this procedure allows the visualization of Ag-specific CD8+ T cells with cytotoxic potential. See Betts M, et al., J. Immunol. Methods 2003; 281:65-78.
9) CFSE dilution assay: this procedure detects Ag-specific T cells (CD4+ and CD8+) according to their proliferation following Ag recognition. See Mannering S, et al., J. Immunol. Methods 2003; 283:173-183.

Methods for determining the extent of the humoral response of a variant are known in the art. Any method suitable for assessing the stimulation of T cells in response to an Ag can be used. Examples of suitable methods include, but are not limited to, detecting or quantitating the relative amount of an antibody, which specifically recognizes an antigenic or immunogenic agent in the sera of a subject who has been treated with an immunogenic polypeptide or variant relative to the amount of the antibody in an untreated subject. Antibody titers can be determined using standard assays such as enzyme-linked immunosorbent assay (ELISA), Single Radial Immunodiffussion Assay (SRID), or Enzyme Immunoassay (ETA).

In a preferred embodiment, the variant of any of SEQ ID NOs 1-16 is a fragment of said sequence(s).

In specific embodiments, ancestral viral sequences are determined for the env genes of HIV-1 subtypes B or C, or for the gag genes of subtypes B or C. In other embodiments, the ancestral viral sequence is determined for other HIV genes or polypeptides, such as pol or the auxiliary genes or polypeptides. In yet another embodiment, the viral sequence is determined by consensus or center-of-tree techniques.

In a preferred embodiment, the HIV is a group M HIV. Group M is the predominant circulating HIV-1 group. It has been divided into subtypes, denoted with letters, and sub-subtypes, denoted with numerals. Subtypes A1, A2, A3, A4, B, C, D, E, F1, F2, G, H, J, and K are currently recognized. HIV-1 subtypes, also called clades, are phylogenetically linked strains of HIV-1 that are approximately the same genetic distance from one another; in some cases, subtypes are also linked geographically or epidemiologically. Genetic variation within a subtype can be 15 to 20 percent or more, whereas variation between subtypes or divergent members of the same subtype is usually 25 to 35 percent. Advances in full-genome sequencing of HIV have led to the identification of circulating and unique recombinant forms (CRFs and URFs, respectively). These are the result of recombination between subtypes within a dually infected person, from whom the recombinant forms are then passed to other people. The recombinant progeny are classified as circulating recombinant forms if they are identified in three or more people with no direct epidemiologic linkage; otherwise they are described as unique recombinant forms.

In one embodiment, said immunogen has an amino acid sequence comprising at least one sequence selected from the group consisting of the SEQ ID NOs 1-16 or variants thereof, wherein said proviso ii) is: when the immunogen comprises only one sequence selected from the group consisting of SEQ ID NOs 1-16, then this sequence is not selected from the group consisting of SEQ ID NOs 1-16.

In a preferred embodiment, said immunogen comprises at least two, at least three, or at least four sequences selected from the group consisting of the SEQ ID NOs 1-16 or variants thereof, wherein said proviso ii) is: when the immunogen comprises only two, three, or four sequences selected from the group consisting of SEQ ID NOs 1-16, then not all of these sequences are selected from the group consisting of SEQ ID NO: 3, 5, 6 and 16. In another embodiment, said immunogen has an amino acid sequence comprising at least two, at least three, at least four, at least five, at least six, at least seven, at least eight, at least nine, or at least ten sequences selected from the group consisting of the SEQ ID NOs 1-16 or variants thereof, wherein said proviso ii) is: when the immunogen comprises only two, three, four, five, six, seven, eight, nine or ten sequences selected from the group consisting of SEQ ID NOs 1-16, then not all of these sequences are selected from the group consisting of SEQ ID NOs 1-16.

In a preferred embodiment, the immunogen according to the first aspect comprises the sequences according to SEQ ID NOs 1-16 or variants thereof in the order 1-16.

In one embodiment, the invention relates to the immunogen of the first aspect wherein at least two sequences are adjoined by an amino acid linker.

In another embodiment, the invention relates to the immunogen of the second aspect, wherein, if said immunogen comprises at least two sequences selected from the group consisting of the SEQ ID NOs 1-16 or variants thereof, said sequences are adjoined by an amino acid linker.

In a preferred embodiment of the immunogens of both the first and second aspect, the linker has the amino acid sequence A, AA or AAA. In a another embodiment, when the C-terminal residue of the sequence located N-terminally with respect to the linker or the N-terminal residue of the sequence located C-terminally is an alanine residue, the linker can be shortened so that an AAA sequence is formed in the junction region between adjoining sequences. Thus, in a preferred embodiment, if the C-terminal residue of the sequence located N-terminally with respect to the linker is an alanine or if the N-terminal residue of the sequence located C-terminally with respect to the linker is alanine, the linker has the sequence AA. In another embodiment, if the C-terminal residue of the sequence located N-terminally with respect to the linker and the N-terminal residue of the sequence located C-terminally with respect to the linker are both alanine, then the linker as the sequence A.

In another embodiment, said immunogens further comprise a secretion signal peptide at the N-terminus, wherein said signal peptide preferably enhances secretion of the immunogen from cells expressing said immunogen. A preferred secretion signal peptide is derived from GMCSF (granulocyte macrophage colony-stimulating factor), preferably followed by a valine to increase stability. The sequence of the GMCSF signal peptide is preferably: MWLQSLLLLGTVACSIS (SEQ ID NO: 46) or MWLQSLLLLGTVACSISV (SEQ ID NO: 47).

In another embodiment, said immunogens further comprise optionally a peptide tag. The peptide tag can be located at the N-terminus between the signal peptide and the immunogenic polypeptide or, preferably, can be located at the C-terminus before the stop codon.

Preferably, said tag is a FLAG peptide. The FLAG system utilizes a short, hydrophilic 8-amino acid peptide, which is fused to the recombinant protein of interest. The FLAG peptide includes the binding site for several highly specific ANTI-FLAG monoclonal antibodies (M1, M2, M5; Sigma-Aldrich Corp., Saint Louis, Mo., US), which can be used to assess expression of the protein of interest on material from transfected cells. Because of the small size of the FLAG peptide tag, it does not shield other epitopes, domains, or alter the function, secretion, or transport of the fusion protein generally. Preferably, said FLAG peptide has the sequence DYKDDDDKL (SEQ ID NO: 48).

In a preferred embodiment, said tag is only for expression analysis and purification of the immunogen and it is removed before using it to elicit an immune response.

In another embodiment, the invention relates to said immunogens, wherein said amino acid sequence comprises at least one antiretroviral resistance mutation site.

The mutation can occur at any site within the viral genome. Preferably, the mutation occurs in the region encoding the integrase, the protease or the reverse transcriptase genes.

Mutants within the integrase that confer resistance to integrase inhibitors include, without limitation, T66, E92, F121, E138, G140, Y143, S147, Q148, S153, N155, E157 and R263 within SEQ ID NO: 1 and a combination thereof. In a preferred embodiment, the mutation is selected from the group consisting of mutations E92Q, G140S, G 140A and Y143R in the integrase protein and their combinations.

Mutants within the protease associated with protease inhibitor (PI) resistance include major protease, accessory protease, and protease cleavage site mutations. See Shafer R, et al., AIDS Rev. 2008; 10(2):67-84. Seventeen largely non-polymorphic positions are of the most clinical significance, including L23I, L24I, D30N, V32I, L33F, M46I/L, 147/V/A, G48V/M, I50L/V, F53L, I54V/T/A/L/M, G73S/T, L76V, V82A/T/F/S, I84V/A/C, N88D/S, L90M. Accessory protease mutations include the polymorphic mutations L10I/V, 113V, K20R/M/I, M36I, D60E, 162V, L63P, A71V/T, V77I, and I93L and the non-polymorphic mutations L10F/R, V11I, E34Q, E35G, K43T, K45I, K55R, Q58E, A71I/L, T74P/A/S, V75I, N83D, P79A/S, I85V, L89V, T91S, Q92K and C95F.

In another embodiment, the antiretroviral resistance mutation site is located in the reverse transcriptase, resulting in a resistance to nucleoside reverse transcriptase inhibitor (NRTI) or to non-nucleoside reverse transcriptase inhibitor (NNRTI). The NRTI resistance mutations include M184V, thymidine analog mutations (TAMs), mutations selected by regimens lacking thymidine analogs (Non-TAMs), and multi-nucleoside resistance mutations (Multi-NRTI mutations) and many recently described non-polymorphic accessory mutations. Altogether, M184V, non-thymidine-analog-associated mutations such as K65R and L74V, and the multi-nucleoside resistance mutation Q151M act by decreasing NRTI incorporation. Thymidine analog mutations, the T69 insertions associated with multi-nucleoside resistance, and many of the accessory mutations facilitate primer unblocking. See Shafer, 20008, supra. M184V is the most commonly occurring NRTI resistance mutation. The most common drug-resistant amino acid mutations are M41L, D67N, K70R, L210W, T215Y/F and K219QE. The most common mutations in patients developing virologic failure while receiving a non-thymidine analog containing NRTI backbone (Non-TAMs) include M184V alone or M184V in combination with K65R or L74V. Other Non-TAMs mutations include K65N, K70E/G, L74I, V75T/M, Y115F. Amino acid insertions at codon 69 generally occur in the presence of multiple TAM, and in this setting are associated with intermediate resistance to 3TC and FTC and high-level resistance to each of the remaining NRTI. Q151 M is a 2-bp mutation (CAG.fwdarw.ATG) that is usually accompanied by two or more of the following mutations: A62V, V75I, F77L, and F116Y. The Q151M complex causes high-level resistance to ZDV, d4T, ddI, and ABC, and intermediate resistance to TDF, 3TC, and FTC. See Shafer R, et al., AIDS Rev. 2008; 10(2):67-84

NNTRI resistance mutations include, without limitation, the primary NNRTI resistance mutations (K103N/S, V106A/M, Y181C/I/V, Y188L/C/H, and G190A/S/E), the NNRTI resistance secondary mutations (L100I, K101P, P225H, F227L, M230L, and K238T) and rate mutations (V179F, F227C and L234I).

Minor non-polymorphic mutations—A98G, K101 E, V 108I, and V 179D/E are common NNRTI resistance mutations that reduce susceptibility to nevirapine and efavirenz about 2-fold to 5-fold.

Miscellaneous nonnucleoside reverse transcriptase inhibitor resistance mutations, such as K101Q, I135T/M, V179I, and L283I, reduce susceptibility to nevirapine and efavirenz by about twofold and may act synergistically with primary NNRTI resistance mutations. Other mutations such as L74V, H221Y, K223E/Q, L228H/R, and N348I are selected primarily by NRTI, yet also cause subtle reductions in NNRTI susceptibility.

Preferably, said antiretroviral resistance mutation site is located in any of SEQ ID NOs 9-11. More preferably, said antiretroviral resistance mutation site is amino acid residue 8 of SEQ ID NO: 9, wherein the amino acid Leu is substituted by the amino acid Met.

In another embodiment, the variant or fragment has a length of 8 to 40 amino acids, more preferably a length of 11 to 27 amino acids. Preferably, said variant or fragment does not comprise an amino acid linker adjoining any of SEQ ID NOs 1-16. Furthermore, it is preferred that the C-terminal amino acid of said variant or fragment is neither G, P, E, D, Q, N, T, S, nor C, as these residues do not form a C terminal anchor for HLA class I restricted T cell epitopes generally.

In a most preferred embodiment, said variant or fragment is selected from the group consisting of the peptides according to SEQ ID NOs 17-45.

Further, it is envisaged that said variant or fragment is combined with or fused to a heat shock protein. The present invention also relates to a fusion protein comprising said variant or fragment and a heat shock protein. Preferred heat shock proteins are Hsp10, Hsp20, Hsp30, Hsp40, Hsp60, Hsp70, Hsp90, gp96, or Hsp100.

In another embodiment, the variant or fragment is a variant or fragment according to the first and second aspects. Preferably, said variant or fragment does not comprise an amino acid linker adjoining any of SEQ ID NOs 1-16. Furthermore, it is preferred that the C-terminal amino acid of said variant or fragment is neither G, P, E, D, Q, N, T, S, nor C, as these residues do not form a C terminal anchor for HLA class I restricted T cell epitopes generally.

In a most preferred embodiment, said variant or fragment is selected from the group consisting of the peptides according to SEQ ID NOs 17-45.

Further, it is envisaged that said variant or fragment is combined with or fused to a heat shock protein. The present invention also relates to a fusion protein comprising said variant or fragment and a heat shock protein. Preferred heat shock proteins are Hsp10, Hsp20, Hsp30, Hsp40, Hsp60, Hsp70, Hsp90, gp96, or Hsp100.

3. Nucleic Acids, Vectors, Viruses and Cells of the Invention

In a third aspect, the present invention relates to a nucleic acid encoding for the immunogen of the first aspect, and to an expression cassette, a vector, a virus and a cell comprising said nucleic acid.

Preferably, said nucleic acid is a polynucleotide, referring to single-stranded or double-stranded polymers of nucleotide monomers (nucleic acids), including, but not limited to, 2'-deoxyribonucleotides (DNA) and ribonucleotides (RNA) linked by internucleotide phosphodiester bond linkages. The polynucleotides of the invention encode the immunogen of the invention without substantially comprising additional regions of the HIV genome.

In one embodiment, said nucleic acid is codon optimized. In a preferred embodiment, the nucleic acid is codon optimized for expression in humans. Codon-optimized nucleic acids for use according to the present invention can be prepared by replacing the codons of the nucleic acid encoding the immunogen by “humanized” codons (i.e. the codons are those that appear frequently in highly expressed human genes). See André S, et al., J. Virol. 1998; 72:1497-1503. In a preferred embodiment, said codon-optimized nucleic acid has the sequence according to SEQ ID NO: 50.

The nucleic acid of the third aspect may require cutting with restriction enzymes in order to it ligate into a vector. This procedure could entail the removal of various terminal nucleotides (e.g. 1, 2, or 3). As such, in one embodiment, the invention relates to said nucleic acid, wherein it has been cut at each end with a restriction enzyme.

In another embodiment, the present invention relates to an expression cassette comprising the nucleic acid of the third aspect, a promoter sequence and a 3'-UTR and optionally a selection marker. Preferably, the promoter sequence is a human cytomegalovirus (CMV) promoter or an early-late p7.5 promotor sequence. Preferably, the 3'-UTR is a bovine growth hormone (BGH) poly-A. The optional selection marker is an antibiotic resistance gene (e.g. kanamycin, ampicilin, tetracycline, spectinomycin) preferably.

In yet another embodiment, the present invention relates to an expression vector comprising the nucleic acid or the expression cassette of the third aspect.

In one embodiment, the vector is an expression vector. Thus, suitable vectors according to the present invention include prokaryotic vectors, such as pUC18, pUC19, and Bluescript plasmids and derivatives thereof, like the mp18, mp19, pBR322, pMB9, ColE1, pCR1 and RP4 plasmids; phages and shuttle vectors, such as pSA3 and pAT28 vectors; expression vectors in yeasts, such as 2-micron plasmid type vectors; integration plasmids; YEP vectors; centromeric plasmids and analogues; expression vectors in insect cells, such as the vectors of the pAC series and of the pVL series; expression vectors in plants, such as vectors of the pIBI, pEarleyGate, pAVA, pCAMBIA, pGSA, pGWB, pMDC, pMY, pORE series and analogues; and expression vectors in superior eukaryotic cells either based on viral vectors (e.g. MVA, adenoviruses, viruses associated to adenoviruses, retroviruses and lentiviruses) as well as non-viral vectors, such as the pSilencer 4.1-CMV (Ambion®, Life Technologies Corp., Carslbad, Calif., US), pcDNA3, pcDNA3.1/hyg pHCMV/Zeo, pCR3.1, pEF1/His, pIND/GS, pRc/HCMV2, pSV40/Zeo2, pTRACER-HCMV, pUB6/V5-His, pVAX1, pZeoSV2, pCI, pSVL and pKSV-10, pBPV-1, pML2d and pTDT1 vectors.

In a particular embodiment the expression vector is a mammalian expression vector comprising a mammalian promoter and a polyadenylation site. Preferably, the promoter is the human cytomegalovirus (CMV) promoter. Preferably, the polyadenylation site is the bovine growth hormone (BGH) polyadenylation site. The mammalian expression vector can be modified to optimize vector replication in bacteria. The mammalian expression vector can further comprise a selection gene, for example, a gene coding a protein conferring resistance to an antibiotic. In a particular embodiment, the mammalian expression vector comprises a kanamycin resistance gene.

In other particular embodiment, the expression vector is a viral vector, preferably a Modified Vaccine Ankara (MVA) virus vector.

In another embodiment, the present invention relates to a virus containing the nucleic acid of the third aspect. Suitable viruses are safe, have low toxicity and are genetically stable. Non-limiting examples are retroviruses, particularly poxviruses such as MVA, lentiviruses, adenoviruses and adeno-associated viruses (AAVs).

In a further particular preferred embodiment the present invention relates to a recombinant Modified Vaccinia virus Ankara (MVA) comprising in a polynucleotide or gene construct encoding the immunogenic polypeptides of the invention. Modified Vaccinia Ankara (MVA) virus is related to the vaccinia virus, a member of the genera orthopoxvirus in the family of poxyiridae. MVA has been generated by 516 serial passages on chicken embryo fibroblasts of the Ankara strain of vaccinia virus (CVA). See Mayr A, et al., Infection 1975; 3:6-14 and Sutter G, et al., U.S. Pat. No. 6,440,422 and CH 568,392. MVA viruses are publicly available (e.g. ATCC accession number VR-1508). MVA is distinguished by its attenuation (e.g. diminished virulence and limited ability to reproduce infectious virions in certain mammalian cells), while maintaining good immunogenicity and full capacity to replicate and produce infectious virions in avian cells. Suitable MVA strains include strains with enhanced safety due to i) capability of reproductive replication in vitro in chicken embryo fibroblasts (CEF), but no capability of reproductive replication in a human cell line, as in the human keratinocyte cell line HaCaT, the human embryo kidney cell line 293, the human bone osteosarcoma cell line 143B, and the human cervix adenocarcinoma cell line HeLa; ii) failure to replicate in a mouse model that is incapable of producing mature B and T cells and as such is severely immune compromised and highly susceptible to a replicating virus; and iii) induction of at least the same level of specific immune response in vaccinia virus prime/vaccinia virus boost regimes when compared to DNA-prime/vaccinia virus boost regimes. A suitable attenuated MVA strain in the strain referred to as MVA-BN. See Chaplin P, et al., WO2002042480, ECACC accession number V00083008.

In another embodiment, the present invention relates to a cell comprising the nucleic acid, the expression cassette, the expression vector, or the virus of the third aspect. Cells to be used can be of any cell type, including both eukaryotic cells and prokaryotic cells. Preferably, the cells include prokaryotic cells, yeast cells, or mammalian cells. Preferred examples of mammalian cells are COS cells, HeLa cells, HEK 293T cells or cells isolated from a patient (e.g. a HIV patient).

4. Compositions of the Invention

In a fourth aspect, the present invention relates to a composition comprising a variant or fragment according to the first and second aspects and a heat shock protein. Immunogenic compositions can be prepared, for instance, as injectables such as liquid solutions, suspensions, and emulsions. Preferred heat shock proteins are Hsp10, Hsp20, Hsp30, Hsp40, Hsp60, Hsp70, Hsp90, gp96, or Hsp100.

Furthermore, the invention relates to a pharmaceutical composition comprising an immunogen, nucleic acid, expression cassette, vector or cell according to the invention or a composition according to the fourth aspect and a pharmaceutically acceptable carrier. In one embodiment, said pharmaceutical compositions and the composition of the fourth aspect may be used as a vaccine, as laid out below.

5. Vaccine of the Invention

In another aspect, the present invention relates to a vaccine comprising the immunogen of the first and second aspects, the nucleic acid, the expression cassette, the expression vector, the virus or the cell of the third aspect or the composition of the fourth aspect.

In a preferred embodiment, said vaccine is capable of generating cellular and humoral responses. More preferably, the vaccine generates a cytotoxic T cell response. A cytotoxic T cell or cytotoxic T lymphocyte (CTL) assay can be used to monitor the cellular immune response following subgenomic immunization with a viral sequence against homologous and heterologous HIV strains. See Burke S, et al., J. Inf. Dis. 1994; 170:1110-1119 and Tigges M, et al., J. Immunol, 1996; 156:3901-3910. Conventional assays utilized to detect T cell responses include, for instance, proliferation assays, lymphokine secretion assays, direct cytotoxicity assays and limiting dilution assays. For example, antigen-presenting cells that have been incubated with a peptide can be assayed for their ability to induce CTL responses in responder cell populations. Antigen-presenting cells can be cells such as peripheral blood mononuclear cells (PBMCs) or dendritic cells (DCs). Alternatively, mutant non-human mammalian cell lines that are deficient in their ability to load MHC class I molecules with internally processed peptides and that have been transfected with the appropriate human MHC class I gene, can be used to test the capacity of a peptide of interest to induce in vitro primary CTL responses. PBMCs can be used as the responder cell source of CTL precursors. The appropriate antigen-presenting cells are incubated with the peptide after which the protein-loaded antigen-presenting cells are incubated with the responder cell population under optimized culture conditions. Positive CTL activation can be determined by assaying the culture for the presence of CTL that kill radiolabeled target cells, both specific peptide-pulsed targets as well as target cells expressing endogenously processed forms of the antigen from which the peptide sequence was derived. For example, the target cells can be radiolabeled with $^{51}$Cr and cytotoxic activity can be calculated from radioactivity released from the target cells. Another suitable method allows the direct quantification of antigen-specific T cells by staining with fluorescein-labeled HLA tetrameric complexes. See Altman J, et al., Proc. Natl. Acad. Sci. USA 1993; 90:10330-10334 and Altman J, et al., Science 1996; 274:94-96. Other relatively recent technical developments include staining for intracellular lymphokines and interferon release assays or ELISpot assays.

In one embodiment, the vaccine of the fourth aspect further comprises one or more adjuvants or heat shock proteins.

Adjuvants are defines as above. Preferred heat shock proteins are Hsp10, Hsp20, Hsp30, Hsp40, Hsp60, Hsp70, Hsp90, gp96, or Hsp100.

6. Therapeutic Methods

In a preferred embodiment, the immunogenic polypeptide according to the invention, the nucleic acid of the invention, the expression cassette of the invention, the expression vector of the invention, the virus of the invention, the cell of the invention or the vaccine according to the invention can be used in the prevention or treatment of an HIV infection or a disease associated with an HIV infection.

Thus, in another aspect, the invention relates to the immunogenic polypeptide according to the invention, the nucleic acid of the invention, the expression cassette of the invention, the expression vector of the invention, the virus of the invention, the cell of the invention or the vaccine according to the invention for use in the prevention or treatment of an HIV infection or a disease associated with an HIV infection.

In another aspect, the invention relates to the use of the immunogenic polypeptide according to the invention, the nucleic acid of the invention, the expression cassette of the invention, the expression vector of the invention, the virus of the invention, the cell of the invention or the vaccine according to the invention for the manufacture of a medicament for the prevention or treatment of an HIV infection or a disease associated with an HIV infection.

In another aspect, the invention relates to a method for the prevention or treatment of an HIV infection or a disease associated with an HIV in a subject in need thereof comprising the administration to said subject of the immunogenic polypeptide according to the invention, the nucleic acid of the invention, the expression cassette of the invention, the expression vector of the invention, the virus of the invention, the cell of the invention or the vaccine according to the invention for the manufacture of a medicament for the prevention or treatment of an HIV infection or a disease associated with an HIV infection.

In a particular embodiment, the immunogenic peptide, the nucleic acid, the expression cassette the expression vector, the virus, the cell or the vaccine for use according to the invention, comprises the sequential administration of:
i) a first immunogenic peptide of any of claims 1-11, nucleic acid of any of claims 12-14, expression cassette of claim 15, expression vector of claim 16, virus of any of claims 17-18, cell of claim 19 or vaccine of claim 20 and
ii) a second immunogenic peptide of any of claims 1-11, nucleic acid of any of claims 12-14, expression cassette of claim 15, expression vector of claim 16, virus of any of claims 17-18, cell of claim 19 or vaccine of claim 20.

In a particular embodiment, the first the first immunogenic peptide, nucleic acid, expression cassette, expression vector, virus, cell or vaccine are different from the second immunogenic peptide, nucleic acid, expression cassette, expression vector, virus, cell or vaccine. Preferably, it is first administered an expression vector according to the invention followed by the administration of a Modified Vaccinia Ankara virus according to the invention.

In a particular embodiment, the first expression vector according to the invention is administered at least twice, preferably at least three times.

The beneficial prophylactic or therapeutic effect of vaccine in relation to HIV infection or AIDS symptoms include, for example, preventing or delaying initial infection of an individual exposed to HIV; reducing viral burden in an individual infected with HIV; prolonging the asymptomatic phase of HIV infection; maintaining low viral loads in HIV infected patients whose virus levels have been lowered via antiretroviral therapy (ART); increasing levels of CD4 T cells or lessening the decrease in CD4 T cells, both HIV-1 specific and non-specific, in drug naive patients and in patients treated with ART, increasing the breadth, magnitude, avidity and functionality of HIV specific CTL, increasing overall health or quality of life in an individual with AIDS; and prolonging life expectancy of an individual with AIDS. A clinician can compare the effect of immunization with the patient's condition prior to treatment, or with the expected condition of an untreated patient, to determine whether the treatment is effective in inhibiting AIDS.

Preferably, said disease is AIDS, ARC or an HIV opportunistic disease. Non-limiting examples for HIV opportunistic diseases are Burkitt's lymphoma, candidiasis in the bronchi, trachea, lungs, or esophagus, cervical cancer, coccidioidomycosis (disseminated or outside the lungs), cryptococcosis (outside the lungs), cryptosporidiosis (in the intestines lasting for more than 1 month), cytomegalovirus infection (outside the liver, spleen, or lymph nodes), cytomegalovirus retinitis (with loss of vision), HIV encephalopathy, herpes simplex lesions lasting for more than one month, herpes simplex in the bronchi, lung, or esophagus, histoplasmosis (disseminated or outside the lungs), immunoblastic lymphoma, invasive cervical carcinoma (cancer), isosporiasis in the intestines lasting for more than one month, Kaposi's sarcoma, lymphoma (primary in the brain), *Mycobacterium avium* complex (disseminated or outside the lungs), *Mycobacterium kansasii* (disseminated or outside the lungs), *Mycobacterium tuberculosis* (disseminated or outside the lungs), *Pneumocystis carinii pneumonia*, pneumonia (recurrent in 12 month period), progressive multifocal leukoencephalopathy (PML), salmonella septicemia (recurrent), toxoplasmosis (in the brain), wasting syndrome and any other disease resulting from an infection facilitated by a compromised immune system in an HIV-infected patient.

The vaccine of the invention may be useful for the therapy of HIV-1 infection. While all animals that can be afflicted with HIV-1 or their equivalents can be treated in this manner (e.g. chimpanzees, macaques, baboons or humans), the immunogenic compositions of the invention are directed particularly to their therapeutic uses in humans. Often, more than one administration may be required to bring about the desired therapeutic effect; the exact protocol (dosage and frequency) can be established by standard clinical procedures.

The present invention further relates to preventing or reducing symptoms associated with HIV infection. These include symptoms associated with the minor symptomatic phase of HIV infection, including, for example, shingles, skin rash and nail infections, mouth sores, recurrent nose and throat infection and weight loss. In addition, further symptoms associated with the major symptomatic phase of HIV infection include, for instance, oral and vaginal thrush (candidiasis), persistent diarrhea, weight loss, persistent cough and reactivated tuberculosis or recurrent herpes infections, such as cold sores (herpes simplex). Other symptoms of full-blown AIDS which can be treated in accordance with the present invention include, for instance, diarrhea, nausea and vomiting, thrush and mouth sores, persistent, recurrent vaginal infections and cervical cancer, persistent generalized lymphadenopathy (PGL), severe skin infections, warts and ringworm, respiratory infections, pneumonia, especially *Pneumocystis carinii* pneumonia (PCP), herpes zoster (or shingles), nervous system problems, such as pains, numbness or "pins and needles" in the hands and feet, neurological abnormalities, Kaposi's sarcoma, lymphoma, tuberculosis or other similar opportunistic infections.

Beneficial effects of the invention include, for example, preventing or delaying initial infection of an individual exposed to HIV, reducing viral burden in an individual infected with HIV, prolonging the asymptomatic phase of HIV infection, maintaining low viral loads in HIV infected patients whose virus levels have been lowered via antiretroviral therapy (ART), increasing levels of CD4 T cells or lessening the decrease in CD4 T cells, both HIV-1 specific and non-specific, in drug naive patients and in patients treated with ART, increasing the breadth, magnitude, avidity and functionality of HIV specific CTL, increasing overall health or quality of life in an individual with AIDS and prolonging life expectancy of an individual with AIDS. A clinician can compare the effect of immunization with the patient's condition prior to treatment, or with the expected condition of an untreated patient, or in a clinical trial of individuals treated and untreated with the vaccine to determine whether the treatment is effective in inhibiting AIDS.

The immunogenic compositions can be designed to introduce the nucleic acids or expression vectors to a desired site of action and release it at an appropriate and controllable rate. Methods of preparing controlled-release formulations are known in the art. For example, controlled release preparations can be produced by the use of polymers to complex or absorb the immunogen or immunogenic composition. A controlled-release formulation can be prepared using appropriate macromolecules (e.g. polyesters, polyamino acids, polyvinyl, pyrrolidone, ethylenevinylacetate, methylcellulose, carboxymethylcellulose, or protamine sulfate) known to provide the desired controlled release characteristics or release profile. Another possible method to control the duration of action by a controlled-release preparation is to incorporate the active ingredients into particles of a polymeric material (e.g. polyesters, polyamino acids, hydrogels, polylactic acid, polyglycolic acid, copolymers of these acids, or ethylene vinylacetate copolymers). Alternatively, instead of incorporating these active ingredients into polymeric particles, it is possible to entrap these materials into microcapsules prepared, for example, by coacervation techniques or by interfacial polymerization, for example, hydroxymethylcellulose or gelatin-microcapsule and poly-(methylmethacrylate) microcapsule, respectively, in colloidal drug delivery systems (e.g. liposomes, albumin microspheres, microemulsions, nano-particles, nanocapsules) or in macroemulsions. See in Voller A, et al., Eds., "New Trends and Developments in Vaccines (University Park Press, Baltimore, Md., US, 1978) and Gennaro A, Ed., "Remington's Pharmaceutical Sciences", 18th Ed. (Mack Publishing Co., Easton, Pa., US, 1990).

Suitable dosages of the nucleic acids and expression vectors of the invention (collectively, the immunogens) in the immunogenic composition of the invention can be readily determined by those of skill in the art. For example, the dosage of the immunogens can vary depending on the route of administration and the size of the subject. Suitable doses can be determined by those of skill in the art, for example by measuring the immune response of a subject, such as a laboratory animal, using conventional immunological techniques, and adjusting the dosages as appropriate. Such techniques for measuring the immune response of the subject include but are not limited to, chromium release assays, tetramer binding assays, IFN ELISPOT assays, IL-2 ELISPOT assays, intracellular cytokine assays, and other immunological detection assays. See Harlow E, Lane D, "Antibodies: A Laboratory Manual" (Cold Spring Harbor Laboratory Press, Cold Spring Harbor, N.Y., US, 1988).

The immunogenic compositions can be administered using any suitable delivery method including, but not limited to, intramuscular, intravenous, intradermal, transcutaneous, intranasal, mucosal (e.g. intrarectal, intravaginal, oral), and topical delivery. Such techniques are well known in the art. More specific examples of delivery methods are intramuscular injection, intradermal injection, and subcutaneous injection. However, delivery need not be limited to injection methods. Further, delivery of DNA to animal tissue has been achieved by cationic liposomes direct injection of naked DNA into animal muscle tissue or intradermal injection of DNA using "gene gun" or electroporation technology. See Watanabe M, et al., Mol. Reprod. Dev. 1994; 38:268-274, Charnock-Jones D, et al., WO1996020013, Robinson H, et al., Vaccine 1993: 11:957-960, Hoffman S, et al., Vaccine 1994; 12(16):1529-1533; Xiang Z, et al., Virology 1994; 199:132-140, Webster R, et al., Vaccine 1994; 12:1495-1498, Davis H, et al., Vaccine 1994; 12: 1503-1509, Davis H, et al., Hum. Mol. Gen. 1993; 2:1847-1851, and Johnston S, et al., Meth. Cell Biol. 1994; 43:353-365. Delivery can be accomplished via a mucosal surface such as the anal, vaginal or oral mucosa also.

7. Kit of the Invention

In another aspect, the present invention relates to a kit comprising the immunogen of the first aspect, the peptide or variant thereof of the second aspect, the nucleic acid, the expression cassette, the expression vector, the virus or the cell of the fourth aspect, or the vaccine of the fourth aspect. These kits provide the materials necessary for carrying out the application described in the present invention. The kit could also be in the form of a patch.

In addition, the kit may comprise a packaging, which allows maintaining the reagents within determined limits. Suitable materials for preparing such packings include glass, plastic (e.g. polyethylene, polypropylene, polycarbonate), bottles, vials, paper, or sachets. The kit of the invention can additionally contain instructions for using the components contained therein, in particularly those constituting the hemostatic patch of the invention. Said instructions can be found in the form of printed material or in the form of an electronic support which can store instructions such that they can be read by a subject, such as electronic storage media (e.g. magnetic disks, tapes), or optical media (e.g. CD-ROM, DVD). The media can additionally or alternatively contain internet websites providing said instructions.

General Procedures

1. T Cell Immunogen Design

The following approach was followed for the design of the HIV OLPs of the invention.

Experimental (interferon gamma ELISpot) screening of 232 HIV infected untreated individuals using a consensus clade B peptide set revealed regions of the viral proteome that were predominantly targeted by subjects with superior HIV control. See Frahm N, et al., J. Virol. 2004; 78:2187-2200; Mothe B, et al., J. Transl. Med. 2011; 9(1):208. The overall test peptide set consisted of 410 18mer overlapping peptides spanning the entire viral proteome. Of these, 26 OLPs were identified where the group of OLP responders had a significantly (p<0.05 uncorrected for multiple comparison) reduced viral load compared to the group of OLP non-responders (i.e. individuals that did not react to these OLPs in the interferon gamma ELISpot assay). These beneficial OLPs had a protective ratio (PR of >1) and were located in HIV Gag protein (n=10), in Pol (n=12), and in Vif (n=3) and Nef (n=1) proteins of the virus. Of the 26 OLPs, 15 were partially overlapping. See Table 1.

| OLP No. | Protein | Protein sub-unit | Protein OLP clade B consensus sequence | Median viral load in OLP responders | Median viral load in OLP non-responders | Protective Ratio (PR)* | p-value |
|---|---|---|---|---|---|---|---|
| 3 | Gag | p17 | EKIRLRPGGKKKYKLKHI | 22947 | 39014 | 1.053 | 0.037 |
| 6 | Gag | p17 | ASRELERFAVNPGLL | 15380 | 43189 | 1.107 | 0.001 |
| 7 | Gag | p17 | ERFAVNPGLLETSEGCR | 25939 | 38974 | 1.040 | 0.049 |
| 10 | Gag | p17 | QLQPSLQTGSEELRSLY | 16285 | 37237 | 1.085 | 0.031 |
| 12 | Gag | p17 | SLYNTVATLYCVHQRIEV | 23855 | 37113 | 1.044 | 0.037 |
| 23 | Gag | p24 | AFSPEVIPMFSALSEGA | 22947 | 37113 | 1.048 | 0.036 |
| 31 | Gag | p24 | IAPGQMREPRGSDIA | 3563 | 35483 | 1.281 | 0.028 |
| 34 | Gag | p24 | STLQEQIGWMTNNPPIPV | 6127 | 37360 | 1.207 | 0.002 |
| 48 | Gag | p24 | ACQGVGGPGHKARVLAEA | 12975 | 35755 | 1.107 | 0.041 |
| 60 | Gag | p15 | GKIWPSHKGRPGNFLQSR | 16266 | 36434 | 1.083 | 0.044 |
| 75 | Nef | — | WLEAQEEEVGFPVRPQV | 13407 | 37360 | 1.108 | 0.026 |
| 76 | Nef | — | EVGFPVRPQVPLRPMTYK | 59618 | 29855 | 0.937 | 0.001 |
| 84 | Nef | — | NYTPGPGIRYPLTFGWCF | 55402 | 30538 | 0.945 | 0.006 |
| 85 | Nef | — | RYPLTFGWCFKLVPV | 69890 | 29903 | 0.924 | 0.002 |
| 90 | Nef | — | SLHGMDDPEKEVLVWKF | 89687 | 32650 | 0.911 | 0.042 |
| 159 | Pol | Protease | KMIGGIGGFIKVRQYDQI | 14736 | 36434 | 1.094 | 0.020 |
| 160 | Pol | Protease | FIKVRQYDQILIEICGHK | 3682 | 35755 | 1.277 | 0.031 |
| 161 | Pol | Protease | QILIEICGHKAIGTVLV | 9117 | 35483 | 1.149 | 0.050 |
| 163 | Pol | Protease | LVGPTPVNIIGRNLLTQI | 25965 | 45637 | 1.055 | 0.007 |
| 171 | Pol | RT | LVEICTEMEKEGKISKI | 1865 | 35483 | 1.391 | 0.014 |
| 181 | Pol | RT | LDVGDAYFSVPLDKDFRK | 65858 | 32871 | 0.937 | 0.041 |
| 195 | Pol | RT | LRWGFTTPDKKHQKEPPF | 5624 | 37113 | 1.219 | 0.006 |
| 196 | Pol | RT | DKKHQKEPPFLWMGYELH | 10103 | 35483 | 1.136 | 0.044 |
| 210 | Pol | RT | EIQKQGQGQWTYQIY | 18155 | 35483 | 1.068 | 0.045 |
| 222 | Pol | RT | PPLVKLWYQLEKEPIVGA | 412599 | 34640 | 0.808 | 0.030 |
| 230 | Pol | RT | IHLALQDSGLEVNIV | 85102 | 34117 | 0.919 | 0.030 |

-continued

| OLP No. | Protein | Protein sub-unit | Protein OLP clade B consensus sequence | Median viral load in OLP responders | Median viral load in OLP non-responders | Protective Ratio (PR)* | p-value |
|---|---|---|---|---|---|---|---|
| 237 | Pol | RT | VYLAWVPAHKGIGGNEQV | 85102 | 34117 | 0.919 | 0.029 |
| 240 | Pol | RT | SAGIRKVLFLDGIDKA | 116902 | 32761 | 0.891 | 0.019 |
| 269 | Pol | Integrase | TKELQKQITKIQNFRVYY | 6629 | 35755 | 1.192 | 0.030 |
| 270 | Pol | Integrase | TKIQNFRVYYRDSRDPLW | 18171 | 37360 | 1.073 | 0.019 |
| 271 | Pol | Integrase | YYRDSRDPLWKGPAKLLW | 25939 | 35755 | 1.032 | 0.043 |
| 276 | Pol | Integrase | KIIRDYGKQMAGDDCVA | 6629 | 35755 | 1.192 | 0.021 |
| 279 | Vpr | — | GPQREPYNEWTLELLEEL | 60222 | 32650 | 0.944 | 0.042 |
| 307 | Env | gp120 | DLNNNTNTTSSSGEKMEK | 179419 | 34117 | 0.863 | 0.044 |
| 311 | Env | gp120 | IRDKVQKEYALFYKLDVV | 179419 | 32871 | 0.860 | 0.008 |
| 314 | Env | gp120 | YRLISCNTSVITQACPKV | 58206 | 31273 | 0.943 | 0.008 |
| 315 | Env | gp120 | SVITQACPKVSFEPIPIH | 61011 | 32871 | 0.944 | 0.034 |
| 320 | Env | gp120 | TNVSTVQCTHGIRPVV | 341587 | 34640 | 0.820 | 0.034 |
| 355 | Env | gp120 | VAPTKAKRRVVQREKRAV | 161602 | 34117 | 0.870 | 0.042 |
| 399 | Env | gp41 | VIEVVQRACRAILHIPRR | 388089 | 34640 | 0.812 | 0.026 |
| 405 | Vif | — | VKHHIMYISGKAKGWFYRH | 16458 | 37237 | 1.084 | 0.021 |
| 406 | Vif | — | GKAKGWFYRHHYESTHPR | 16458 | 37237 | 1.084 | 0.022 |
| 424 | Vif | — | TKLTEDRWNKPQKTKGHR | 10319 | 36434 | 1.137 | 0.014 |

*PR values in bold indicate PR > 1, i.e. OLP-responses seen more frequently in individuals with reduced viral loads.

In order to build a continuous immunogen sequence, the 26 OLPs were aligned and assembled to a total of 16 segments, ranging from 11-78 amino acids in length. The precise starting and end positions of these segments were based on analyzing residues in up and down-steam of the identified 26 OLPs and was based on a number of considerations that were applied to the different flanking sites. These considerations included:

1) OLP immunogenicity data
2) Conserved region reactivity data
3) Extension or chopping segments for inclusion/exclusion of good or bad known epitopes
4) CD4 epitope coverage
5) HLA coverage
6) Sequence variability (2010 consensus and HBX2 defined epitopes)
7) Multivariate OLP analyses
8) Creation of new epitope/self epitope
9) Maintenance of natural sequence though not included beneficial OLP
10) Introduction of changes to avoid epitope recognition and
11) Avoid forbidden residues (G, P, E, D, Q, N, T, S or C)

This protocol resulted in the design of SEQ ID NO: 1 to SEQ ID NO: 16 as potential immunogens.

2. Vectors

Sequences SEQ ID NO: 1 to SEQ ID NO: 16 were linked with single, dual or triple alanine amino acids between segments to ensure optimal processing and to avoid premature epitope digestion.

Then, the linked segments were used as HIV T cell immunogen sequences for inclusion in DNA and MVA vectors. For the delivery of the immunogens using either soluble peptides only or in combination with heat shock proteins, shorter overlapping peptides (median length 23 residues) were designed that span the 16 segments, not including the triple AAA linkers. These OLPs were generated in a way that helped avoid forbidden residues at the C-terminal end (important for optimal epitope presentation on HLA class I molecules. See SEQ ID NO: 17 to SEQ ID NO: 45, January 2012). These overlapping peptides range in length from 11-27 amino acids.

3. T Cell Immunogen

The T cell immunogen has been designed as a polypeptide and assembled from 16 segments of the HIV-1 genome of varying size (between 11 to 78 aa) unified by triple alanine linkers. Description of the regions included:

| T cell immunogen segments | Length | HIV-1 protein | Position (HXB2) | SEQ ID NO: |
|---|---|---|---|---|
| Seg-1 | 78 | p17 | 17-94 | 1 |
| Seg-2 | 14 | p24 | 30-43 | 2 |
| Seg-3 | 11 | p24 | 61-71 | 3 |
| Seg-4 | 60 | p24 | 91-150 | 4 |
| Seg-5 | 14 | p24 | 164-177 | 5 |
| Seg-6 | 15 | p24 | 217-231 | 6 |
| Seg-7 | 27 | p2p7p1p6 | 63-89 | 7 |
| Seg-8 | 55 | protease | 45-99 | 8 |
| Seg-9 | 17 | RT | 34-50 | 9 |
| Seg-10 | 55 | RT | 210-264 | 10 |
| Seg-11 | 34 | RT | 309-342 | 11 |
| Seg-12 | 34 | Integrase | 210-243 | 12 |
| Seg-13 | 17 | Integrase | 266-282 | 13 |
| Seg-14 | 23 | Vif | 25-50 | 14 |
| Seg-15 | 19 | Vif | 166-184 | 15 |
| Seg-16 | 13 | Nef | 56-68 | 16 |

Total length: 529 (including A, AA or AAA linkers)

4. Inclusion of a Leader Sequence

Signal peptides are generally highly hydrophobic amino acid sequences (15 to 60 amino acids long) of proteins that must cross through membranes to arrive at their functioning cellular location. By binding to signal recognition particles, these sequences direct nascent protein-ribosome complexes to a membrane where the protein is inserted during translation. Signal peptides direct translational uptake of the protein by various membranes (e.g. endoplasmic reticulum, mitochondria, chloroplast, peroxisome). Leader signal sequences on non-membrane proteins are ultimately removed by specific peptidases.

Some signal peptides used include MCP-3 chemokine, for promoting secretion and attraction of antigen presenting cells; a catenin (CATE)-derived peptide for increased proteasomal degradation; and the lysosomal associated protein, LAMP1 for targeting the MHC II compartment. See Rosati M, et al., Proc. Natl. Acad. Sci. USA 2009; 106:15831-15836.

In the present design, the signal peptide from GMCSF (granulocyte macrophage colony-stimulating factor) was introduced at the amino-terminus of the immunogen to enhance secretion of the immunogen from expressing cells, followed by a valine to increase stability. The sequence of the GMCSF signal peptide is:

```
                                        (SEQ ID NO: 46)
MWLQSLLLLGTVACSIS
```

5. Inclusion of a Tag for In-Vitro Expression Experiments

For the purpose of assessing expression in transfected cells, the immunogen sequence first included a FLAG peptide on the C-terminal region, before the stop codon, was:

```
                                        (SEQ ID NO: 48)
DYKDDDDKL
```

The FLAG system utilizes a short, hydrophilic 8-amino acid peptide, which is fused to the recombinant protein of interest. The FLAG peptide includes the binding site for several highly specific ANTI-FLAG monoclonal antibodies (M1, M2, M5; Sigma-Aldrich Corp., Saint Louis, Mo., US), which can be used to assess expression of the protein of interest on material from transfected cells.

Because of the small size of the FLAG peptide tag, it does not shield other epitopes, domains, or alter the function, secretion, or transport of the fusion protein generally. This sequence was removed afterwards for the mice immunogenicity assay. The FLAG tag is removed from the final immunogen (298H) before immunization.

6. Description of the T Cell Immunogen

The T cell immunogen has the following sequence (SEQ ID NO: 49):

M W L Q S L L L L G T V A C S I S V (E K I R L

R P G G K K K Y K L K H I V W A S R E L E R F A

V N P G L L E T S E G C R Q I L G Q L Q P S L Q

T G S E E L K S L Y N T V A T L Y C V H Q K I E

V)$_{S1}$ A A A (K A F S P E V I P M F S A L)$_{S2}$ A A A

(G H Q A A M Q M L K E)$_{S3}$ A A A (I A P G Q M R E

P R G S D I A G T T S T L Q E Q I G W M T N N P

P I P V G E I Y K R W I I L G L N K I V R M Y S

P T S I)$_{S4}$ A A A (Y V D R F Y K T L R A E Q A)$_{S5}$

A (A C Q G V G G P G H K A R V L)$_{S6}$ A A A (C T E

R Q A N F L G K I W P S H K G R P G N F L Q S

R)$_{S7}$ A A A (K M I G G I G G F I K V R Q Y D Q I

L I E I C G H K A I G T V L V G P T P V N I I G

R N L L T Q I G C T L N F)$_{S8}$ A A A (L V E I C T

E M E K E G K I S K I)$_{S9}$ A A A (L R W G F T T P

D K K H Q K E P P F L W M G Y E L H P D K W T V

Q P I V L P E K D S W T V N D I Q K L V G K L)$_{S10}$

A A A (I L K E P V H G V Y Y D P S K D L I A E

I Q K Q G Q G Q W T Y Q I Y)$_{S11}$ A A A (T K E L Q

K Q I T K I Q N F R V Y Y R D S R D P L W K G P

A K L L W)$_{S12}$ A A A (K I I R D Y G K Q M A G D D

C V A)$_{S13}$ A A (V K H H M Y I S K K A K G W F Y R

H H Y E S T H P R)$_{S14}$ A A A (V T K L T E D R W N

K P Q K T K G H R)$_{S15}$ A A (A W L E A Q E E E E V

G F)$_{S16}$ D Y K D D D D K L wherein, the GMCSF signal peptide is shown underlined, the valine immediately following the signal sequence is highlighted, the single, dual or triple A (AAA) linkers are shown in bold, the FLAG epitope (removed in the final construct for in-vivo studies) is shown in italics and the different segments are shown in brackets as follows:

| Segment number | HIV polypeptide | HIV gene |
|---|---|---|
| (...) s1 | p17 (Seg-1) | gag |
| (...) S2-6 | p24 (Seg-2 to Seg-6) | gag |
| (...) S7 | p2p7p1p6 (Seg-7) | gag |
| (...) S8 | Prot (seg-8) | pol |
| (...) S9-11 | RT (Seg-9 to Seg-11) | pol |
| (...) S12-13 | Int (Seg-12 and Seg-13) | pol |
| (...) S14-15 | Vif (Seg-14 and Seg-15) | Vif |
| S16 | Nef(Seg-16) | Nef |

7. Nucleotide Sequence Codon Optimization

The T cell immunogen sequence was translated into a RNA/codon-optimized nucleotide sequence to enhance expression and secretion (Mr. Gene GmbH, Regensburg, DE). Codon optimization was based on introducing multiple nucleotide changes to destroy the previously identified RNA processing, inhibitory and instability sequences in the mRNA without affecting the encoded protein. See Schwartz S, et al., J. Virol. 1992; 66(12): 7176-7182. This process can also include the elimination of predicted splice sites (score >0.4) from coding sequences by appropriate codon changes, to minimize the possibility of splicing.

As a result of the nucleotide changes indicated above, the final GC-content of the T cell immunogen was 63%. The complete codon-optimized nucleotide sequence of the immunogen is (SEQ ID NO: 50):

```
   1  ATGTGGCCTCC AGAGCCTGCT ACTCCTGGGG ACGGTGGCCT CAGCATCTC  GGTCGAGAAG
  61  ATCCGGCTGC  GGCCAGGCGG AAAGAAGAAG TACAAGCTGA AGCACATCGT CTGGGCCTCG
 121  AGGGAGCTGG  AGCGGTTCGC GGTGAACCCG GGACTTCTGG AGACGTCGGA GGGGTGCAGG
 181  CAGATCCTCG  GCCAGCTGCA GCCCTCTCTG CAAACGGGGT CTGAGGAGCT GAAGAGCCTG
 241  TACAACACGG  TGGCGACCCT CTACTGCGTC CACCAGAAGA TCGAGGTGGC AGCGGCCAAG
 301  GCGTTCTCGC  GGAGGTCAT  CCCCATGTTC TCGGCGCTGG CAGCTGCCGG ACACCAGGCC
 361  GCGATGCAGA  TGCTGAAGGA GGCCGCTGCG ATCGCACCGG CCAGATGAG  GGAGCCACGC
 421  GGTTCCGACA  TCGCGGGAAC CACCTCGACG CTCCAGGAGC AGATCGGATG GATGACGAAC
 481  AACCCGCCAA  TCCCGGTCGG GGAGATCTAC AAGCGGTGGA TCATCCTCGG GCTGAACAAG
 541  ATCGTCCGGA  TGTACAGCCC GACGTCGATC GCTGCGGCAT ACGTTGACCG GTTCTACAAG
 601  ACCCTGAGGG  CCGAGCAGGC AGCGGCCTGC CAGGGGGTCG GTGGACCAGG GCACAAGGCC
 661  CGAGTGCTCG  CGGCCGCATG CACGGAGCGG CAGGCGAACT TCCTGGGGAA GATCTGGCCG
 721  TCGCACAAGG  GCCGACCGGG AAACTTCCTC CAGTCTCGCG CAGCGGCTAA GATGATCGGA
 781  GGCATCGGAG  GCTTCATCAA AGTCCGTCAG TACGACCAGA TCCTCATCGA GATCTGCGGG
 841  CACAAGGCGA  TCGGAACCGT GCTCGTCGGC CCAACGCCCG TGAACATCAT CGGCCGCAAC
 901  CTGTTAACGC  AGATCGGCTG CACCCTCAAC TTCGCCGCAC TAGTGGAGAT CTGCACGGAG
 961  ATGGAGAAGG  AGGGCAAGAT ATCGAAGATC GCGGCAGCTC TGAGGTGGGG CTTCACCACG
1021  CCGGACAAGA  AGCACCAGAA GGAGCCGCCA TTCCTGTGGA TGGGATACGA GCTGCACCCG
1081  GACAAGTGGA  CCGTGCAGCC CATCGTCCTG CCGGAGAAGG ACTCGTGGAC GGTGAACGAC
1141  ATCCAGAAGC  TCGTGGGGAA GCTGGCGGCA GCCATCCTCA AGGAGCCCGT CCACGGGGTG
1201  TACTACGACC  CCTCTAAGGA CCTGATCGCG GAGATCCAGA AGCAGGGGCA GGGTCAGTGG
1261  ACCTACCAGA  TCTACGCAGC AGCAACCAAG GAGCTGCAGA AGCAGATCAC GAAGATCCAG
1321  AACTTCCGCG  TATACTACCG CGACTCGCGG GACCCCCTGT GGAAGGGCCC TGCGAAGCTT
1381  CTCTGGGCAG  CCGCGAAGAT CATCCGGGAC TACGGCAAGC AGATGGCGGG CGACGACTGC
1441  GTGGCCGCAG  CGGTGAAGCA CCATATGTAC ATCTCGAAGA AGGCGAAGGG CTGGTTCTAC
1501  AGACACCACT  ACGAGTCCAC CCACCCCAGG GCAGCTGCGG TGACGAAGCT GACGGAGGAC
1561  CGGTGGAACA  AGCCCCAGAA GACGAAGGGT CACCGGGCGG CTGCATGGCT GGAGGCTCAG
1621  GAGGAGGAGG  AGGTGGGCTT CGATTACAAG GACGATGACG ACAAGCTGtg ataa
``` wherein the sequence encoding GMCSF signal peptide is underlined, the valine codon immediately downstream of the sequence encoding the signal sequence is shown highlighted, the sequence encoding the immunogenic polypeptide is shown in standard letters, the sequence encoding the Flag tag is shown in italics and the tga and taa stop codons are shown in lower case.

8. Cloning Strategy

The codon-optimized T cell immunogen was cloned into the mammalian expression plasmid BV5, which consists of a modified CMV basic plasmid backbone optimized for growth in bacteria that harbors the human cytomegalovirus (CMV) promoter, the bovine growth hormone (BGH) polyadenylation site and the kanamycin resistance gene—lacking the Xho site. The cloning steps were as follows:

1) In a first step, an amino acid change from Leu to Meth was introduced into the synthesized T cell immunogen—one including the FLAG epitope at RT 41 position (segment 9) to cover one of the major antiretroviral resistance mutations site. The T cell immunogen gene (starting vector) was cloned in a spectomycin resistance harboring plasmid. A PCR-generated segment covering the RT M41 change was inserted into the T cell immunogen as SpeI/HindIII. Competent cells DH108B were used for transformation and were grown on LB-spectomycin media. The resulting plasmid was named HIVACAT RT M41. Insertion of the point mutation was confirmed by PCR sequencing using sense and antisense primers covering the segment 9 sequence.

2) In a second step, the HIVACAT RT M41 gene was inserted to the BV5 plasmid that lacks the Xho site in kanamycin resistance gene as SalI/EcoRI, by ligation of the vector and the gel purified digested HIVACAT RT M41 fragment. Competent cells DH108B were used for transformation and were grown in LB-Kan media. Resulting plasmid name was 297H (GMCSF-HIVACAT-FLAG). Insertion of the gene was confirmed by restriction digestion and PCR sequencing using sense (from the CMV promoter) and antisense primers (from the polyA BGH region).

3) In a third step, the epitope for the FLAG tag was removed from the 297H plasmid by BstEII-EcoRI digestion and insertion the annealed primers 298H Plus and 298H Minus:

```
298HPlus
                                   (SEQ ID NO: 51)
GTCACCGGGCGGCTGCATGGCTGGAGGCTCAGGAGGAGGAGGAGG
TGGGCTTCtgataaG 298H Minus:
                                   (SEQ ID NO: 52)
aattCttatcaGAAGCCCACCTCCTCCTCCTCCTGAGCCTCCAGC
CATGCAGCCGCCCG
```

The resulting plasmid was named 298H GMCSF-HIVACAT, accession number DSM 25555). See FIG. 1. Removal of the FLAG tag was confirmed by PCR sequencing using antisense primers (from the polyA BGH region).

Example 1

In-Vitro Expression Studies

Several transient transfections were performed to assess expression, localization and stability of the HIVACAT T cell immunogen.

Briefly, $1 \times 10^6$ human 293 cells in complete DMEM plus 10% fetal bovine serum (FBS) were plated on to 60 mm tissue culture dishes and allowed to adhere overnight. HEK 293 cells were transfected by CaPhosphate DNA co-precipitation with a total of 7 µg of DNA (100 ng or 250 ng of the 297H GMCSF-HIVACAT-FLAG plasmid DNA, 50 ng of GFP expressing plasmid pFRED143 topped up to 7 µg with Bluescript DNA).

6 hours after transfection the medium were replaced with 3 ml of DMEM supplemented with 2% of FCS. After 24 and 48 hrs the cells and the supernatants were collected in 0.5×RIPA.

Protein expression was analyzed by Western immunoblots. ¹/₂₅₀ of the total of the cell extracts and supernatants were loaded. The proteins were resolved by electrophoresis on 10% sodium dodecyl sulfate polyacrylamide gels (NuPage Bis-Tris, NuPAGE, Invitrogen, Life Technologies Corp., Carlsbad, Calif., US) and transferred onto nitrocellulose membranes.

297H plasmid was detected upon probing the membranes with horseradish peroxidase-conjugated anti-FLAG monoclonal antibody (Sigma-Aldrich Corp., Saint Louis, Mo., US) at a 1:3.000 dilution.

Bands were visualized using ECL. Membranes were imaged on a ChemiDoc XRS+.

Positive controls were used and included plasmid DNA encoding for clade B p55 Gag, which also harbored the FLAG tag.

Cell extracts from transient transfections using the 298H plasmid (encoding for the HIVACAT T cell immunogen without the FLAG-tag) were probed with human serum from an HIV-1 infected subject at a 1:3.000 dilution followed by a horseradish peroxidase-conjugated human anti-IgG, dilution 1:10.000.

297H and 298H plasmids stably (same estimated amount at 24 h and 48 h) expressed the HIVACAT T cell immunogen construct, which was visualized at the cell extract compartment. There was no evidence of secretion of the construct.

Example 2

Cellular Response in Mice

A stock of 1 ml (2 mg/ml) of 298H GMCSF-HIVACAT DNA was produced endofree for in vivo studies in mice.

Immunogenicity of the HIVACAT T cell immunogen was evaluated in 6-8 weeks old female C57BL/6 mice (Charles River Labs, Inc., Frederick, Md., US).

20 µg and 5 µg of DNA was delivered intramuscularly by electroporation using the Inovio system (Inovio Pharmaceuticals, Inc., Blue Bell, Pa., US) in the left and right quadriceps (20 µg/50 µl per dose, 25 µl per site) at week 0 and 4. Mice were sacrificed 2 weeks after the last immunization. Mice splenocytes and serum were harvested for immunogenicity studies. Control DNAs used were:

1) 114H p55 gag clade B: expresses full gag protein;
2) 132H NTV: expresses a chimaeric protein of nef, tat and vif;
3) 133H pol: expresses full pol protein; and
4) BV4 CMV-kan-Basic: SHAM control, similar DNA plasmid backbone without any expressed transgene.

35 mice were used in the experiment, pooling 5 mice per group. Distribution of the immunization per group was as follows:

| Groups | Inocula number | Delivery | Dose | DNA/Site (quadriceps) | n |
|---|---|---|---|---|---|
| 1 | 114 p55 gag clade B | I.M. Inovio | 20 µg | 25 mL/site | 5 |
| 2 | 114 p55 gag clade B + 132H NTV + 133 pol | I.M. Inovio | 20 µg each | 25 mL/site | 5 |
| 3 | 298H GMCSF-HIVACAT | I.M. Inovio | 20 µg | 25 mL/site | 5 |
| 4 | 114 p55 gag clade B | I.M. Inovio | 5 µg | 25 mL/site | 5 |
| 5 | 114 p55 gag clade B + 132H NTV + 133 pol | I.M. Inovio | 5 µg each | 25 mL/site | 5 |
| 6 | 298H GMCSF-HIVACAT | I.M. Inovio | 5 µg | 25 mL/site | 5 |
| 7 (SHAM) | BV4 CMVKan-Basic | I.M. Inovio | 20 µg | 25 mL/site | 5 |

Cellular immune responses were characterized on a first step using intracellular cytokine staining (ICS) in pooled splenocytes (cells from the 5 mice belonging to group) and using a pool of overlapping peptides covering all gag, pol, nef, tat and vif proteins.

Briefly, pooled isolated mouse splenocytes from each group of mice were incubated at a density if $2\times10^6$ cells/ml, in 1 ml co-culture overnight, in the presence of peptide pools (15-mers, overlapping by 11aa covering clade B gag, consensus B pol and NL43 nef, tat and vif sequences, 1 µg/ml each peptide, total of about 12 hours, 1 hour without Golgi stop to prevent cytokine secretion). Surface immunostaining was performed with CD3-allophycocyanin-Cy7, CD4-PerCP, CD8-Pacific Blue (BD Biosciences, Inc., Franklin Lakes, N.J., US). Intracellular cytokine staining was performed using interferon gamma-FITC antibody (BD Biosciences, Inc., Franklin Lakes, N.J., US) after permeabilization.

Figure 2A:
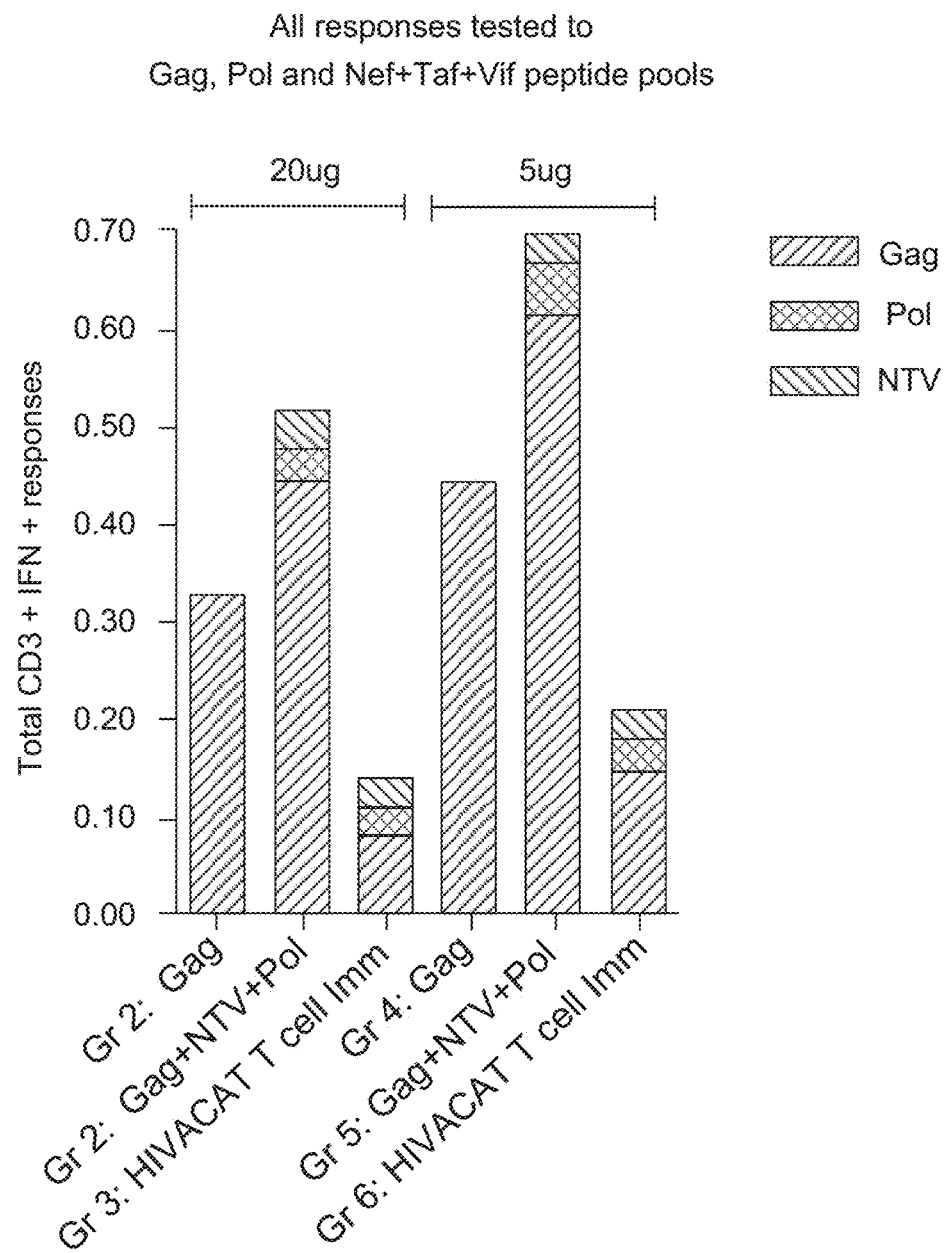
FIG. 2. Cellular immune responses analyzed in pooled splenocytes by flow cytometric analysis. Frequency of total Gag, Pol, and Nef-Tat-Vif specific interferon gamma responses among groups in FIG. 2A and distribution of CD4 and CD8 responses in FIG. 2B are shown.
Figure 2B:
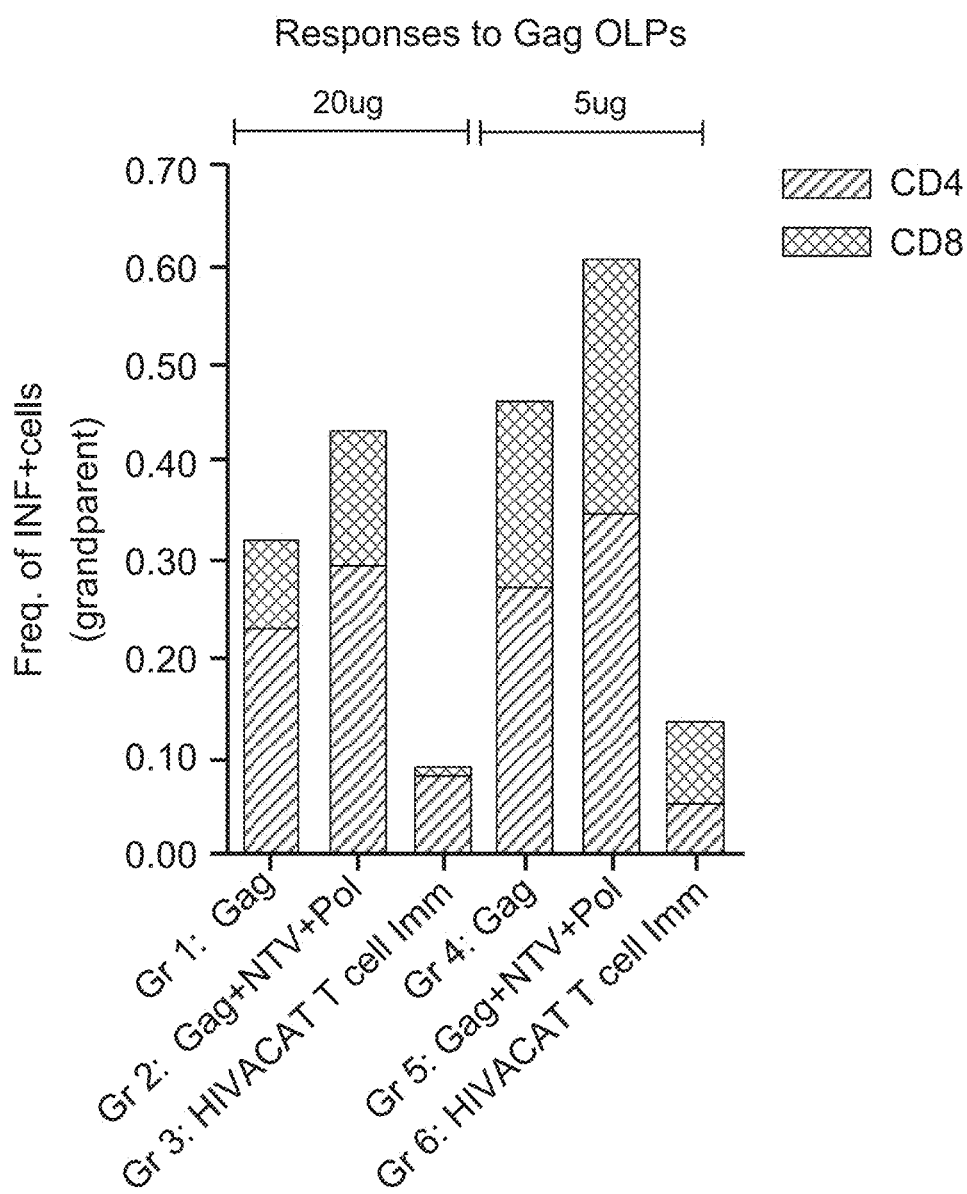

From the first immunogenicity analyses, both 20 µg and 5 µg of DNA in C57BL/6 mice did generate detectable interferon gamma −+ responses to full gag, pol and nef-tat-vif peptide pools. See FIG. 2a. Distribution of CD4+ and CD8+ responses is shown. See FIG. 2b.

At an individual mice level, responses were deconvoluted using frozen splenocytes stimulated with 8 pools of peptides to cover the protein subunits included in the immunogen in an interferon gamma ELISpot assay.

ELISpot assay was performed by using mouse interferon gamma ELISpot kit (ALP) (Mabtech AB, Stockholm, SE) following the manufacturer's instructions with minor modifications. For all assays, mice splenocytes were added at an input cell number of $4\times10^5$ cells/well in 140 µl of Rosewell Park Memorial Institute medium 1640 with 10% fetal bovine serum in 96-well polyvinylidene plates (Millipore Corp., Bedford, Mass., US) alone or with HIV-1-specific peptide pools (14 µg/ml final concentration for each peptide) for 16 hours at 37° C. in 5% $CO_2$. Eight pools of peptides, each containing between 2 and 12 peptides of 18 amino acids based on the 2001 consensus-B sequence were pooled into the different protein subunits (gag-p17, gag-p24, gag-p2p7p1p6, pol-RT, pol-protease, pol-integrase, vif and nef) spanning the segments included in the HIVACAT T cell immunogen. See http://hiv-web.lanl.gov/content/hiv-db/CONSENSUS/M_GROUP/Consensus.html, January 2012. The HIV peptides pools used in mice immunized with DNAs expressing full gag, pol, nef, tat and vif proteins, consisted of 18-mers peptides with an overlap of 11 residues spanning the complete gag (6 pools, 11 peptides/each), pol (8 pools, 16 or 17 peptides/each), nef (2 pools, 13 o 14 peptides/each), tat (1 pool, 12 peptides) and vif (2 pools, 12 peptides/each) proteins.

Concavalin A (Sigma-Aldrich Corp., Saint Louis, Mo., US), at 5 mg/ml, was used as a positive control. The plates were developed with one-step 5-bromo-4-chloro-3-indolyl phosphate/Nitroblue Tetrazolium (BCIP/NBT, Bio-Rad Laboratories, Inc., Irvine, Calif., US). The spots on the plates were counted using an automated ELISPOT reader system (CTL Analyzers LLC, Cleveland, Ohio, US) using ImmunoSpot software and the magnitude of responses was expressed as spot forming cells (SFC) per million input splenocytes. The threshold for positive responses was defined as at least 5 spots per well and responses exceeding the "mean number of spots in negative control wells plus 3 standard deviations of the negative control wells" and "three times the mean of negative control wells", whichever was higher.

Figure 3:
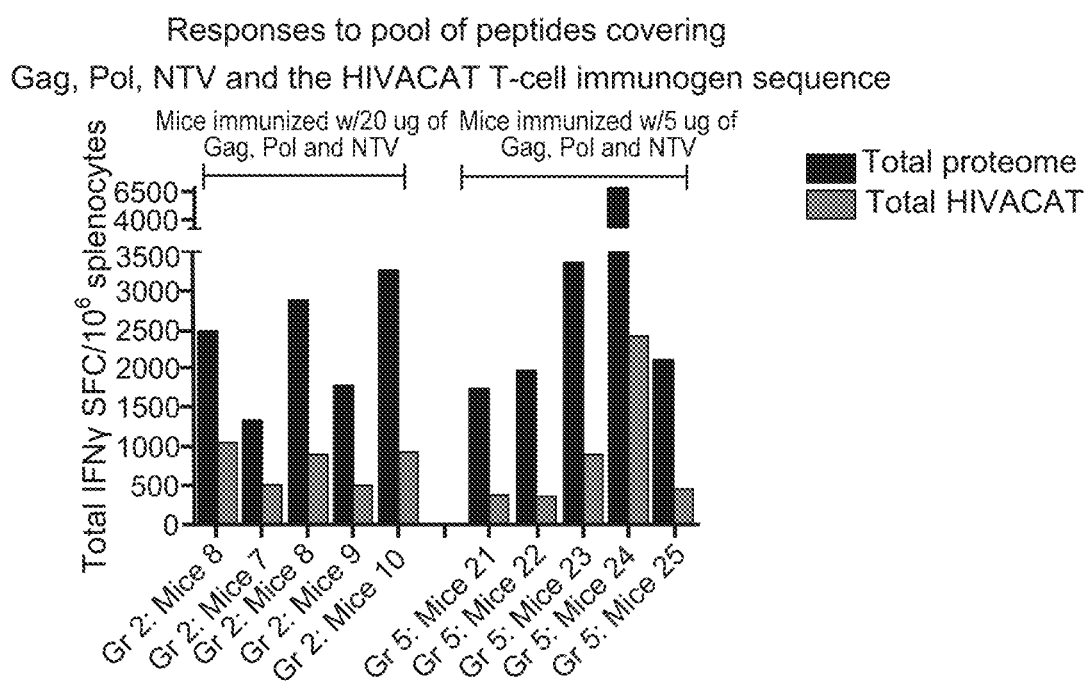
FIG. 3. Responses to Gag, Pol, NTV and the HIVACAT T cell immunogen sequence measured by interferon gamma ELISpot assay in murine splenocytes. The individual mice were immunized with the plasmids encoding for the full Gag, Pol and Nef-Tat-Vif polypeptide. Contribution of the responses targeting the regions included in the HIVACAT T cell immunogen to the total interferon gamma Gag-Pol-NTV specific response is shown.

1) Dominance of interferon gamma responses developed in mice immunized with plasmids encoding for the entire gag, pol, nef, tat and vif proteins was towards regions outside the HIVACAT T cell immunogen covered segments (median ratio of responses targeting HIVACAT immunogen regions/total gag+pol+nef+tat+vif was 0.26 (range 0.17-0.42)) and did not differ among groups immunized with high dose (20 µg) or low dose (5 µg) of DNA. See FIG. 3

Figure 4A:
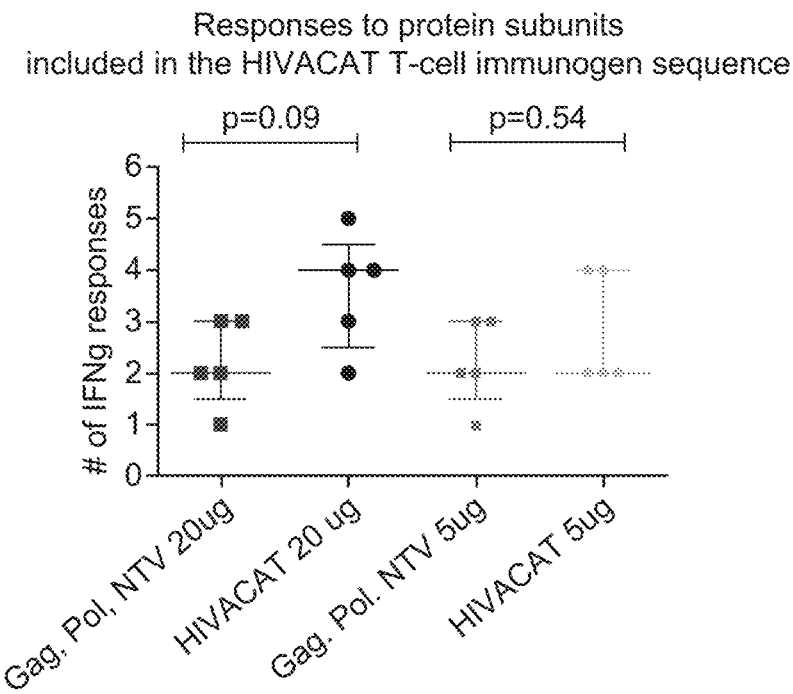
FIG. 4. Comparison of the breadth in FIG. 4A and magnitude in FIG. 4B of the interferon gamma responses targeting the HIVACAT T cell immunogen in immunized mice. The subjects were treated with either the plasmids encoding the full proteins or the minimal T cell sequence.
Figure 4B:
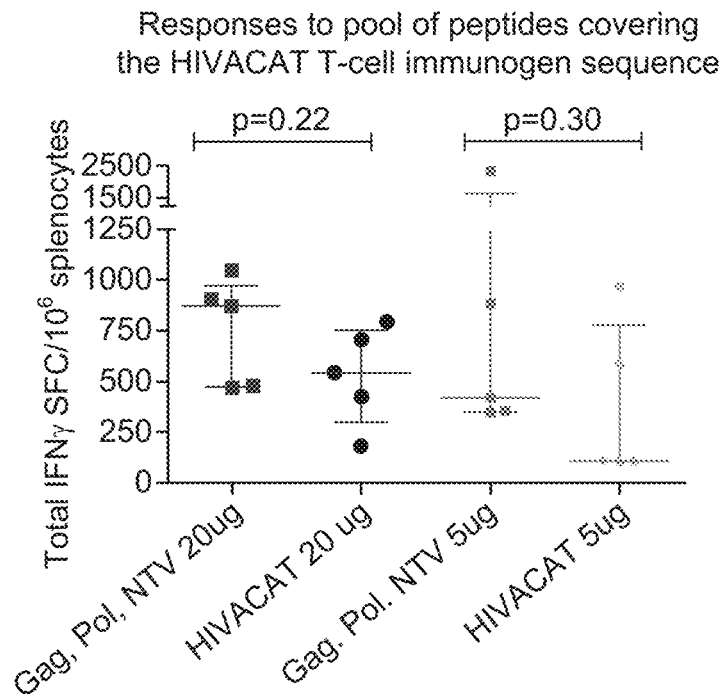

2) Median breadth of responses to protein subunits included in the HIVACAT T cell immunogen sequence was 4 (range 2-5) in mice immunized with 20 µg of HIVACAT vs 2 responses (range 1-3) in mice immunized with 20 µg of plasmids encoding for entire proteins (ns) with no significant differences in the magnitude of responses. Six out of the eight protein subunits were at least targeted once in the mice immunized with the HIVACAT T cell immunogen. See FIG. 4.

| HIVACAT T cell immunogen segments | HIV-1 protein | Pool number | Peptides/pool | Mice making a response (groups Gag-Pol-NTV) | Mice making a response (groups HIVACAT) |
|---|---|---|---|---|---|
| Seg-1 | gag-p17 | HTI-pool1 | 10 | 0/10 | 3/10 |
| Seg-2 | gag-p24 | HTI-pool2 | 12 | 10/10 | 10/10 |
| Seg-3 | gag-p24 | | | | |
| Seg-4 | gag-p24 | | | | |
| Seg-5 | gag-p24 | | | | |
| Seg-6 | gag-p24 | | | | |
| Seg-7 | gag-p2p7p1p6 | HTI-pool3 | 3 | 0/10 | 0/10 |
| Seg-8 | pol-protease | HTI-pool4 | 6 | 4/10 | 7/10 |
| Seg-9 | pol-RT | HTI-pool5 | 11 | 5/10 | 9/10 |
| Seg-10 | pol-RT | | | | |
| Seg-11 | pol-RT | | | | |
| Seg-12 | pol-integrase | HTI-pool6 | 4 | 0/10 | 0/10 |
| Seg-13 | pol-integrase | | | | |
| Seg-14 | vif | HTI-pool7 | 4 | 3/10 | 2/10 |

| HIVACAT T cell immunogen segments | HIV-1 protein | Pool number | Peptides/pool | Mice making a response (groups Gag-Pol-NTV) | Mice making a response (groups HIVACAT) |
|---|---|---|---|---|---|
| Seg-15 | vif | | | | |
| Seg-16 | nef | HTI-pool8 | 2 | 0/10 | 1/10 |

Figure 5A:
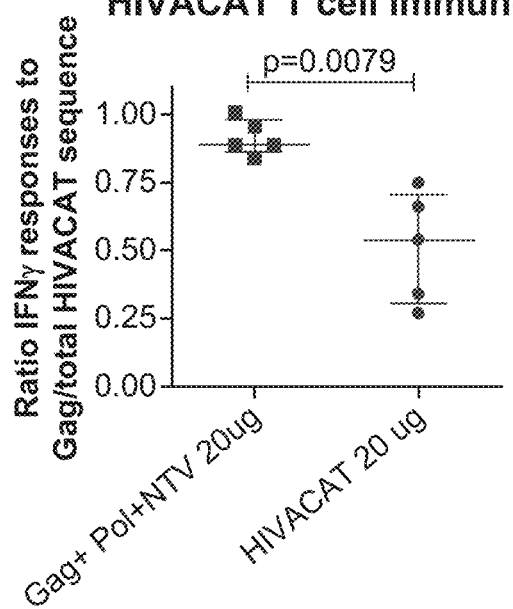
FIG. 5. Balance of interferon gamma responses against Gag, Pol, Vif or Nef for mice immunized with 20 µg of plasmids encoding full Gag, Pol plus Nef-Tat-Vif polypeptide and HIVACAT T cell immunogen. Dominance of Gag-specific responses is shown in FIG. 5A for mice immunized with full proteins whereas a more balanced repertoire is seen in FIG. 5B for mice immunized with the HIVACAT T cell immunogen.
Figure 5B:
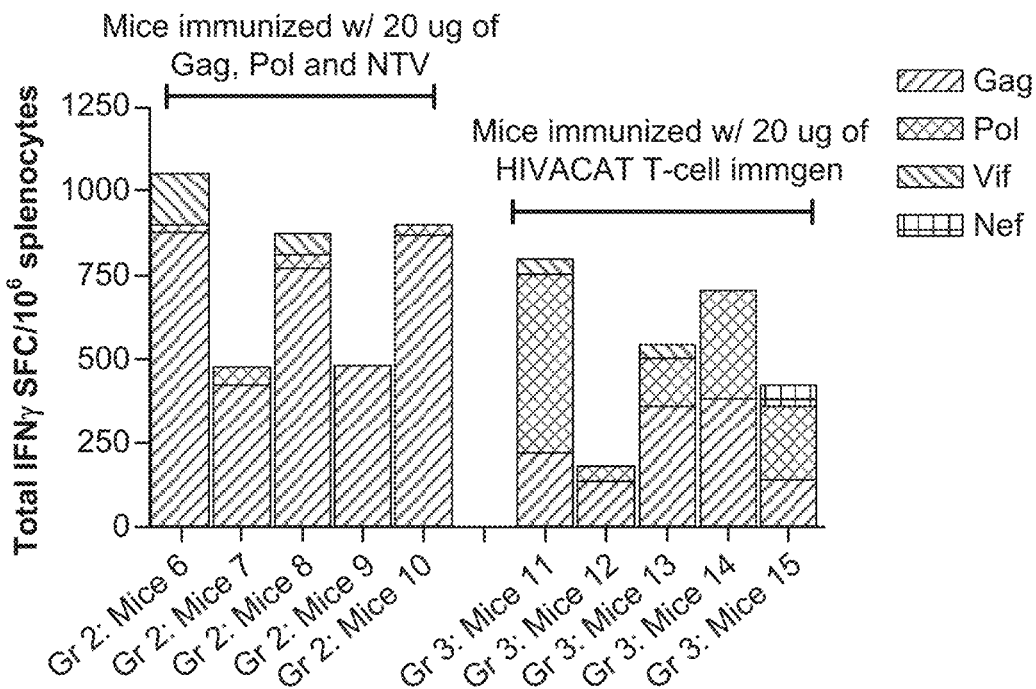

4) Dominance of responses in mice immunized with plasmids encoding the full proteins of gag, pol, nef, tat and vif was 89% driven mainly towards gag, while in mice immunized with the HIVACAT T cell immunogen at high doses was more balanced to all protein components (gag, pol, vif and nef) contained in the immunogen. See FIG. 5.

Example 3

Humoral Response in Mice

Figure 6A:
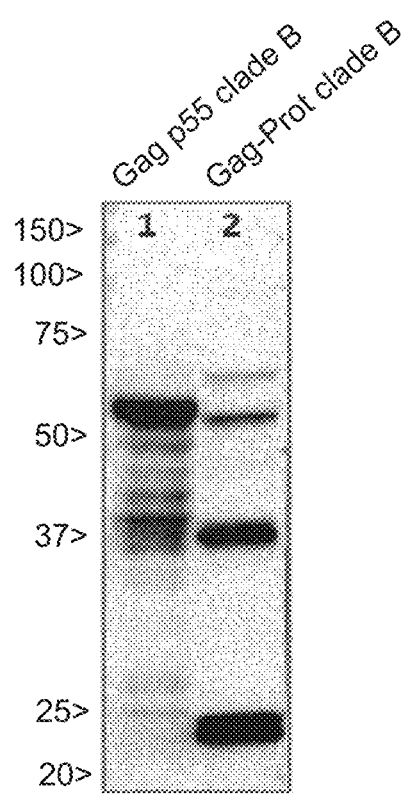
FIG. 6. Binding antibodies to p24, p37 and p55 detected by Western immunoblot by using cell extracts from HEK 293 cells transfected with the 1 mg of gag and gag-pol expression vectors (showing p55 gag, and processed p24, p37 and p55 gag subunits) separated on 12% SDS-Page and probing the membranes with a) human sera of and HIV-infected patient (FIG. 6A), b) pooled sera from mice immunized with high doses of the immunogen (FIG. 6B) and c) pooled sera from mice immunized with low doses of the immunogen (all at a 1:100 dilution) (FIG. 6C).
Figure 6B:
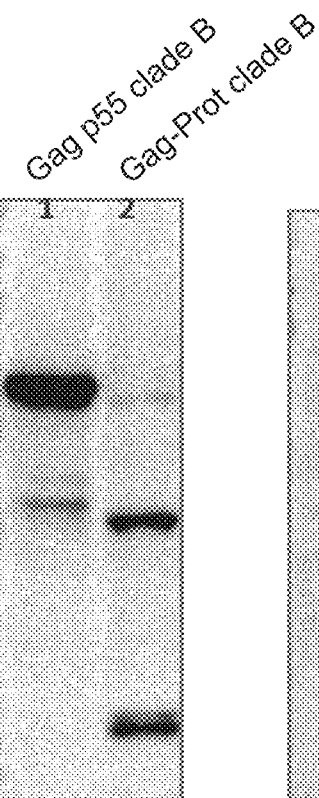
Figure 6C:
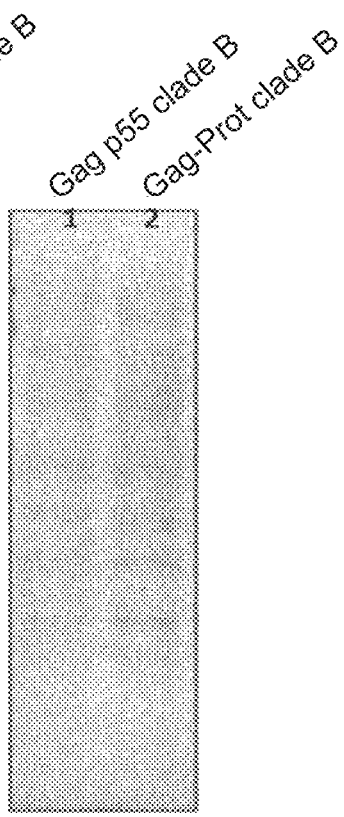
Figure 7A:
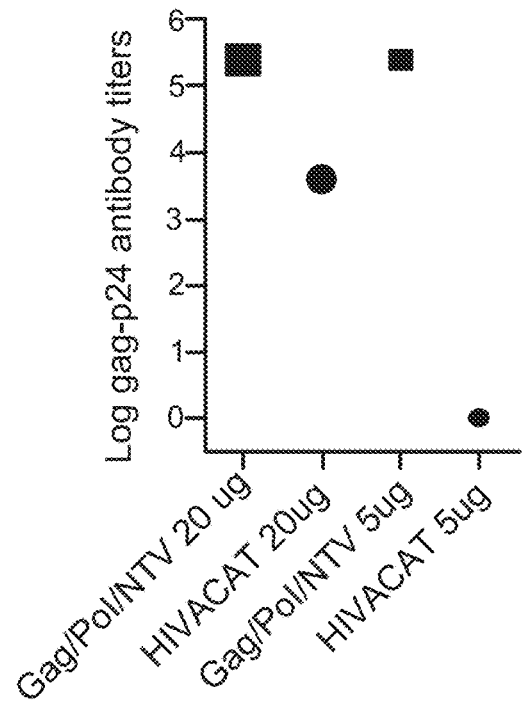
FIG. 7. a) Endpoint titers of Gag-p24 specific binding antibody from treated mice (FIG. 7A). The determination was performed by ELISA from individual serial 4-fold diluted pooled serum samples. b) In house developed gag p55 ELISA using the HIV-1IIIB pr55 Gag recombinant protein (Cat. No. 3276, NIH Reagent Program, Bethesda, Md., US) (FIG. 7B). The determination was performed in individual mice sera at 1:100 dilution.
Figure 7B:
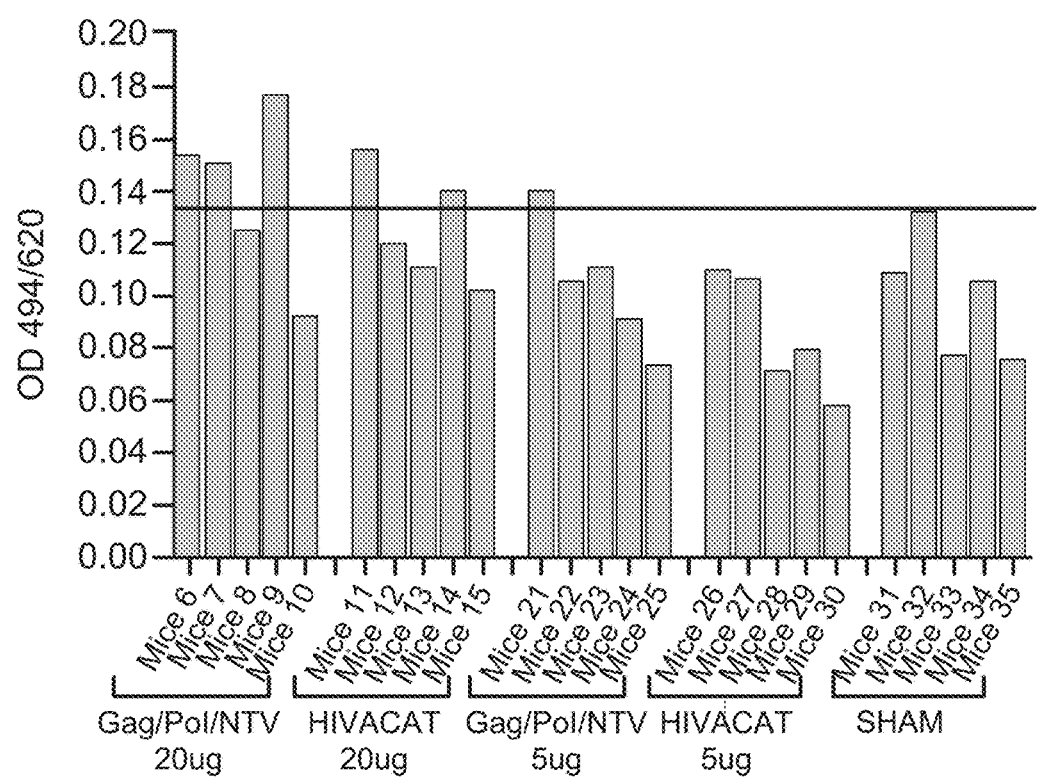

Humoral responses were first analyzed in pooled mice sera. Binding antibodies to p24, p37 and p55 were detected by western immunoblot by using cell extracts from HEK 293 cells transfected with the 1 mg of gag expression vectors separated on 12% SDS-Page and probing the membranes with pooled sera from mice (at a 1:100 dilution). Antibody titers to gag p24 were measured by ELISA. Serial 4-fold dilutions of the pooled serum samples were assessed and the optical absorbance at 450 nm was determined (Advanced BioScience Lab, Inc., Kensington, Md., US). The binding titers were reported as the highest dilution scoring positive having a value higher than the average plus 3 standard deviations obtained with control sera from the mice immunized with SHAM DNA.

a) From the first humoral immunogenicity analyses, the HIVACAT T cell immunogen induced binding antibody responses to gag p55, p37 and p24 detectable by Western blot in the group of mice immunized with 20 µg. See FIG. 6.

b) Binding antibodies to p24 were quantified by ELISA. The endpoint titers of gag-p24 specific binding antibody from the mice that received the plasmids described were determined by ELISA from individual serial 4-fold diluted pooled serum samples. In the high dose group of mice immunized with HIVACAT T cell immunogen at a titre of 1:4,000 which were lower to the titers detected in mice immunized with the full gag construct. No binding antibodies to p24 were measurable in the low dose group. See FIG. 7a. At an individual mice level, in house developed gag p55 ELISA using the HIV-1IIIB pr55 gag recombinant protein (Cat. No. 3276, NIH Reagent Program, Bethesda, Md., US) was performed with mice sera at 1:100 dilution. Low levels of antibody were detectable in 2 out of 3 mice immunized with the high dose of the immunogen. See FIG. 7b.

Example 4

Heterologous Prime/Boost In-Vivo Immunogenicity in Mice

Material and Methods

Preparation of pDNA-HIVACAT and MVA-HIVACAT Vaccines

The codon-optimized T cell immunogen was cloned into the mammalian expression plasmid BV5, which consists of a modified CMV basic plasmid backbone optimized for growth in bacteria that harbors the human cytomegalovirus (CMV) promoter, the bovine growth hormone (BGH) polyadenylation site and the kanamycin resistance gene—lacking the Xho site. The plasmid DNA for mice immunizations was prepared using the Endo-Free Megaprep (Qiagen) and stored −80° C. until use.

A recombinant MVA expressing the HIVACAT gene was made as described previously {Letourneau, 2007 #235; Nkolola, 2004 #321}. Briefly, chicken embryo fibroblast (CEF) cells grown in Dulbeco's Modified Eagle's Medium supplemented with 10% FBS, penicillin/streptomycin and glutamine (DMEM 10) were infected with parental MVA at MOI 1 and transfected using Superfectin (Quiagen) with 3 ug of pDNA-HIVACAT carrying the .beta.-galactosidase gene as a marker. Two days later, the total virus was harvested and used to re-infect CEF cells. MVA was subjected to five round of plaque purification, after which a master virus stock was grown, purified on a 36% sucrose cushion, tittered and stored at −80° C. until use.

In-Vivo Immunogenicity in C57BL/6 Mice

For heterologous prime/boost in-vivo immunogenicity experiments in mice, groups of five 6- to 8-weeks-old female C57BL/6 (Harlan Laboratories Ltd., Barcelona, Spain) were used. Mice were primed intramuscularly with 100 µg of pDNA-HIVACAT (2 or 3 vaccinations) followed by a 10^6 pfu of MVA-HIVACAT boost (groups: 2×DNA, 3×DNA, 2×DNA+1MVA and 3×DNA+1MVA respectively) All vaccinations were separated by three weeks.

All mice were sacrificed two weeks after the last vaccination in each experiment. Mice splenocytes and serum were harvested for immunogenicity studies. Spleens were removed and pressed individually through a cell strainer (Falcon) using a 5-ml syringe rubber punger. Following rbc lysis, splenocytes were washed and resuspended in RPMI 1640 supplemented with 10% FCS, penicillin/streptomycin (R10) and frozen until use.

All animal procedures and care were approved by a local Ethical Committee.

Overlapping Peptides and Distribution of Peptide Pools

To evaluate immunogenicity of the heterologous regimens were pDNA or MVA expressing only the HIVACAT T-cell immunogen and to rule out immunogenicity of the potential junctional epitopes an overlapping peptide set of 147 peptides of 15 amino acids in length (overlapping by 11 residues) spanning the entire HIVACAT T-cell immunogen (including the leader sequence and linkers regions) was newly synthesized using 9-Fluorenylmethyloxycarbonyl (Fmoc)-chemistry. Peptides were distributed in 18 different pools, according to protein subunits and segments of the immunogen (1 pool for the signal peptide sequence, n=4 peptides; 7 pools for Gag, n=8-11 peptides/each; 7 pools for Pol, n=5-11 peptides/each; 2 pools for Vif, n=6-8 peptides/ each and 1 pool for Nef, n=2 peptides) Results are presented grouped by IFNγ responses specific for the eight protein subunits (Gag p17, Gag p24, Gag p2p7p1p6, Pol-Protease, Pol-RT, Pol-Integrase, Vif and Nef)

Murine INFγ ELISPOT Assay

ELISpot assay was performed by using mouse IFNγ ELISpot kit (ALP) (Mabtech AB, Stockholm, SE) following the manufacturer's instructions with minor modifications. For all assays, frozen mice splenocytes were first thawed and rested for 5 h 37° C. in R10 before use. Cells were added at an input cell number of $4 \times 10^5$ cells/well in 140 µl of R10 in 96-well polyvinylidene plates (Millipore Corp., Bedford, Mass., US) alone or with HIV-1-specific peptide pools (14 µm/ml final concentration for each peptide) for 16 hours at 37° C. in 5% $CO_2$. Concavalin A (Sigma-Aldrich Corp., Saint Louis, Mo., US), at 5 mg/ml, was used as a positive control. The plates were developed with one-step 5-bromo-4-chloro-3-indolyl phosphate/Nitroblue Tetrazolium (BCIP/NBT, Bio-Rad Laboratories, Inc., Irvine, Calif., US). The spots on the plates were counted using an automated ELISPOT reader system (CTL Analyzers LLC, Cleveland, Ohio, US) using ImmunoSpot software and the magnitude of responses was expressed as spot forming cells (SFC) per million input splenocytes. The threshold for positive responses was defined as at least 5 spots per well and responses exceeding the "mean number of spots in negative control wells plus 3 standard deviations of the negative control wells" and "three times the mean of negative control wells", whichever was higher.

Results

Figure 8B:
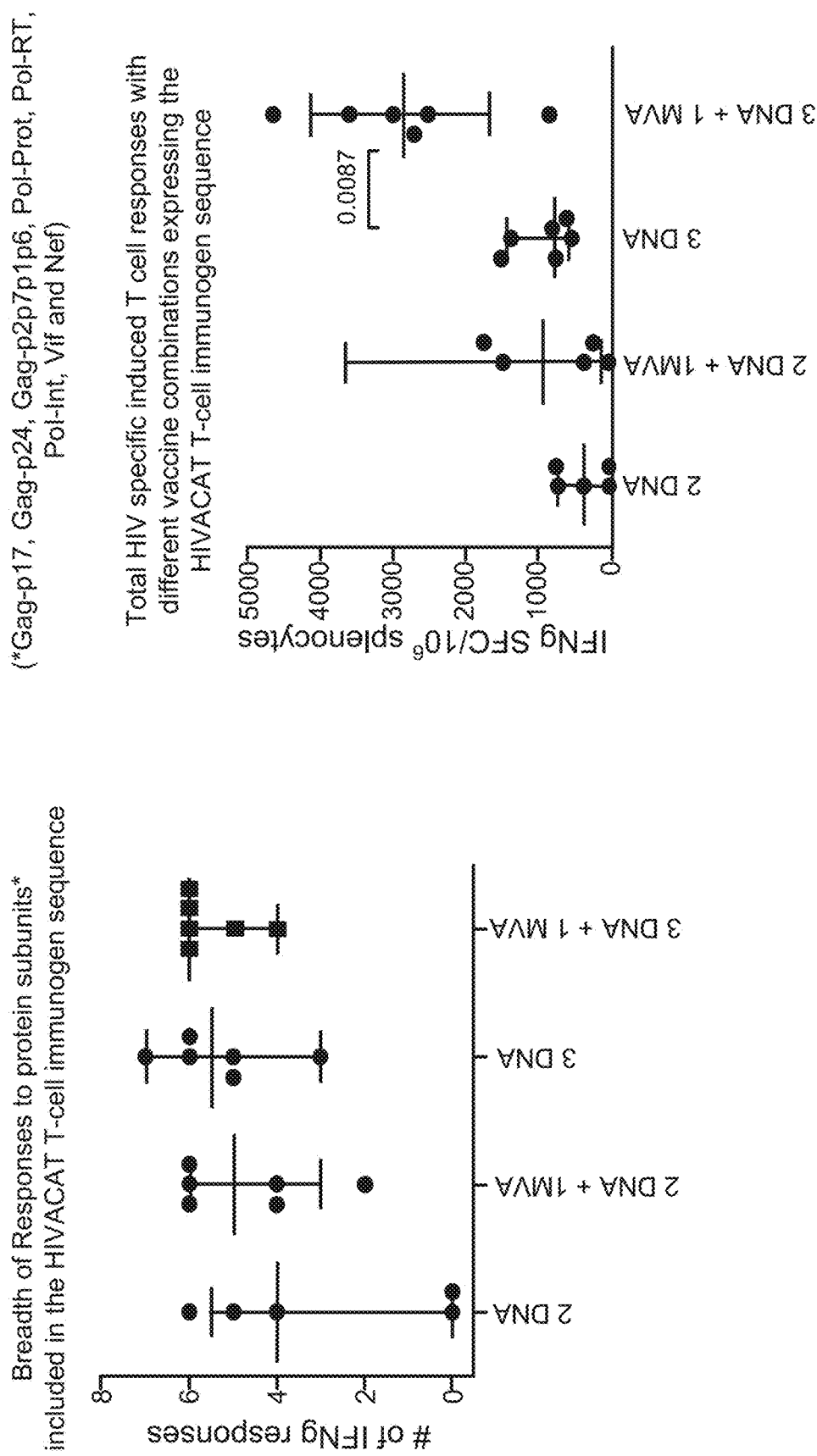
FIG. 8. a) Schematic representation of mice immunizations (FIG. 8A). Groups of six C57BL/6 mice were used to compare immunogenicity of the different heterologous combinations (2×DNA prime vs 3×DNA prime followed by 1×MVA boost) using either 100 µg of pDNA-HIVACAT or 10^6 pfu of MVA-HIVACAT by intramuscular injection. b) Comparison of the breadth and magnitude of the IFNγ responses targeting HIVACAT T cell immunogen in individual immunized mice (FIG. 8B). c) Distribution of Gag, Pol, Vif and Nef specific responses in individual immunized mice (FIG. 8C). d) Distribution among the 8 protein subunits included in the HIVACAT T cell immunogen (Gag p17, Gag p24, Gag p2p7p1p6, Pol-Protease, Pol-RT, Pol-Integrase, Vif and Nef) in different immunization groups is shown (FIG. 8D).
Figure 8D:
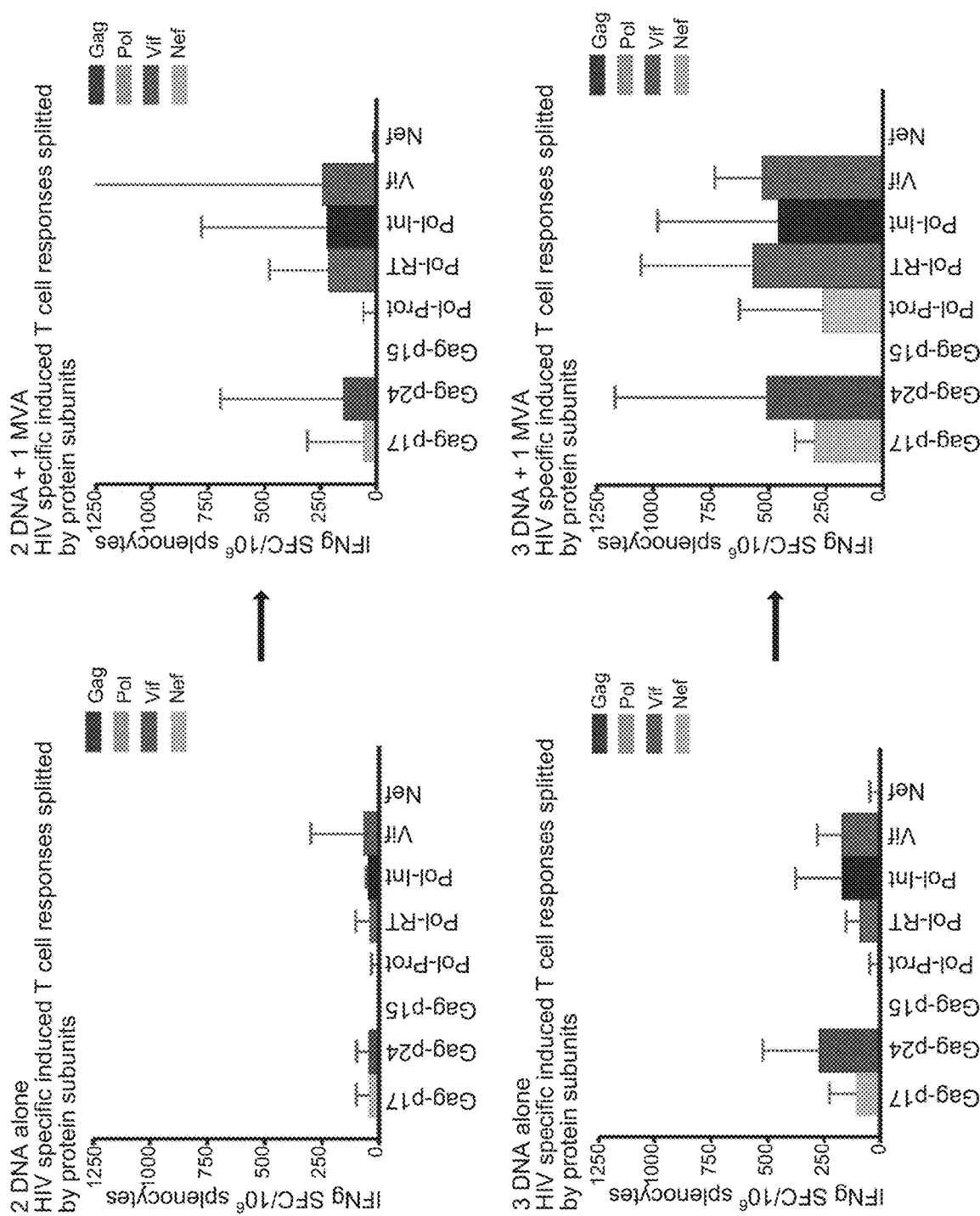

In these experiments as no mice were immunized using plasmids encoding for full proteins, a second set of overlapping peptides matching the exact immunogen sequence was synthesized and used for immunogenicity comparisons. Three intramuscular (i.m.) immunisations with 100 µg of pDNA-HIVACAT were able to induce frequencies of IFNγ responses in all mice that were comparable to the frequencies of IFNγ responsed induced by immunisations with the electroporation Inovio system. However, two pDNA i.m. vaccinations were found to be immunogenic in only three animals (60%) compared to 100% of animals inducing a responses after three pDNA i.m. immunizations. Interestingly, MVA-HIVACAT vaccine was able to boost responses both in breadth and magnitude, (FIG. 8B) in the two groups analyzed, but did just significantly increase the magnitude of responses when mice had previously been primed with three doses of pDNA-HIVACAT (FIGS. 8B and 8C). As seen in the previous EP experiments, a balanced and broad response to most of all the protein-subunits included in the immunogen was observed in all animals, without a clear pattern of dominance among them. No nef or gag-p15 specific responses were detected in the studied mice (FIG. 8D).

While the invention is described in some detail for purposes of clarity and understanding, it will be appreciated by one skilled in the art from a reading of this disclosure that various changes in form and detail can be made without departing from the true scope of the invention and appended claims.

All publications mentioned hereinabove are hereby incorporated in their entirety by reference.

The invention claimed is:

1. An expression cassette comprising a nucleic acid molecule, a promoter sequence, and a 3'-UTR, wherein the nucleic acid molecule encodes an immunogenic polypeptide, wherein the immunogenic polypeptide comprises:
   i) a sequence having at least 90% identity to the sequence of SEQ ID NO:1,
   ii) a sequence having at least 90% identity to the sequence of SEQ ID NO:2,
   iii) a sequence having at least 90% identity to the sequence of SEQ ID NO:3,
   iv) a sequence having at least 90% identity to the sequence of SEQ ID NO:4,
   v) a sequence having at least 90% identity to the sequence of SEQ ID NO:5,
   vi) a sequence having at least 90% identity to the sequence of SEQ ID NO:6,
   vii) a sequence having at least 90% identity to the sequence of SEQ ID NO:7,
   viii) a sequence having at least 90% identity to the sequence of SEQ ID NO:8,
   ix) a sequence having at least 90% identity to the sequence of SEQ ID NO:9,
   x) a sequence having at least 90% identity to the sequence of SEQ ID NO:10,
   xi) a sequence having at least 90% identity to the sequence of SEQ ID NO:11,
   xii) a sequence having at least 90% identity to the sequence of SEQ ID NO:12,
   xiii) a sequence having at least 90% identity to the sequence of SEQ ID NO:13,
   xiv) a sequence having at least 90% identity to the sequence of SEQ ID NO:14,
   xv) a sequence having at least 90% identity to the sequence of SEQ ID NO:15, and
   xvi) a sequence having at least 90% identity to the sequence of SEQ ID NO:16;
   wherein at least two of i)-xvi) are joined by an amino acid linker, and wherein the sequence of each of i)-xvi) is 11-85 amino acids in length.

2. The expression cassette of claim 1, wherein the immunogenic polypeptide comprises:
   i) a sequence having at least 95% identity to the sequence of SEQ ID NO:1,
   ii) a sequence having at least 95% identity to the sequence of SEQ ID NO:2,
   iii) a sequence having at least 95% identity to the sequence of SEQ ID NO:3,
   iv) a sequence having at least 95% identity to the sequence of SEQ ID NO:4,
   v) a sequence having at least 95% identity to the sequence of SEQ ID NO:5,
   vi) a sequence having at least 95% identity to the sequence of SEQ NO:6,
   vii) a sequence having at least 95% identity to the sequence of SEQ ID NO:7,
   viii) a sequence having at least 95% identity to the sequence of SEQ ID NO:8,
   ix) a sequence having at least 95% identity to the sequence of SEQ ID NO:9,
   x) a sequence having at least 95% identity to the sequence of SEQ ID NO:10,
   xi) a sequence having at least 95% identity to the sequence of SEQ ID NO:11,
   xii) a sequence having at least 95% identity to the sequence of SEQ ID NO:12, xiii) a sequence having at least 95% identity to the sequence of SEQ ID NO:13,
xiv) a sequence having at least 95% identity to the sequence of SEQ ID NO:14,
xv) a sequence having at least 95% identity to the sequence of SEQ ID NO:15, and
xvi) a sequence having at least 95% identity to the sequence of SEQ ID NO:16.

3. The expression cassette of claim 1, wherein the immunogenic polypeptide comprises the sequences of SEQ ID NOs:1-16.

4. The expression cassette of claim 1, wherein the amino acid linker is a single, dual, or triple alanine amino acid linker, and wherein the amino acid linker results in the formation of an AAA sequence in the junction region between adjoining sequences.

5. The expression cassette of claim 1, wherein the sequences of i)-xvi) are adjoined by amino acid linkers.

6. The expression cassette of claim 5, wherein the amino acid linkers are single, dual, or triple alanine amino acid linkers, and wherein the amino acid linkers result in the formation of an AAA sequence in the junction region between adjoining sequences.

7. The expression cassette of claim 6, wherein the immunogenic polypeptide has the sequence of SEQ ID NO: 99.

8. The expression cassette of claim 7, wherein the nucleic acid molecule has the sequence of SEQ ID NO: 100.

9. The expression cassette of claim 1, wherein the nucleic acid molecule is codon optimized for expression in human cells.

10. The expression cassette of claim 1, wherein the expression cassette further comprises a selection marker.

11. A cell comprising the expression cassette of claim 1.

12. An expression vector comprising the expression cassette of claim 1.

13. A cell comprising the expression vector of claim 12.

14. An expression vector comprising a nucleic acid molecule encoding an immunogenic polypeptide, wherein the immunogenic polypeptide comprises:
i) a sequence having at least 90% identity to the sequence of SEQ ID NO:1,
ii) a sequence having at least 90% identity to the sequence of SEQ ID NO:2,
iii) a sequence having at least 90% identity to the sequence of SEQ ID NO:3,
iv) a sequence having at least 90% identity to the sequence of SEQ ID NO:4,
v) a sequence having at least 90% identity to the sequence of SEQ ID NO:5,
vi) a sequence having at least 90% identity to the sequence of SEQ ID NO:6,
vii) a sequence having at least 90% identity to the sequence of SEQ :ID NO:7,
viii) a sequence having at least 90% identity to the sequence of SEQ ID NO:8,
ix) a sequence having at least 90% identity to the sequence of SEQ ID NO:9,
x) a sequence having at least 90% identity to the sequence of SEQ ID NO:10,
xi) a sequence having at least 90% identity to the sequence of SEQ NO:11,
xii) a sequence having at least 90% identity to the sequence of SEQ ID NO:12,
xiii) a sequence having at least 90% identity to the sequence of SEQ ID NO:13,
xiv) a sequence having at least 90% identity to the sequence of SEQ ID NO:14,
xv) a sequence having at least 90% identity to the sequence of SEQ ID NO:15, and
xvi) a sequence having at least 90% identity to the sequence of SEQ ID NO:16;
wherein at least two of i)-xvi) are joined by an amino acid linker, and wherein the sequence of each of i)-xvi) is 11-85 amino acids in length.

15. The expression vector of claim 14, wherein the immunogenic polypeptide comprises:
i) a sequence having at least 95% identity to the sequence of SEQ ID NO:1,
ii) a sequence having at least 95% identity to the sequence of SEQ ID NO:2,
iii) a sequence having at least 95% identity to the sequence of SEQ ID NO:3,
iv) a sequence having at least 95% identity to the sequence of SEQ ID NO:4,
v) a sequence having at least 95% identity to the sequence of SEQ ID NO:5,
vi) a sequence having at least 95% identity to the sequence of SEQ ID NO:6,
vii) a sequence having at least 95% identity to the sequence of SEQ ID NO:7,
viii) a sequence having at least 95% identity to the sequence of SEQ ID NO:8,
ix) a sequence having at least 95% identity to the sequence of SEQ ID NO:9,
x) a sequence having at least 95% identity to the sequence of SEQ ID NO:10,
xi) a sequence having at least 95% identity to the sequence of SEQ ID NO:11,
xii) a sequence having at least 95% identity to the sequence of SEQ ID NO:12,
xiii) a sequence having at least 95% identity to the sequence of SEQ ID NO:13,
xiv) a sequence having at least 95% identity to the sequence of SEQ ID NO:14,
xv) a sequence having at least 95% identity to the sequence of SEQ ID NO:15, and
xvi) a sequence having at least 95% identity to the sequence of SEQ ID NO:16.

16. The expression vector of claim 14, wherein the immunogenic polypeptide comprises the sequences of SEQ ID NOs:1-16.

17. The expression vector of claim 14, wherein the amino acid linker is a single, dual, or triple alanine amino acid linker, and wherein the amino acid linker results in the formation of an AAA sequence in the junction region between adjoining sequences.

18. The expression vector of claim 14, wherein the sequences of i)-xvi) are adjoined by amino acid linkers.

19. The expression vector of claim 18, wherein the amino acid linkers are single, dual, or triple alanine amino acid linkers, and wherein the amino acid linkers result in the formation of an AAA sequence in the junction region between adjoining sequences.

20. The expression vector of claim 19, wherein the immunogenic polypeptide has the sequence of SEQ ID NO: 99.

21. The expression vector of claim 20, wherein the nucleic acid molecule has the sequence of SEQ ID NO: 100.

22. The expression vector of claim 14, wherein the nucleic acid molecule is codon optimized for expression in human cells.

23. A cell comprising the expression vector of claim 14.

24. An expression vector comprising a nucleic acid molecule encoding an immunogenic polypeptide, wherein the immunogenic polypeptide comprises:
  i) the sequence of SEQ ID NO:1 or a sequence derived therefrom by one or more conservative amino acid substitutions,
  ii) the sequence of SEQ ID NO:2 or a sequence derived therefrom by one or more conservative amino acid substitutions,
  iii) the sequence of SEQ ID NO:3 or a sequence derived therefrom by one or more conservative amino acid substitutions,
  iv) the sequence of SEQ ID NO:4 or a sequence derived therefrom by one or more conservative amino acid substitutions,
  v) the sequence of SEQ ID NO:5 or a sequence derived therefrom by one or more conservative amino acid substitutions,
  vi) the sequence of SEQ ID NO:6 or a sequence derived therefrom by one or more conservative amino acid substitutions,
  vii) the sequence of SEQ ID NO:7 or a sequence derived therefrom by one or more conservative amino acid substitutions,
  viii) the sequence of SEQ ID NO:8 or a sequence derived therefrom by one or more conservative amino acid substitutions,
  ix) the sequence of SEQ ID NO:9 or a sequence derived therefrom by one or more conservative amino acid substitutions,
  x) the sequence of SEQ ID NO:10 or a sequence derived therefrom by one or more conservative amino acid substitutions,
  xi) the sequence of SEQ ID NO:11 or a sequence derived therefrom by one or more conservative amino acid substitutions,
  xii) the sequence of SEQ ID NO:12 or a sequence derived therefrom by one or more conservative amino acid substitutions,
  xiii) the sequence of SEQ ID NO:13 or a sequence derived therefrom by one or more conservative amino acid substitutions,
  xiv) the sequence of SEQ ID NO:14 or a sequence derived therefrom by one or more conservative amino acid substitutions,
  xv) the sequence of SEQ ID NO:15 or a sequence derived therefrom one or more conservative amino acid substitutions, and
  xvi) the sequence of SEQ ID NO:16 or a sequence derived therefrom by one or more conservative amino acid substitutions; and
  wherein at least two of i)-xvi) are joined by an amino acid linker, and wherein the sequence of each of i)-xvi) is 11-85 amino acids in length.

25. The expression vector of claim 24, further comprising an expression cassette, wherein the expression cassette comprises a promoter sequence, a 3'-UTR, and the nucleic acid molecule encoding the immunogenic polypeptide.

26. The expression vector of claim 25 wherein the expression cassette further comprises a selection marker.

27. The expression vector of claim 24, wherein the amino acid linker is a single, dual, or triple alanine amino acid linker, and wherein the amino acid linker results in the formation of an AAA sequence in the junction region between adjoining sequences.

28. The expression vector of claim 24, wherein the sequences of i)-xvi) are adjoined by amino acid linkers.

29. The expression vector of claim 28, wherein the amino acid linkers are single, dual, or triple alanine amino acid linkers, and wherein the amino acid linkers result in the formation of an AAA sequence in the junction region between adjoining sequences.

30. The expression vector a 24, wherein the nucleic acid molecule is codon optimized for expression in human cells.

31. A cell comprising the expression vector of claim 24.

* * * * *

SEQUENCE LISTING

```
<160> NUMBER OF SEQ ID NOS: 100

<210> SEQ ID NO 1
<211> LENGTH: 78
<212> TYPE: PRT
<213> ORGANISM: Artificial Sequence
<220> FEATURE:
<223> OTHER INFORMATION: OLP HIV clade B consensus sequence

<400> SEQUENCE: 1

Glu Lys Ile Arg Leu Arg Pro Gly Gly Lys Lys Lys Tyr Lys Leu Lys
1               5                   10                  15

His Ile Val Trp Ala Ser Arg Glu Leu Glu Arg Phe Ala Val Asn Pro
            20                  25                  30

Gly Leu Leu Glu Thr Ser Glu Gly Cys Arg Gln Ile Leu Gly Gln Leu
        35                  40                  45

Gln Pro Ser Leu Gln Thr Gly Ser Glu Glu Leu Lys Ser Leu Tyr Asn
    50                  55                  60

Thr Val Ala Thr Leu Tyr Cys Val His Gln Lys Ile Glu Val
65                  70                  75

<210> SEQ ID NO 2
<211> LENGTH: 14
<212> TYPE: PRT
<213> ORGANISM: Artificial Sequence
<220> FEATURE:
<223> OTHER INFORMATION: OLP HIV clade B consensus sequence

<400> SEQUENCE: 2

Lys Ala Phe Ser Pro Glu Val Ile Pro Met Phe Ser Ala Leu
1               5                   10
```

<210> SEQ ID NO 3
<211> LENGTH: 11
<212> TYPE: PRT
<213> ORGANISM: Artificial Sequence
<220> FEATURE:
<223> OTHER INFORMATION: OLP HIV clade B consensus sequence

<400> SEQUENCE: 3

Gly His Gln Ala Ala Met Gln Met Leu Lys Glu
1               5                   10

<210> SEQ ID NO 4
<211> LENGTH: 60
<212> TYPE: PRT
<213> ORGANISM: Artificial Sequence
<220> FEATURE:
<223> OTHER INFORMATION: OLP HIV clade B consensus sequence

<400> SEQUENCE: 4

Ile Ala Pro Gly Gln Met Arg Glu Pro Arg Gly Ser Asp Ile Ala Gly
1               5                   10                  15

Thr Thr Ser Thr Leu Gln Glu Gln Ile Gly Trp Met Thr Asn Asn Pro
            20                  25                  30

Pro Ile Pro Val Gly Glu Ile Tyr Lys Arg Trp Ile Ile Leu Gly Leu
        35                  40                  45

Asn Lys Ile Val Arg Met Tyr Ser Pro Thr Ser Ile
    50                  55                  60

<210> SEQ ID NO 5
<211> LENGTH: 14
<212> TYPE: PRT
<213> ORGANISM: Artificial Sequence
<220> FEATURE:
<223> OTHER INFORMATION: OLP HIV clade B consensus sequence

<400> SEQUENCE: 5

Tyr Val Asp Arg Phe Tyr Lys Thr Leu Arg Ala Glu Gln Ala
1               5                   10

<210> SEQ ID NO 6
<211> LENGTH: 15
<212> TYPE: PRT
<213> ORGANISM: Artificial Sequence
<220> FEATURE:
<223> OTHER INFORMATION: OLP HIV clade B consensus sequence

<400> SEQUENCE: 6

Ala Cys Gln Gly Val Gly Gly Pro Gly His Lys Ala Arg Val Leu
1               5                   10                  15

<210> SEQ ID NO 7
<211> LENGTH: 27
<212> TYPE: PRT
<213> ORGANISM: Artificial Sequence
<220> FEATURE:
<223> OTHER INFORMATION: OLP HIV clade B consensus sequence

<400> SEQUENCE: 7

Cys Thr Glu Arg Gln Ala Asn Phe Leu Gly Lys Ile Trp Pro Ser His
1               5                   10                  15

Lys Gly Arg Pro Gly Asn Phe Leu Gln Ser Arg
            20                  25

-continued

```
<210> SEQ ID NO 8
<211> LENGTH: 55
<212> TYPE: PRT
<213> ORGANISM: Artificial Sequence
<220> FEATURE:
<223> OTHER INFORMATION: OLP HIV clade B consensus sequence

<400> SEQUENCE: 8

Lys Met Ile Gly Gly Ile Gly Gly Phe Ile Lys Val Arg Gln Tyr Asp
1               5                   10                  15

Gln Ile Leu Ile Glu Ile Cys Gly His Lys Ala Ile Gly Thr Val Leu
            20                  25                  30

Val Gly Pro Thr Pro Val Asn Ile Ile Gly Arg Asn Leu Leu Thr Gln
        35                  40                  45

Ile Gly Cys Thr Leu Asn Phe
    50                  55

<210> SEQ ID NO 9
<211> LENGTH: 17
<212> TYPE: PRT
<213> ORGANISM: Artificial Sequence
<220> FEATURE:
<223> OTHER INFORMATION: OLP HIV clade B consensus sequence

<400> SEQUENCE: 9

Leu Val Glu Ile Cys Thr Glu Leu Glu Lys Glu Gly Lys Ile Ser Lys
1               5                   10                  15

Ile

<210> SEQ ID NO 10
<211> LENGTH: 55
<212> TYPE: PRT
<213> ORGANISM: Artificial Sequence
<220> FEATURE:
<223> OTHER INFORMATION: OLP HIV clade B consensus sequence

<400> SEQUENCE: 10

Leu Arg Trp Gly Phe Thr Thr Pro Asp Lys Lys His Gln Lys Glu Pro
1               5                   10                  15

Pro Phe Leu Trp Met Gly Tyr Glu Leu His Pro Asp Lys Trp Thr Val
            20                  25                  30

Gln Pro Ile Val Leu Pro Glu Lys Asp Ser Trp Thr Val Asn Asp Ile
        35                  40                  45

Gln Lys Leu Val Gly Lys Leu
    50                  55

<210> SEQ ID NO 11
<211> LENGTH: 34
<212> TYPE: PRT
<213> ORGANISM: Artificial Sequence
<220> FEATURE:
<223> OTHER INFORMATION: OLP HIV clade B consensus sequence

<400> SEQUENCE: 11

Ile Leu Lys Glu Pro Val His Gly Val Tyr Tyr Asp Pro Ser Lys Asp
1               5                   10                  15

Leu Ile Ala Glu Ile Gln Lys Gln Gly Gln Gly Gln Trp Thr Tyr Gln
            20                  25                  30

Ile Tyr

<210> SEQ ID NO 12
<211> LENGTH: 34
```

<212> TYPE: PRT
<213> ORGANISM: Artificial sequence
<220> FEATURE:
<223> OTHER INFORMATION: OLP HIV clade B consensus sequence

<400> SEQUENCE: 12

Thr Lys Glu Leu Gln Lys Gln Ile Thr Lys Ile Gln Asn Phe Arg Val
1               5                   10                  15

Tyr Tyr Arg Asp Ser Arg Asp Pro Leu Trp Lys Gly Pro Ala Lys Leu
            20                  25                  30

Leu Trp

<210> SEQ ID NO 13
<211> LENGTH: 17
<212> TYPE: PRT
<213> ORGANISM: Artificial Sequence
<220> FEATURE:
<223> OTHER INFORMATION: OLP HIV clade B consensus sequence

<400> SEQUENCE: 13

Lys Ile Ile Arg Asp Tyr Gly Lys Gln Met Ala Gly Asp Asp Cys Val
1               5                   10                  15

Ala

<210> SEQ ID NO 14
<211> LENGTH: 26
<212> TYPE: PRT
<213> ORGANISM: Artificial Sequence
<220> FEATURE:
<223> OTHER INFORMATION: OLP HIV clade B consensus sequence

<400> SEQUENCE: 14

Val Lys His His Met Tyr Ile Ser Lys Lys Ala Lys Gly Trp Phe Tyr
1               5                   10                  15

Arg His His Tyr Glu Ser Thr His Pro Arg
            20                  25

<210> SEQ ID NO 15
<211> LENGTH: 19
<212> TYPE: PRT
<213> ORGANISM: Artificial Sequence
<220> FEATURE:
<223> OTHER INFORMATION: OLP HIV clade B consensus sequence

<400> SEQUENCE: 15

Val Thr Lys Leu Thr Glu Asp Arg Trp Asn Lys Pro Gln Lys Thr Lys
1               5                   10                  15

Gly His Arg

<210> SEQ ID NO 16
<211> LENGTH: 13
<212> TYPE: PRT
<213> ORGANISM: Artificial Sequence
<220> FEATURE:
<223> OTHER INFORMATION: OLP HIV clade B consensus sequence

<400> SEQUENCE: 16

Ala Trp Leu Glu Ala Gln Glu Glu Glu Glu Val Gly Phe
1               5                   10

<210> SEQ ID NO 17
<211> LENGTH: 23
<212> TYPE: PRT
<213> ORGANISM: Artificial Sequence
<220> FEATURE:
<223> OTHER INFORMATION: OLP HIV clade B consensus sequence

<400> SEQUENCE: 17

Glu Lys Ile Arg Leu Arg Pro Gly Gly Lys Lys Lys Tyr Lys Leu Lys
1               5                   10                  15

His Ile Val Trp Ala Ser Arg
            20

<210> SEQ ID NO 18
<211> LENGTH: 22
<212> TYPE: PRT
<213> ORGANISM: Artificial Sequence
<220> FEATURE:
<223> OTHER INFORMATION: OLP HIV clade B consensus sequence

<400> SEQUENCE: 18

Lys Leu Lys His Ile Val Trp Ala Ser Arg Glu Leu Glu Arg Phe Ala
1               5                   10                  15

Val Asn Pro Gly Leu Leu
            20

<210> SEQ ID NO 19
<211> LENGTH: 23
<212> TYPE: PRT
<213> ORGANISM: Artificial Sequence
<220> FEATURE:
<223> OTHER INFORMATION: OLP HIV clade B consensus sequence

<400> SEQUENCE: 19

Glu Arg Phe Ala Val Asn Pro Gly Leu Leu Glu Thr Ser Glu Gly Cys
1               5                   10                  15

Arg Gln Ile Leu Gly Gln Leu
            20

<210> SEQ ID NO 20
<211> LENGTH: 24
<212> TYPE: PRT
<213> ORGANISM: Artificial Sequence
<220> FEATURE:
<223> OTHER INFORMATION: OLP HIV clade B consensus sequence

<400> SEQUENCE: 20

Glu Gly Cys Arg Gln Ile Leu Gly Gln Leu Gln Pro Ser Leu Gln Thr
1               5                   10                  15

Gly Ser Glu Glu Leu Lys Ser Leu
            20

<210> SEQ ID NO 21
<211> LENGTH: 26
<212> TYPE: PRT
<213> ORGANISM: Artificial Sequence
<220> FEATURE:
<223> OTHER INFORMATION: OLP HIV clade B consensus sequence

<400> SEQUENCE: 21

Gln Thr Gly Ser Glu Glu Leu Lys Ser Leu Tyr Asn Thr Val Ala Thr
1               5                   10                  15

Leu Tyr Cys Val His Gln Arg Ile Glu Val
            20                  25

<210> SEQ ID NO 22
<211> LENGTH: 14
<212> TYPE: PRT

```
<213> ORGANISM: Artificial Sequence
<220> FEATURE:
<223> OTHER INFORMATION: OLP HIV clade B consensus sequence

<400> SEQUENCE: 22

Lys Ala Phe Ser Pro Glu Val Ile Pro Met Phe Ser Ala Leu
1               5                   10

<210> SEQ ID NO 23
<211> LENGTH: 11
<212> TYPE: PRT
<213> ORGANISM: Artificial Sequence
<220> FEATURE:
<223> OTHER INFORMATION: OLP HIV clade B consensus sequence

<400> SEQUENCE: 23

Gly His Gln Ala Ala Met Gln Met Leu Lys Glu
1               5                   10

<210> SEQ ID NO 24
<211> LENGTH: 21
<212> TYPE: PRT
<213> ORGANISM: Artificial Sequence
<220> FEATURE:
<223> OTHER INFORMATION: OLP HIV clade B consensus sequence

<400> SEQUENCE: 24

Ile Ala Pro Gly Gln Met Arg Glu Pro Arg Gly Ser Asp Ile Ala Gly
1               5                   10                  15

Thr Thr Ser Thr Leu
            20

<210> SEQ ID NO 25
<211> LENGTH: 23
<212> TYPE: PRT
<213> ORGANISM: Artificial Sequence
<220> FEATURE:
<223> OTHER INFORMATION: OLP HIV clade B consensus sequence

<400> SEQUENCE: 25

Ser Asp Ile Ala Gly Thr Thr Ser Thr Leu Gln Glu Gln Ile Gly Trp
1               5                   10                  15

Met Thr Asn Asn Pro Pro Ile
            20

<210> SEQ ID NO 26
<211> LENGTH: 24
<212> TYPE: PRT
<213> ORGANISM: Artificial Sequence
<220> FEATURE:
<223> OTHER INFORMATION: OLP HIV clade B consensus sequence

<400> SEQUENCE: 26

Ile Gly Trp Met Thr Asn Asn Pro Pro Ile Pro Val Gly Glu Ile Tyr
1               5                   10                  15

Lys Arg Trp Ile Ile Leu Gly Leu
            20

<210> SEQ ID NO 27
<211> LENGTH: 22
<212> TYPE: PRT
<213> ORGANISM: Artificial Sequence
<220> FEATURE:
<223> OTHER INFORMATION: OLP HIV clade B consensus sequence

<400> SEQUENCE: 27
```

```
Ile Tyr Lys Arg Trp Ile Ile Leu Gly Leu Asn Lys Ile Val Arg Met
1               5                   10                  15

Tyr Ser Pro Thr Ser Ile
            20
```

<210> SEQ ID NO 28
<211> LENGTH: 14
<212> TYPE: PRT
<213> ORGANISM: Artificial Sequence
<220> FEATURE:
<223> OTHER INFORMATION: OLP HIV clade B consensus sequence

<400> SEQUENCE: 28

```
Tyr Val Asp Arg Phe Tyr Lys Thr Leu Arg Ala Glu Gln Ala
1               5                   10
```

<210> SEQ ID NO 29
<211> LENGTH: 15
<212> TYPE: PRT
<213> ORGANISM: Artificial Sequence
<220> FEATURE:
<223> OTHER INFORMATION: OLP HIV clade B consensus sequence

<400> SEQUENCE: 29

```
Ala Cys Gln Gly Val Gly Gly Pro Gly His Lys Ala Arg Val Leu
1               5                   10                  15
```

<210> SEQ ID NO 30
<211> LENGTH: 27
<212> TYPE: PRT
<213> ORGANISM: Artificial Sequence
<220> FEATURE:
<223> OTHER INFORMATION: OLP HIV clade B consensus sequence

<400> SEQUENCE: 30

```
Cys Thr Glu Arg Gln Ala Asn Phe Leu Gly Lys Ile Trp Pro Ser His
1               5                   10                  15

Lys Gly Arg Pro Gly Asn Phe Leu Gln Ser Arg
            20                  25
```

<210> SEQ ID NO 31
<211> LENGTH: 26
<212> TYPE: PRT
<213> ORGANISM: Artificial Sequence
<220> FEATURE:
<223> OTHER INFORMATION: OLP HIV clade B consensus sequence

<400> SEQUENCE: 31

```
Lys Met Ile Gly Gly Ile Gly Gly Phe Ile Lys Val Arg Gln Tyr Asp
1               5                   10                  15

Gln Ile Leu Ile Glu Ile Cys Gly His Lys
            20                  25
```

<210> SEQ ID NO 32
<211> LENGTH: 24
<212> TYPE: PRT
<213> ORGANISM: Artificial Sequence
<220> FEATURE:
<223> OTHER INFORMATION: OLP HIV clade B consensus sequence

<400> SEQUENCE: 32

```
Gln Ile Leu Ile Glu Ile Cys Gly His Lys Ala Ile Gly Thr Val Leu
1               5                   10                  15

Val Gly Pro Thr Pro Val Asn Ile
```

20

<210> SEQ ID NO 33
<211> LENGTH: 25
<212> TYPE: PRT
<213> ORGANISM: Artificial Sequence
<220> FEATURE:
<223> OTHER INFORMATION: OLP HIV clade B consensus sequence

<400> SEQUENCE: 33

Val Leu Val Gly Pro Thr Pro Val Asn Ile Ile Gly Arg Asn Leu Leu
1               5                   10                  15

Thr Gln Ile Gly Cys Thr Leu Asn Phe
            20                  25

<210> SEQ ID NO 34
<211> LENGTH: 17
<212> TYPE: PRT
<213> ORGANISM: Artificial Sequence
<220> FEATURE:
<223> OTHER INFORMATION: OLP HIV clade B consensus sequence

<400> SEQUENCE: 34

Leu Val Glu Ile Cys Thr Glu Met Glu Lys Glu Gly Lys Ile Ser Lys
1               5                   10                  15

Ile

<210> SEQ ID NO 35
<211> LENGTH: 25
<212> TYPE: PRT
<213> ORGANISM: Artificial Sequence
<220> FEATURE:
<223> OTHER INFORMATION: OLP HIV clade B consensus sequence

<400> SEQUENCE: 35

Leu Arg Trp Gly Phe Thr Thr Pro Asp Lys Lys His Gln Lys Glu Pro
1               5                   10                  15

Pro Phe Leu Trp Met Gly Tyr Glu Leu
            20                  25

<210> SEQ ID NO 36
<211> LENGTH: 25
<212> TYPE: PRT
<213> ORGANISM: Artificial Sequence
<220> FEATURE:
<223> OTHER INFORMATION: OLP HIV clade B consensus sequence

<400> SEQUENCE: 36

Pro Pro Phe Leu Trp Met Gly Tyr Glu Leu His Pro Asp Lys Trp Thr
1               5                   10                  15

Val Gln Pro Ile Val Leu Pro Glu Lys
            20                  25

<210> SEQ ID NO 37
<211> LENGTH: 25
<212> TYPE: PRT
<213> ORGANISM: Artificial Sequence
<220> FEATURE:
<223> OTHER INFORMATION: OLP HIV clade B consensus sequence

<400> SEQUENCE: 37

Thr Val Gln Pro Ile Val Leu Pro Glu Lys Asp Ser Trp Thr Val Asn
1               5                   10                  15

Asp Ile Gln Lys Leu Val Gly Lys Leu 20                  25

<210> SEQ ID NO 38
<211> LENGTH: 23
<212> TYPE: PRT
<213> ORGANISM: Artificial Sequence
<220> FEATURE:
<223> OTHER INFORMATION: OLP HIV clade B consensus sequence

<400> SEQUENCE: 38

Ile Leu Lys Glu Pro Val His Gly Val Tyr Tyr Asp Pro Ser Lys Asp
1               5                   10                  15

Leu Ile Ala Glu Ile Gln Lys
            20

<210> SEQ ID NO 39
<211> LENGTH: 21
<212> TYPE: PRT
<213> ORGANISM: Artificial Sequence
<220> FEATURE:
<223> OTHER INFORMATION: OLP HIV clade B consensus sequence

<400> SEQUENCE: 39

Ser Lys Asp Leu Ile Ala Glu Ile Gln Lys Gln Gly Gln Gly Gln Trp
1               5                   10                  15

Thr Tyr Gln Ile Tyr
            20

<210> SEQ ID NO 40
<211> LENGTH: 22
<212> TYPE: PRT
<213> ORGANISM: Artificial Sequence
<220> FEATURE:
<223> OTHER INFORMATION: OLP HIV clade B consensus sequence

<400> SEQUENCE: 40

Thr Lys Glu Leu Gln Lys Gln Ile Thr Lys Ile Gln Asn Phe Arg Val
1               5                   10                  15

Tyr Tyr Arg Asp Ser Arg
            20

<210> SEQ ID NO 41
<211> LENGTH: 22
<212> TYPE: PRT
<213> ORGANISM: Artificial Sequence
<220> FEATURE:
<223> OTHER INFORMATION: OLP HIV clade B consensus sequence

<400> SEQUENCE: 41

Asn Phe Arg Val Tyr Tyr Arg Asp Ser Arg Asp Pro Leu Trp Lys Gly
1               5                   10                  15

Pro Ala Lys Leu Leu Trp
            20

<210> SEQ ID NO 42
<211> LENGTH: 17
<212> TYPE: PRT
<213> ORGANISM: Artificial Sequence
<220> FEATURE:
<223> OTHER INFORMATION: OLP HIV clade B consensus sequence

<400> SEQUENCE: 42

Lys Ile Ile Arg Asp Tyr Gly Lys Gln Met Ala Gly Asp Asp Cys Val
1               5                   10                  15

Ala

<210> SEQ ID NO 43
<211> LENGTH: 26
<212> TYPE: PRT
<213> ORGANISM: Artificial Sequence
<220> FEATURE:
<223> OTHER INFORMATION: OLP HIV clade B consensus sequence

<400> SEQUENCE: 43

Val Lys His His Met Tyr Ile Ser Lys Lys Ala Lys Gly Trp Phe Tyr
1               5                   10                  15

Arg His His Tyr Glu Ser Thr His Pro Arg
            20                  25

<210> SEQ ID NO 44
<211> LENGTH: 19
<212> TYPE: PRT
<213> ORGANISM: Artificial Sequence
<220> FEATURE:
<223> OTHER INFORMATION: OLP HIV clade B consensus sequence

<400> SEQUENCE: 44

Val Thr Lys Leu Thr Glu Asp Arg Trp Asn Lys Pro Gln Lys Thr Lys
1               5                   10                  15

Gly His Arg

<210> SEQ ID NO 45
<211> LENGTH: 13
<212> TYPE: PRT
<213> ORGANISM: Artificial Sequence
<220> FEATURE:
<223> OTHER INFORMATION: OLP HIV clade B consensus sequence

<400> SEQUENCE: 45

Ala Trp Leu Glu Ala Gln Glu Glu Glu Glu Val Gly Phe
1               5                   10

<210> SEQ ID NO 46
<211> LENGTH: 17
<212> TYPE: PRT
<213> ORGANISM: Homo sapiens

<400> SEQUENCE: 46

Met Trp Leu Gln Ser Leu Leu Leu Leu Gly Thr Val Ala Cys Ser Ile
1               5                   10                  15

Ser

<210> SEQ ID NO 47
<211> LENGTH: 18
<212> TYPE: PRT
<213> ORGANISM: Artificial Sequence
<220> FEATURE:
<223> OTHER INFORMATION: human GM-CSF signal peptide + V

<400> SEQUENCE: 47

Met Trp Leu Gln Ser Leu Leu Leu Leu Gly Thr Val Ala Cys Ser Ile
1               5                   10                  15

Ser Val

<210> SEQ ID NO 48
<211> LENGTH: 9
<212> TYPE: PRT
<213> ORGANISM: Artificial Sequence
<220> FEATURE:
<223> OTHER INFORMATION: Flag-tag

<400> SEQUENCE: 48

```
Asp Tyr Lys Asp Asp Asp Asp Lys Leu
1               5
```

<210> SEQ ID NO 49
<211> LENGTH: 556
<212> TYPE: PRT
<213> ORGANISM: Artificial Sequence
<220> FEATURE:
<223> OTHER INFORMATION: HIV immunogen comprising OLPs

<400> SEQUENCE: 49

```
Met Trp Leu Gln Ser Leu Leu Leu Gly Thr Val Ala Cys Ser Ile
1               5                   10                  15

Ser Val Glu Lys Ile Arg Leu Arg Pro Gly Gly Lys Lys Tyr Lys
                20                  25                  30

Leu Lys His Ile Val Trp Ala Ser Arg Glu Leu Glu Arg Phe Ala Val
            35                  40                  45

Asn Pro Gly Leu Leu Glu Thr Ser Glu Gly Cys Arg Gln Ile Leu Gly
50                  55                  60

Gln Leu Gln Pro Ser Leu Gln Thr Gly Ser Glu Glu Leu Lys Ser Leu
65                  70                  75                  80

Tyr Asn Thr Val Ala Thr Leu Tyr Cys Val His Gln Lys Ile Glu Val
                85                  90                  95

Ala Ala Ala Lys Ala Phe Ser Pro Glu Val Ile Pro Met Phe Ser Ala
            100                 105                 110

Leu Ala Ala Ala Gly His Gln Ala Ala Met Gln Met Leu Lys Glu Ala
        115                 120                 125

Ala Ala Ile Ala Pro Gly Gln Met Arg Glu Pro Arg Gly Ser Asp Ile
130                 135                 140

Ala Gly Thr Thr Ser Thr Leu Gln Glu Gln Ile Gly Trp Met Thr Asn
145                 150                 155                 160

Asn Pro Pro Ile Pro Val Gly Glu Ile Tyr Lys Arg Trp Ile Ile Leu
                165                 170                 175

Gly Leu Asn Lys Ile Val Arg Met Tyr Ser Pro Thr Ser Ile Ala Ala
            180                 185                 190

Ala Tyr Val Asp Arg Phe Tyr Lys Thr Leu Arg Ala Glu Gln Ala Ala
        195                 200                 205

Ala Cys Gln Gly Val Gly Gly Pro Gly His Lys Ala Arg Val Leu Ala
210                 215                 220

Ala Ala Cys Thr Glu Arg Gln Ala Asn Phe Leu Gly Lys Ile Trp Pro
225                 230                 235                 240

Ser His Lys Gly Arg Pro Gly Asn Phe Leu Gln Ser Arg Ala Ala Ala
                245                 250                 255

Lys Met Ile Gly Gly Ile Gly Gly Phe Ile Lys Val Arg Gln Tyr Asp
            260                 265                 270

Gln Ile Leu Ile Glu Ile Cys Gly His Lys Ala Ile Gly Thr Val Leu
        275                 280                 285

Val Gly Pro Thr Pro Val Asn Ile Ile Gly Arg Asn Leu Leu Thr Gln
290                 295                 300

Ile Gly Cys Thr Leu Asn Phe Ala Ala Leu Val Glu Ile Cys Thr Glu
305                 310                 315                 320

Met Glu Lys Glu Gly Lys Ile Ser Lys Ile Ala Ala Ala Leu Arg Trp
```

|   |   |   | 325 |   |   |   |   | 330 |   |   |   |   | 335 |   |
|---|---|---|---|---|---|---|---|---|---|---|---|---|---|---|
Gly Phe Thr Thr Pro Asp Lys Lys His Gln Lys Glu Pro Phe Leu
                340                    345                  350

Trp Met Gly Tyr Glu Leu His Pro Asp Lys Trp Thr Val Gln Pro Ile
        355                  360                    365

Val Leu Pro Glu Lys Asp Ser Trp Thr Val Asn Asp Ile Gln Lys Leu
370                    375                    380

Val Gly Lys Leu Ala Ala Ala Ile Leu Lys Glu Pro Val His Gly Val
385                    390                    395                  400

Tyr Tyr Asp Pro Ser Lys Asp Leu Ile Ala Glu Ile Gln Lys Gln Gly
                405                    410                    415

Gln Gly Gln Trp Thr Tyr Gln Ile Tyr Ala Ala Thr Lys Glu Leu
                420                    425                  430

Gln Lys Gln Ile Thr Lys Ile Gln Asn Phe Arg Val Tyr Tyr Arg Asp
                435                    440                  445

Ser Arg Asp Pro Leu Trp Lys Gly Pro Ala Lys Leu Leu Trp Ala Ala
450                    455                    460

Ala Lys Ile Ile Arg Asp Tyr Gly Lys Gln Met Ala Gly Asp Asp Cys
465                    470                    475                  480

Val Ala Ala Val Lys His His Met Tyr Ile Ser Lys Lys Ala Lys
                485                    490                  495

Gly Trp Phe Tyr Arg His His Tyr Glu Ser Thr His Pro Arg Ala Ala
                500                    505                  510

Ala Val Thr Lys Leu Thr Glu Asp Arg Trp Asn Lys Pro Gln Lys Thr
                515                    520                  525

Lys Gly His Arg Ala Ala Ala Trp Leu Glu Ala Gln Glu Glu Glu
                530                    535                  540

Val Gly Phe Asp Tyr Lys Asp Asp Asp Lys Leu
545                    550                    555

<210> SEQ ID NO 50
<211> LENGTH: 1674
<212> TYPE: DNA
<213> ORGANISM: Artificial Sequence
<220> FEATURE:
<223> OTHER INFORMATION: polynucleotide encoding immunogen comprising
    HIV OLPs

<400> SEQUENCE: 50

```
atgtggctcc agagcctgct actcctgggg acggtggcct gcagcatctc ggtcgagaag      60
atccggctgc ggccaggcgg aaagaagaag tacaagctga gcacatcgt ctgggcctcg     120
agggagctgg agcggttcgc ggtgaacccg ggacttctgg agacgtcgga ggggtgcagg     180
cagatcctcg gccagctgca gccctctctg caaacggggt ctgaggagct gaagagcctg     240
tacaacacgg tggcgaccct ctactgcgtc accagaaga tcgaggtggc agcggccaag     300
gcgttctcgc cggaggtcat ccccatgttc tcggcgctgg cagctgccgg acaccaggcc     360
gcgatgcaga tgctgaagga ggccgctgcg atcgcaccgg ccagatgag ggagccacgc     420
ggttccgaca tcgcgggaac cacctcgacg ctccaggagc agatcggatg gatgacgaac     480
aacccgccaa tccggtcgg ggagatctac aagcggtgga tcatcctcgg ctgaacaag     540
atcgtccgga tgtacagccc gacgtcgatc gctgcggcat acgttgaccg gttctacaag     600
accctgaggg ccgagcaggc agcggcctgc caggggtcg gtggaccagg cacaaggcc     660
cgagtgctcg cggccgcatg cacggagcgg caggcgaact tcctggggaa gatctggccg     720
```

-continued

```
tcgcacaagg gccgaccggg aaacttcctc cagtctcgcg cagcggctaa gatgatcgga    780
ggcatcggag gcttcatcaa agtccgtcag tacgaccaga tcctcatcga gatctgcggg    840
cacaaggcga tcggaaccgt gctcgtcggc ccaacgcccg tgaacatcat cggccgcaac    900
ctgttaacgc agatcggctg caccctcaac ttcgccgcac tagtggagat ctgcacggag    960
atggagaagg agggcaagat atcgaagatc gcggcagctc tgaggtgggg cttcaccacg   1020
ccggacaaga agcaccagaa ggagccgcca ttcctgtgga tgggatacga gctgcacccg   1080
gacaagtgga ccgtgcagcc catcgtcctg ccggagaagg actcgtggac ggtgaacgac   1140
atccagaagc tcgtggggaa gctggcggca gccatcctca aggagcccgt ccacggggtg   1200
tactacgacc cctctaagga cctgatcgcg gagatccaga agcaggggca gggtcagtgg   1260
acctaccaga tctacgcagc agcaaccaag gagctgcaga agcagatcac gaagatccag   1320
aacttccgcg tatactaccg cgactcgcgg gacccctgt ggaagggccc tgcgaagctt    1380
ctctgggcag ccgcgaagat catccggac tacggcaagc agatggcggg cgacgactgc     1440
gtggccgcag cggtgaagca ccatatgtac atctcgaaga aggcgaaggg ctggttctac   1500
agacaccact acgagtccac ccaccccagg gcagctgcgg tgacgaagct gacggaggac   1560
cggtggaaca agccccagaa gacgaagggt caccgggcgg ctgcatggct ggaggctcag   1620
gaggaggagg aggtgggctt cgattacaag gacgatgacg acaagctgtg ataa         1674
```

<210> SEQ ID NO 51
<211> LENGTH: 60
<212> TYPE: DNA
<213> ORGANISM: Artificial Sequence
<220> FEATURE:
<223> OTHER INFORMATION: 198HPlus primer

<400> SEQUENCE: 51

```
gtcaccgggc ggctgcatgg ctggaggctc aggaggagga ggaggtgggc ttctgataag    60
```

<210> SEQ ID NO 52
<211> LENGTH: 59
<212> TYPE: DNA
<213> ORGANISM: Artificial Sequence
<220> FEATURE:
<223> OTHER INFORMATION: 298HMinus primer

<400> SEQUENCE: 52

```
aattcttatc agaagcccac ctcctcctcc tcctgagcct ccagccatgc agccgcccg     59
```

<210> SEQ ID NO 53
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 53

Glu Lys Ile Arg Leu Arg Pro Gly Gly Lys Lys Tyr Lys Leu Lys
1               5                   10                  15

His Ile

<210> SEQ ID NO 54
<211> LENGTH: 15
<212> TYPE: PRT
<213> ORGANISM: Artificial Sequence
<220> FEATURE:
<223> OTHER INFORMATION: OLP clade B consensus sequence

```
<400> SEQUENCE: 54

Ala Ser Arg Glu Leu Glu Arg Phe Ala Val Asn Pro Gly Leu Leu
1               5                   10                  15

<210> SEQ ID NO 55
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 55

Glu Arg Phe Ala Val Asn Pro Gly Leu Leu Glu Thr Ser Glu Gly Cys
1               5                   10                  15

Arg

<210> SEQ ID NO 56
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 56

Gln Leu Gln Pro Ser Leu Gln Thr Gly Ser Glu Glu Leu Arg Ser Leu
1               5                   10                  15

Tyr

<210> SEQ ID NO 57
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 57

Ser Leu Tyr Asn Thr Val Ala Thr Leu Tyr Cys Val His Gln Arg Ile
1               5                   10                  15

Glu Val

<210> SEQ ID NO 58
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 58

Ala Phe Ser Pro Glu Val Ile Pro Met Phe Ser Ala Leu Ser Glu Gly
1               5                   10                  15

Ala

<210> SEQ ID NO 59
<211> LENGTH: 15
<212> TYPE: PRT
<213> ORGANISM: Artificial Sequence
<220> FEATURE:
<223> OTHER INFORMATION: OLP clade B consensus sequence

<400> SEQUENCE: 59

Ile Ala Pro Gly Gln Met Arg Glu Pro Arg Gly Ser Asp Ile Ala
1               5                   10                  15
```

```
<210> SEQ ID NO 60
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 60

Ser Thr Leu Gln Glu Gln Ile Gly Trp Met Thr Asn Asn Pro Pro Ile
1               5                   10                  15

Pro Val

<210> SEQ ID NO 61
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 61

Ala Cys Gln Gly Val Gly Gly Pro Gly His Lys Ala Arg Val Leu Ala
1               5                   10                  15

Glu Ala

<210> SEQ ID NO 62
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 62

Gly Lys Ile Trp Pro Ser His Lys Gly Arg Pro Gly Asn Phe Leu Gln
1               5                   10                  15

Ser Arg

<210> SEQ ID NO 63
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 63

Trp Leu Glu Ala Gln Glu Glu Glu Val Gly Phe Pro Val Arg Pro
1               5                   10                  15

Gln Val

<210> SEQ ID NO 64
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 64

Glu Val Gly Phe Pro Val Arg Pro Gln Val Pro Leu Arg Pro Met Thr
1               5                   10                  15

Tyr Lys

<210> SEQ ID NO 65
<211> LENGTH: 18
<212> TYPE: PRT
<213> ORGANISM: Artificial Sequence
```

```
<220> FEATURE:
<223> OTHER INFORMATION: OLP clade B consensus sequence

<400> SEQUENCE: 65

Asn Tyr Thr Pro Gly Pro Gly Ile Arg Tyr Pro Leu Thr Phe Gly Trp
1               5                   10                  15

Cys Phe

<210> SEQ ID NO 66
<211> LENGTH: 15
<212> TYPE: PRT
<213> ORGANISM: Artificial Sequence
<220> FEATURE:
<223> OTHER INFORMATION: OLP clade B consensus sequence

<400> SEQUENCE: 66

Arg Tyr Pro Leu Thr Phe Gly Trp Cys Phe Lys Leu Val Pro Val
1               5                   10                  15

<210> SEQ ID NO 67
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 67

Ser Leu His Gly Met Asp Asp Pro Glu Lys Glu Val Leu Val Trp Lys
1               5                   10                  15

Phe

<210> SEQ ID NO 68
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 68

Lys Met Ile Gly Gly Ile Gly Gly Phe Ile Lys Val Arg Gln Tyr Asp
1               5                   10                  15

Gln Ile

<210> SEQ ID NO 69
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 69

Phe Ile Lys Val Arg Gln Tyr Asp Gln Ile Leu Ile Glu Ile Cys Gly
1               5                   10                  15

His Lys

<210> SEQ ID NO 70
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 70

Gln Ile Leu Ile Glu Ile Cys Gly His Lys Ala Ile Gly Thr Val Leu
```

-continued

```
1               5                   10                  15

Val

<210> SEQ ID NO 71
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 71

Leu Val Gly Pro Thr Pro Val Asn Ile Ile Gly Arg Asn Leu Leu Thr
1               5                   10                  15

Gln Ile

<210> SEQ ID NO 72
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 72

Leu Val Glu Ile Cys Thr Glu Met Glu Lys Glu Gly Lys Ile Ser Lys
1               5                   10                  15

Ile

<210> SEQ ID NO 73
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 73

Leu Asp Val Gly Asp Ala Tyr Phe Ser Val Pro Leu Asp Lys Asp Phe
1               5                   10                  15

Arg Lys

<210> SEQ ID NO 74
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 74

Leu Arg Trp Gly Phe Thr Thr Pro Asp Lys Lys His Gln Lys Glu Pro
1               5                   10                  15

Pro Phe

<210> SEQ ID NO 75
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 75

Asp Lys Lys His Gln Lys Glu Pro Pro Phe Leu Trp Met Gly Tyr Glu
1               5                   10                  15

Leu His
```

```
<210> SEQ ID NO 76
<211> LENGTH: 15
<212> TYPE: PRT
<213> ORGANISM: Artificial Sequence
<220> FEATURE:
<223> OTHER INFORMATION: OLP clade B consensus sequence

<400> SEQUENCE: 76

Glu Ile Gln Lys Gln Gly Gln Gly Gln Trp Thr Tyr Gln Ile Tyr
1               5                   10                  15

<210> SEQ ID NO 77
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 77

Pro Pro Leu Val Lys Leu Trp Tyr Gln Leu Glu Lys Glu Pro Ile Val
1               5                   10                  15

Gly Ala

<210> SEQ ID NO 78
<211> LENGTH: 15
<212> TYPE: PRT
<213> ORGANISM: Artificial Sequence
<220> FEATURE:
<223> OTHER INFORMATION: OLP clade B consensus sequence

<400> SEQUENCE: 78

Ile His Leu Ala Leu Gln Asp Ser Gly Leu Glu Val Asn Ile Val
1               5                   10                  15

<210> SEQ ID NO 79
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 79

Val Tyr Leu Ala Trp Val Pro Ala His Lys Gly Ile Gly Gly Asn Glu
1               5                   10                  15

Gln Val

<210> SEQ ID NO 80
<211> LENGTH: 16
<212> TYPE: PRT
<213> ORGANISM: Artificial Sequence
<220> FEATURE:
<223> OTHER INFORMATION: OLP clade B consensus sequence

<400> SEQUENCE: 80

Ser Ala Gly Ile Arg Lys Val Leu Phe Leu Asp Gly Ile Asp Lys Ala
1               5                   10                  15

<210> SEQ ID NO 81
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 81
```

```
Thr Lys Glu Leu Gln Lys Gln Ile Thr Lys Ile Gln Asn Phe Arg Val
1               5                   10                  15

Tyr Tyr
```

<210> SEQ ID NO 82
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 82

```
Thr Lys Ile Gln Asn Phe Arg Val Tyr Tyr Arg Asp Ser Arg Asp Pro
1               5                   10                  15

Leu Trp
```

<210> SEQ ID NO 83
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 83

```
Tyr Tyr Arg Asp Ser Arg Asp Pro Leu Trp Lys Gly Pro Ala Lys Leu
1               5                   10                  15

Leu Trp
```

<210> SEQ ID NO 84
<211> LENGTH: 17
<212> TYPE: PRT
<213> ORGANISM: Artificial Sequence
<220> FEATURE:
<223> OTHER INFORMATION: OLP clade B consensus sequence

<400> SEQUENCE: 84

```
Lys Ile Ile Arg Asp Tyr Gly Lys Gln Met Ala Gly Asp Asp Cys Val
1               5                   10                  15

Ala
```

<210> SEQ ID NO 85
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 85

```
Gly Pro Gln Arg Glu Pro Tyr Asn Glu Trp Thr Leu Glu Leu Leu Glu
1               5                   10                  15

Glu Leu
```

<210> SEQ ID NO 86
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 86

```
Asp Leu Asn Asn Asn Thr Asn Thr Thr Ser Ser Ser Gly Glu Lys Met
1               5                   10                  15

Glu Lys
```

<210> SEQ ID NO 87
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 87

Ile Arg Asp Lys Val Gln Lys Glu Tyr Ala Leu Phe Tyr Lys Leu Asp
1               5                   10                  15

Val Val

<210> SEQ ID NO 88
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 88

Tyr Arg Leu Ile Ser Cys Asn Thr Ser Val Ile Thr Gln Ala Cys Pro
1               5                   10                  15

Lys Val

<210> SEQ ID NO 89
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 89

Ser Val Ile Thr Gln Ala Cys Pro Lys Val Ser Phe Glu Pro Ile Pro
1               5                   10                  15

Ile His

<210> SEQ ID NO 90
<211> LENGTH: 16
<212> TYPE: PRT
<213> ORGANISM: Artificial Sequence
<220> FEATURE:
<223> OTHER INFORMATION: OLP clade B consensus sequence

<400> SEQUENCE: 90

Thr Asn Val Ser Thr Val Gln Cys Thr His Gly Ile Arg Pro Val Val
1               5                   10                  15

<210> SEQ ID NO 91
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 91

Val Ala Pro Thr Lys Ala Lys Arg Arg Val Val Gln Arg Glu Lys Arg
1               5                   10                  15

Ala Val

<210> SEQ ID NO 92
<211> LENGTH: 18
<212> TYPE: PRT
<213> ORGANISM: Artificial Sequence

```
<220> FEATURE:
<223> OTHER INFORMATION: OLP clade B consensus sequence

<400> SEQUENCE: 92

Val Ile Glu Val Val Gln Arg Ala Cys Arg Ala Ile Leu His Ile Pro
1               5                   10                  15
Arg Arg

<210> SEQ ID NO 93
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 93

Val Lys His His Met Tyr Ile Ser Gly Lys Ala Lys Gly Trp Phe Tyr
1               5                   10                  15
Arg His

<210> SEQ ID NO 94
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 94

Gly Lys Ala Lys Gly Trp Phe Tyr Arg His His Tyr Glu Ser Thr His
1               5                   10                  15
Pro Arg

<210> SEQ ID NO 95
<211> LENGTH: 18
<212> TYPE: PRT
<213> ORGANISM: Artificial Sequence
<220> FEATURE:
<223> OTHER INFORMATION: OLP clade B consensus sequence

<400> SEQUENCE: 95

Thr Lys Leu Thr Glu Asp Arg Trp Asn Lys Pro Gln Lys Thr Lys Gly
1               5                   10                  15
His Arg

<210> SEQ ID NO 96
<211> LENGTH: 6
<212> TYPE: PRT
<213> ORGANISM: Artificial Sequence
<220> FEATURE:
<223> OTHER INFORMATION: Tag sequence

<400> SEQUENCE: 96

Ala His Gly His Arg Pro
1               5

<210> SEQ ID NO 97
<211> LENGTH: 14
<212> TYPE: PRT
<213> ORGANISM: Artificial Sequence
<220> FEATURE:
<223> OTHER INFORMATION: Tag sequence

<400> SEQUENCE: 97

Pro Ile His Asp His Asp His Pro His Leu Val Ile His Ser
```

```
<210> SEQ ID NO 98
<211> LENGTH: 7
<212> TYPE: PRT
<213> ORGANISM: Artificial Sequence
<220> FEATURE:
<223> OTHER INFORMATION: Tag sequence
<220> FEATURE:
<221> NAME/KEY: misc_feature
<222> LOCATION: (5)..(6)
<223> OTHER INFORMATION: Xaa can be any naturally occurring amino acid

<400> SEQUENCE: 98

Gly Met Thr Cys Xaa Xaa Cys
1               5

<210> SEQ ID NO 99
<211> LENGTH: 530
<212> TYPE: PRT
<213> ORGANISM: Artificial Sequence
<220> FEATURE:
<223> OTHER INFORMATION: HIV immunogen comprising OLPs

<400> SEQUENCE: 99

Glu Lys Ile Arg Leu Arg Pro Gly Gly Lys Lys Tyr Lys Leu Lys
1               5                   10                  15

His Ile Val Trp Ala Ser Arg Glu Leu Glu Arg Phe Ala Val Asn Pro
            20                  25                  30

Gly Leu Leu Glu Thr Ser Glu Gly Cys Arg Gln Ile Leu Gly Gln Leu
        35                  40                  45

Gln Pro Ser Leu Gln Thr Gly Ser Glu Glu Leu Lys Ser Leu Tyr Asn
    50                  55                  60

Thr Val Ala Thr Leu Tyr Cys Val His Gln Lys Ile Glu Val Ala Ala
65                  70                  75                  80

Ala Lys Ala Phe Ser Pro Glu Val Ile Pro Met Phe Ser Ala Leu Ala
                85                  90                  95

Ala Ala Gly His Gln Ala Ala Met Gln Met Leu Lys Glu Ala Ala Ala
            100                 105                 110

Ile Ala Pro Gly Gln Met Arg Glu Pro Arg Gly Ser Asp Ile Ala Gly
        115                 120                 125

Thr Thr Ser Thr Leu Gln Glu Gln Ile Gly Trp Met Thr Asn Asn Pro
    130                 135                 140

Pro Ile Pro Val Gly Glu Ile Tyr Lys Arg Trp Ile Ile Leu Gly Leu
145                 150                 155                 160

Asn Lys Ile Val Arg Met Tyr Ser Pro Thr Ser Ile Ala Ala Ala Tyr
                165                 170                 175

Val Asp Arg Phe Tyr Lys Thr Leu Arg Ala Glu Gln Ala Ala Ala Cys
            180                 185                 190

Gln Gly Val Gly Gly Pro Gly His Lys Ala Arg Val Leu Ala Ala Ala
        195                 200                 205

Cys Thr Glu Arg Gln Ala Asn Phe Leu Gly Lys Ile Trp Pro Ser His
    210                 215                 220

Lys Gly Arg Pro Gly Asn Phe Leu Gln Ser Arg Ala Ala Ala Lys Met
225                 230                 235                 240

Ile Gly Gly Ile Gly Gly Phe Ile Lys Val Arg Gln Tyr Asp Gln Ile
                245                 250                 255

Leu Ile Glu Ile Cys Gly His Lys Ala Ile Gly Thr Val Leu Val Gly
            260                 265                 270
```

```
Pro Thr Pro Val Asn Ile Ile Gly Arg Asn Leu Leu Thr Gln Ile Gly
        275                 280                 285
Cys Thr Leu Asn Phe Ala Ala Ala Leu Val Glu Ile Cys Thr Glu Met
    290                 295                 300
Glu Lys Glu Gly Lys Ile Ser Lys Ile Ala Ala Ala Leu Arg Trp Gly
305                 310                 315                 320
Phe Thr Thr Pro Asp Lys Lys His Gln Lys Glu Pro Pro Phe Leu Trp
                325                 330                 335
Met Gly Tyr Glu Leu His Pro Asp Lys Trp Thr Val Gln Pro Ile Val
            340                 345                 350
Leu Pro Glu Lys Asp Ser Trp Thr Val Asn Asp Ile Gln Lys Leu Val
        355                 360                 365
Gly Lys Leu Ala Ala Ala Ile Leu Lys Glu Pro Val His Gly Val Tyr
    370                 375                 380
Tyr Asp Pro Ser Lys Asp Leu Ile Ala Glu Ile Gln Lys Gln Gly Gln
385                 390                 395                 400
Gly Gln Trp Thr Tyr Gln Ile Tyr Ala Ala Ala Thr Lys Glu Leu Gln
                405                 410                 415
Lys Gln Ile Thr Lys Ile Gln Asn Phe Arg Val Tyr Tyr Arg Asp Ser
            420                 425                 430
Arg Asp Pro Leu Trp Lys Gly Pro Ala Lys Leu Leu Trp Ala Ala Ala
        435                 440                 445
Lys Ile Ile Arg Asp Tyr Gly Lys Gln Met Ala Gly Asp Asp Cys Val
    450                 455                 460
Ala Ala Ala Val Lys His His Met Tyr Ile Ser Lys Lys Ala Lys Gly
465                 470                 475                 480
Trp Phe Tyr Arg His His Tyr Glu Ser Thr His Pro Arg Ala Ala Ala
                485                 490                 495
Val Thr Lys Leu Thr Glu Asp Arg Trp Asn Lys Pro Gln Lys Thr Lys
            500                 505                 510
Gly His Arg Ala Ala Ala Trp Leu Glu Ala Gln Glu Glu Glu Glu Val
        515                 520                 525
Gly Phe
530

<210> SEQ ID NO 100
<211> LENGTH: 1587
<212> TYPE: DNA
<213> ORGANISM: Artificial Sequence
<220> FEATURE:
<223> OTHER INFORMATION: polynucleotide encoding immunogen comprising
      HIV OLPs

<400> SEQUENCE: 100
gagaagatcc ggctgcggcc aggcggaaag aagaagtaca agctgaagca catcgtctgg      60
gcctcgaggg agctggagcg gttcgcggtg aacccgggac ttctggagac gtcggagggg     120
tgcaggcaga tcctcggcca gctgcagccc tctctgcaaa cggggtctga ggagctgaag     180
agcctgtaca acacggtggc gaccctctac tgcgtccacc agaagatcga ggtggcagcg     240
gccaaggcgt tctcgccgga ggtcatcccc atgttctcgg cgctggcagc tgccggacac     300
caggccgcga tgcagatgct gaaggaggcc gctgcgatcg caccgggcca gatgagggag     360
ccacgcggtt ccgacatcgc gggaaccacc tcgacgctcc aggagcagat cggatggatg     420
acgaacaacc cgccaatccc ggtcggggag atctacaagc ggtggatcat cctcgggctg     480
```

```
aacaagatcg tccggatgta cagcccgacg tcgatcgctg cggcatacgt tgaccggttc      540
tacaagaccc tgagggccga gcaggcagcg gcctgccagg gggtcggtgg accagggcac      600
aaggcccgag tgctcgcggc cgcatgcacg gagcggcagg cgaacttcct ggggaagatc      660
tggccgtcgc acaagggccg accgggaaac ttcctccagt ctcgcgcagc ggctaagatg      720
atcggaggca tcggaggctt catcaaagtc cgtcagtacg accagatcct catcgagatc      780
tgcgggcaca aggcgatcgg aaccgtgctc gtcggcccaa cgcccgtgaa catcatcggc      840
cgcaacctgt taacgcagat cggctgcacc ctcaacttcg ccgcactagt ggagatctgc      900
acggagatgg agaaggaggg caagatatcg aagatcgcgg cagctctgag gtggggcttc      960
accacgccgg acaagaagca ccagaaggag ccgccattcc tgtggatggg atacgagctg     1020
cacccggaca agtggaccgt gcagcccatc gtcctgccgg agaaggactc gtggacggtg     1080
aacgacatcc agaagctcgt ggggaagctg gcggcagcca tcctcaagga gcccgtccac     1140
ggggtgtact acgacccctc taaggacctg atcgcggaga tccagaagca ggggcagggt     1200
cagtggacct accagatcta cgcagcagca accaaggagc tgcagaagca gatcacgaag     1260
atccagaact tccgcgtata ctaccgcgac tcgcgggacc ccctgtggaa gggccctgcg     1320
aagcttctct gggcagccgc gaagatcatc cgggactacg gcaagcagat ggcgggcgac     1380
gactgcgtgg ccgcagcggt gaagcaccat atgtacatct cgaagaaggc gaagggctgg     1440
ttctacagac accactacga gtccaccac cccaggcag ctgcggtgac gaagctgacg     1500
gaggaccggt ggaacaagcc ccagaagacg aagggtcacc gggcggctgc atggctggag     1560
gctcaggagg aggaggaggt gggcttc                                         1587
```